United States Patent
Johnsen et al.

(10) Patent No.: US 11,138,554 B2
(45) Date of Patent: Oct. 5, 2021

(54) AUTOMATED INSPECTION SYSTEM

(71) Applicant: Walmart Apollo, LLC, Bentonville, AR (US)

(72) Inventors: Brandon Johnsen, Bentonville, AR (US); Terry Osbon, Fayetteville, AR (US); Riley Turben, Bentonville, AR (US); Joshua Bohling, Centerton, AR (US); Craig Trudo, Centerton, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 118 days.

(21) Appl. No.: 15/970,300

(22) Filed: May 3, 2018

(65) Prior Publication Data
US 2018/0341905 A1 Nov. 29, 2018

Related U.S. Application Data

(60) Provisional application No. 62/509,945, filed on May 23, 2017.

(51) Int. Cl.
*G06Q 10/08* (2012.01)
*G06F 16/2455* (2019.01)
*H04W 4/38* (2018.01)
*H04W 4/35* (2018.01)
*G01N 33/02* (2006.01)

(52) U.S. Cl.
CPC .......... *G06Q 10/087* (2013.01); *G01N 33/02* (2013.01); *G06F 16/24564* (2019.01); *H04W 4/35* (2018.02); *H04W 4/38* (2018.02)

(58) Field of Classification Search
CPC ........ G06Q 10/087; H04W 4/35; H04W 4/38; G01N 33/02; G06F 16/24564
USPC ..................................... 705/28–30
See application file for complete search history.

(56) References Cited

U.S. PATENT DOCUMENTS

| 5,369,995 A | 12/1994 | Scheinbeim |
| 5,621,162 A | 4/1997 | Yun |
| 5,671,362 A | 9/1997 | Cowe |
| 5,774,053 A | 6/1998 | Porter |
| 5,791,497 A | 8/1998 | Campbell |

(Continued)

FOREIGN PATENT DOCUMENTS

| CA | 2469699 | 1/2016 |
| CN | 1789992 | 6/2006 |

(Continued)

OTHER PUBLICATIONS

U.S. Appl. No. 16/036,456, filed Jul. 13, 2018, Ckristian Velez.

(Continued)

*Primary Examiner* — Andrew Joseph Rudy
(74) *Attorney, Agent, or Firm* — Fitch, Even, Tabin & Flannery, LLP

(57) ABSTRACT

Examples of the disclosure provide for an automated inspection system. The system includes an inspection component implemented on at least one computing device with at least one sensor configured to capture data about a good; and a communication component communicatively coupled to the computing device and configured to receive information regarding regulations and quality control standards associated with the good, and transmit the information regarding the acceptability of a good to an inventory system.

19 Claims, 8 Drawing Sheets

(56) References Cited

U.S. PATENT DOCUMENTS

| | | | |
|---|---|---|---|
| 5,835,012 A | 11/1998 | Wilk | |
| 6,204,763 B1 | 3/2001 | Sone | |
| 6,285,282 B1 | 9/2001 | Dorenbosch et al. | |
| 6,294,997 B1 | 9/2001 | Paratore et al. | |
| 6,296,187 B1 | 10/2001 | Shearer | |
| 6,386,454 B2 | 5/2002 | Hecht | |
| 6,435,002 B1 | 8/2002 | Briggs | |
| 6,497,367 B2 | 12/2002 | Conzola | |
| 6,549,135 B2 | 4/2003 | Singh | |
| 6,600,418 B2 | 7/2003 | Francis | |
| 6,624,752 B2 | 9/2003 | Klitsgaard | |
| 6,779,722 B1 | 8/2004 | Mason | |
| 6,847,447 B2 | 1/2005 | Ozanich | |
| 6,865,516 B1 | 3/2005 | Richardson | |
| 6,876,990 B2* | 4/2005 | Yamanishi | G06F 40/268 |
| | | | 706/45 |
| 6,965,871 B1 | 11/2005 | Szabo | |
| 6,970,100 B2 | 11/2005 | Lovegreen | |
| 6,982,640 B2 | 1/2006 | Lindsay | |
| 7,004,621 B2 | 2/2006 | Roberts | |
| 7,027,958 B2 | 4/2006 | Singh | |
| 7,057,495 B2 | 6/2006 | Debord | |
| 7,065,501 B1 | 6/2006 | Brown | |
| 7,148,803 B2 | 12/2006 | Bandy | |
| 7,185,810 B2 | 3/2007 | White | |
| 7,245,386 B2 | 7/2007 | Philipps | |
| 7,248,147 B2 | 7/2007 | Debord | |
| 7,271,720 B2 | 9/2007 | Tabe | |
| 7,271,724 B2 | 9/2007 | Goyal | |
| 7,298,257 B2 | 11/2007 | Suzuki | |
| 7,347,361 B2 | 3/2008 | Lovett | |
| 7,372,003 B2 | 5/2008 | Kates | |
| 7,434,724 B2 | 10/2008 | Lane | |
| 7,455,225 B1 | 11/2008 | Hadfield | |
| 7,487,913 B2 | 2/2009 | Adema | |
| 7,495,558 B2 | 2/2009 | Pope | |
| 7,543,741 B2 | 6/2009 | Lovett | |
| 7,560,013 B2 | 7/2009 | Shekarriz | |
| 7,673,464 B2 | 3/2010 | Bodin | |
| 7,675,424 B2 | 3/2010 | Debord | |
| 7,693,739 B2 | 4/2010 | Schmidtberg | |
| 7,757,947 B2 | 7/2010 | Reznik | |
| 7,775,130 B2 | 8/2010 | Harish | |
| 7,792,711 B2 | 9/2010 | Swafford, Jr. | |
| 7,796,038 B2 | 9/2010 | Batra | |
| 7,810,720 B2 | 10/2010 | Lovett | |
| 7,835,885 B2 | 11/2010 | Ben-Tzur | |
| 7,937,244 B2 | 5/2011 | Kadaba | |
| 7,954,712 B2 | 6/2011 | Babcock | |
| 7,960,176 B2 | 6/2011 | Louvet | |
| 7,978,060 B2 | 7/2011 | Mandava | |
| 8,072,605 B2 | 12/2011 | Costa | |
| 8,102,101 B2 | 1/2012 | Giurgiutiu | |
| 8,112,303 B2 | 2/2012 | Eglen | |
| 8,203,603 B2 | 6/2012 | Harbert | |
| 8,279,065 B2 | 10/2012 | Butler | |
| 8,306,871 B2 | 11/2012 | Farmer et al. | |
| 8,325,036 B1* | 12/2012 | Fuhr | G08B 13/19613 |
| | | | 340/540 |
| 8,334,970 B2 | 12/2012 | Wildenbeest | |
| 8,354,927 B2 | 1/2013 | Breed | |
| 8,412,590 B2 | 4/2013 | Elliott | |
| 8,447,665 B1 | 5/2013 | Schoenharl | |
| 8,682,760 B2 | 3/2014 | Cameo | |
| 8,786,407 B2 | 7/2014 | Liu | |
| 8,803,970 B2 | 8/2014 | Weisensale | |
| 8,870,453 B2 | 10/2014 | Branch | |
| 8,947,234 B2 | 2/2015 | Doan | |
| 8,994,508 B2 | 3/2015 | Dacus | |
| 9,024,755 B2 | 5/2015 | Fuhr | |
| 9,030,295 B2 | 5/2015 | Allen | |
| 9,031,990 B2 | 5/2015 | Scott | |
| 9,218,585 B2 | 12/2015 | Gupta | |
| 9,244,147 B1 | 1/2016 | Soundararajan | |
| 9,275,361 B2 | 3/2016 | Meyer | |
| 9,316,595 B2 | 4/2016 | Wakita | |
| 9,366,483 B2 | 6/2016 | Eckhoff | |
| 9,443,217 B2 | 9/2016 | Iyer | |
| 9,449,208 B2 | 9/2016 | Luk | |
| 9,514,323 B2 | 12/2016 | Mehring | |
| 9,557,224 B2 | 1/2017 | Eisenstadt | |
| 9,710,754 B2 | 7/2017 | Kaye | |
| 9,766,114 B2* | 9/2017 | Ademe | G01G 19/00 |
| 9,789,518 B2 | 10/2017 | Iino | |
| 9,811,632 B2 | 11/2017 | Grabiner | |
| 9,824,298 B1 | 11/2017 | Krishnan Gorumkonda | |
| 9,835,498 B2 | 12/2017 | Haarer | |
| 9,888,214 B2 | 2/2018 | Bateman | |
| 9,915,638 B2 | 3/2018 | Pakstaite | |
| 10,009,667 B2 | 6/2018 | Taylor | |
| 10,060,798 B1 | 8/2018 | Riscalla | |
| 10,176,451 B2 | 1/2019 | Nemet | |
| 10,187,593 B2* | 1/2019 | Holmes | A61J 1/03 |
| 10,281,200 B2* | 5/2019 | Johnston | G06T 7/13 |
| 10,285,433 B2* | 5/2019 | Ademe | A24C 5/343 |
| 10,324,439 B2* | 6/2019 | Lagares-Greenblatt | |
| | | | G05B 19/042 |
| 10,373,472 B2* | 8/2019 | Johnston | G01N 33/0063 |
| 10,386,827 B2* | 8/2019 | Enver | G05B 19/4184 |
| 10,423,918 B2 | 9/2019 | Mehring | |
| 10,445,684 B2 | 10/2019 | Mehring | |
| 10,466,111 B2 | 11/2019 | Jones et al. | |
| 10,546,162 B1* | 1/2020 | Diorio | G06K 7/10108 |
| 10,552,654 B2* | 2/2020 | Beckmann | G06K 7/10861 |
| 10,591,306 B2* | 3/2020 | High | H04W 4/35 |
| 10,594,956 B2* | 3/2020 | Holmes | G06K 9/2018 |
| 10,676,794 B2* | 6/2020 | Amini | G16B 50/00 |
| 10,956,856 B2* | 3/2021 | Ma | G06Q 10/087 |
| 2001/0045449 A1 | 11/2001 | Shannon | |
| 2002/0119513 A1 | 8/2002 | Alocilja | |
| 2003/0088442 A1 | 5/2003 | Michael | |
| 2003/0214387 A1 | 11/2003 | Giaccherini | |
| 2004/0018641 A1 | 1/2004 | Goldsmith | |
| 2004/0069046 A1 | 4/2004 | Sunshine | |
| 2004/0074957 A1 | 4/2004 | Devar | |
| 2004/0148117 A1 | 7/2004 | Kirshenbaum | |
| 2004/0154739 A1 | 8/2004 | Shanahan | |
| 2004/0204881 A1 | 10/2004 | Mayer | |
| 2004/0226392 A1 | 11/2004 | McNally | |
| 2005/0060246 A1 | 3/2005 | Lastinger | |
| 2005/0061877 A1 | 3/2005 | Stevens | |
| 2005/0104730 A1 | 5/2005 | Yang | |
| 2005/0149470 A1 | 7/2005 | Fujie | |
| 2005/0197912 A1 | 9/2005 | Wittmer | |
| 2005/0203790 A1 | 9/2005 | Cohen | |
| 2005/0222889 A1 | 10/2005 | Lai | |
| 2005/0228712 A1 | 10/2005 | Bornstein | |
| 2006/0006987 A1 | 1/2006 | Hashimoto | |
| 2006/0071774 A1 | 4/2006 | Brown | |
| 2006/0080819 A1 | 4/2006 | McAllister | |
| 2006/0097875 A1 | 5/2006 | Ott | |
| 2006/0238307 A1 | 10/2006 | Bauer | |
| 2006/0244718 A1 | 11/2006 | Hiddink | |
| 2007/0050070 A1 | 3/2007 | Strain et al. | |
| 2007/0050271 A1 | 3/2007 | Ufford | |
| 2007/0064765 A1 | 3/2007 | Solie | |
| 2007/0067177 A1 | 3/2007 | Martin | |
| 2007/0067203 A1 | 3/2007 | Gil | |
| 2007/0069867 A1 | 3/2007 | Fleisch | |
| 2007/0076779 A1 | 4/2007 | Haarer | |
| 2007/0156261 A1 | 7/2007 | Caldwell | |
| 2007/0176773 A1 | 8/2007 | Smolander | |
| 2007/0221727 A1 | 9/2007 | Reznik | |
| 2008/0001752 A1 | 1/2008 | Bruns | |
| 2008/0052201 A1 | 2/2008 | Bodin | |
| 2008/0067227 A1 | 3/2008 | Poss | |
| 2008/0073431 A1 | 3/2008 | Davis | |
| 2008/0103944 A1 | 5/2008 | Hagemann | |
| 2008/0186175 A1 | 8/2008 | Stern | |
| 2008/0292759 A1 | 11/2008 | Palmer | |
| 2008/0294488 A1 | 11/2008 | Gupta | |
| 2009/0027213 A1 | 1/2009 | Debord | |
| 2009/0040063 A1 | 2/2009 | Yearsley | |
| 2009/0058644 A1 | 3/2009 | French | |

(56) References Cited

U.S. PATENT DOCUMENTS

| | | |
|---|---|---|
| 2009/0076645 A1 | 3/2009 | Ben-Tzur |
| 2009/0083054 A1 | 3/2009 | Koo et al. |
| 2009/0119170 A1* | 5/2009 | Hammad ............ G06Q 20/32 705/14.17 |
| 2009/0144122 A1 | 6/2009 | Ginsberg |
| 2009/0261974 A1 | 10/2009 | Bailey |
| 2009/0322481 A1 | 12/2009 | Marr, III |
| 2010/0006646 A1 | 1/2010 | Stiller |
| 2010/0007464 A1 | 1/2010 | McTigue |
| 2010/0042369 A1 | 2/2010 | Mian et al. |
| 2010/0065632 A1 | 3/2010 | Babcock |
| 2010/0101317 A1 | 4/2010 | Ashrafzadeh |
| 2010/0138281 A1 | 6/2010 | Zhang |
| 2011/0029413 A1 | 2/2011 | Ben-Tzur |
| 2011/0035326 A1 | 2/2011 | Sholl |
| 2011/0068921 A1 | 3/2011 | Shafer |
| 2011/0301903 A1 | 12/2011 | Humbert |
| 2012/0101876 A1 | 4/2012 | Turvey |
| 2012/0161967 A1 | 6/2012 | Stern |
| 2012/0264446 A1 | 10/2012 | Xie |
| 2012/0267541 A1 | 10/2012 | Utukuri |
| 2012/0304014 A1 | 11/2012 | Prophete |
| 2012/0310853 A1 | 12/2012 | Aldstadt |
| 2013/0117053 A2 | 5/2013 | Campbell |
| 2013/0176115 A1 | 7/2013 | Puleston |
| 2013/0214797 A1 | 8/2013 | Gruden |
| 2013/0218511 A1 | 8/2013 | Mager |
| 2013/0235206 A1 | 9/2013 | Smith |
| 2013/0282522 A1 | 10/2013 | Hassan |
| 2014/0138440 A1 | 5/2014 | D'Ambrosio |
| 2014/0180953 A1 | 6/2014 | Westcott |
| 2014/0201041 A1 | 7/2014 | Meyer |
| 2014/0297487 A1 | 10/2014 | Bashkin |
| 2014/0313055 A1 | 10/2014 | Warkentin |
| 2014/0316875 A1 | 10/2014 | Tkachenko |
| 2014/0330407 A1 | 11/2014 | Corder |
| 2015/0015373 A1 | 1/2015 | Mongrenier |
| 2015/0021401 A1 | 1/2015 | Rajagopal |
| 2015/0022313 A1 | 1/2015 | Maier |
| 2015/0041616 A1 | 2/2015 | Gentile |
| 2015/0048938 A1 | 2/2015 | Tew |
| 2015/0084100 A1 | 3/2015 | Sablong |
| 2015/0186840 A1 | 7/2015 | Torres |
| 2015/0192475 A1 | 7/2015 | Eisenstadt |
| 2015/0338846 A1 | 11/2015 | Boivin |
| 2015/0347945 A1 | 12/2015 | Reese |
| 2016/0012337 A1 | 1/2016 | Kaye |
| 2016/0026032 A1 | 1/2016 | Moore |
| 2016/0034907 A1 | 2/2016 | Worrall |
| 2016/0048798 A1 | 2/2016 | Meyer |
| 2016/0063367 A1 | 3/2016 | Cai |
| 2016/0132821 A1 | 5/2016 | Glasgow |
| 2016/0189087 A1 | 6/2016 | Morton |
| 2016/0203591 A1* | 7/2016 | Justaniah ............ G06T 7/0004 348/89 |
| 2016/0217417 A1 | 7/2016 | Ma |
| 2016/0239794 A9 | 8/2016 | Shafer |
| 2016/0283904 A1 | 9/2016 | Siegel |
| 2016/0292634 A1 | 10/2016 | Mehring |
| 2016/0307040 A1 | 10/2016 | Shulman |
| 2016/0314514 A1 | 10/2016 | High |
| 2016/0350715 A1 | 12/2016 | Minvielle |
| 2017/0039194 A1 | 2/2017 | Tschetter |
| 2017/0039511 A1 | 2/2017 | Corona |
| 2017/0059391 A1 | 3/2017 | Ademe |
| 2017/0074921 A1 | 3/2017 | Uota |
| 2017/0102694 A1 | 4/2017 | Enver et al. |
| 2017/0116565 A1 | 4/2017 | Feiner |
| 2017/0122771 A1 | 5/2017 | Keal |
| 2017/0164773 A1 | 6/2017 | Wirtz |
| 2017/0255901 A1 | 9/2017 | Bermudez Rodriguez |
| 2017/0269601 A1 | 9/2017 | Jones |
| 2017/0286905 A1 | 10/2017 | Richardson |
| 2017/0300984 A1 | 10/2017 | Hurwich |
| 2017/0322090 A1 | 11/2017 | Jones |
| 2017/0344934 A1 | 11/2017 | Millhouse |
| 2017/0344935 A1 | 11/2017 | Mattingly |
| 2018/0007453 A1 | 1/2018 | Taylor |
| 2018/0045700 A1 | 2/2018 | Biermann |
| 2018/0078992 A1 | 3/2018 | High |
| 2018/0096175 A1 | 4/2018 | Schmeling |
| 2018/0143131 A1 | 5/2018 | Choi |
| 2018/0144430 A1 | 5/2018 | Millhouse |
| 2018/0180492 A1 | 6/2018 | Ribi |
| 2018/0195869 A1 | 7/2018 | High |
| 2018/0211208 A1* | 7/2018 | Winkle ............... H04L 67/12 |
| 2018/0217118 A1 | 8/2018 | Payne |
| 2018/0242768 A1 | 8/2018 | Lewis |
| 2018/0247257 A1* | 8/2018 | Lert, Jr. ............ G06Q 10/08 |
| 2018/0270631 A1 | 9/2018 | High |
| 2018/0279023 A1 | 9/2018 | Taylor |
| 2018/0290809 A1* | 10/2018 | Espinosa ........... B65D 81/2069 |
| 2018/0315011 A1* | 11/2018 | Clarke ............... G06Q 20/208 |
| 2019/0147396 A1 | 5/2019 | Bohling |
| 2019/0223643 A1 | 7/2019 | Hara |
| 2019/0285603 A1 | 9/2019 | Velez |
| 2020/0118072 A1 | 4/2020 | Johnson |

FOREIGN PATENT DOCUMENTS

| | | |
|---|---|---|
| CN | 201314907 | 9/2009 |
| CN | 202306566 | 7/2012 |
| CN | 102930649 | 2/2013 |
| CN | 203275285 | 11/2013 |
| CN | 203306566 | 11/2013 |
| CN | 103543703 | 1/2014 |
| CN | 103593746 | 2/2014 |
| CN | 104036354 | 9/2014 |
| CN | 204010264 | 12/2014 |
| CN | 104749329 | 7/2015 |
| CN | 204514846 | 7/2015 |
| CN | 105444504 | 3/2016 |
| CN | 106408173 | 2/2017 |
| CN | 106600286 | 4/2017 |
| CN | 107703269 | 2/2018 |
| EP | 1221613 | 7/2002 |
| EP | 1374688 | 1/2004 |
| EP | 2165298 | 3/2010 |
| EP | 2509412 | 10/2012 |
| EP | 2509412 A1 | 10/2012 |
| EP | 2835078 | 2/2015 |
| JP | 2002195971 A | 7/2002 |
| JP | 2008004133 | 1/2008 |
| JP | 2008004133 A | 1/2008 |
| JP | 2013068547 | 4/2013 |
| WO | 2000078919 A1 | 12/2000 |
| WO | 2001023256 | 4/2001 |
| WO | 2003098175 | 11/2003 |
| WO | 2007052208 A1 | 5/2007 |
| WO | 2008006152 A1 | 1/2008 |
| WO | 2012125960 | 9/2012 |
| WO | 2013174983 | 11/2013 |
| WO | 2014059048 | 4/2014 |
| WO | 2015061429 | 4/2015 |
| WO | 2015066594 | 5/2015 |

OTHER PUBLICATIONS

U.S. Appl. No. 16/112,974, filed Aug. 27, 2018, Joshua Bohling.

Bedard, Jean; "Temperature Mapping of Storage Areas"; Technical supplement to WHO Technical Report Series, No. 961, 2011; WHO Press, World Health Organization; available at least as early as Jan. 2014; pp. 1-25.

Eom, Ki-Hwan, et al.; "The Meat Freshness Monitoring System Using the Smart RFID Tag"; International Journal of Distributed Sensor Networks, vol. 2014; http://journals.sagepub.com/doi/10.1155/2014/591812; Jul. 9, 2014; pp. 1-10.

Greis, Noel P.; "Monitoring the 'Cool Chain' Maximizing Shelf Life for Safer Food"; https://atecentral.net/r20093/case_study_monitoring_the_cool_chain; National Science Foundation; published on Dec. 2011; pp. 1-9.

Jedermann, Reiner, et al.; "Semi-passive RFID and Beyond: Steps Towards Automated Quality Tracing in the Food Chain"; Inderscience

(56) References Cited

OTHER PUBLICATIONS

Enterprises Ltd.; Int. J. Radio Frequency Identification Technology and Applications, vol. 1, No. 3; published in 2007; pp. 247-259.
Moorthy, Rahul, et al.; "On-Shelf Availability in Retailing"; vol. 116—No. 23; International Journal of Computer Applications; available at least as early as Apr. 2015; pp. 47-51.
QC One; "Inspect. Report. Analyze. Quality Control Software for Fresh Produce"; http://qcone.com/en/; available at least as early as May 29, 2017; pp. 1-2.
Ryan, John M.; "Guide to Food Safety and Quality During Transportation: Controls, Standards and Practices"; Academic Press; available at least as early as 2014; pp. 1-8.
Yan, Lu, et al.; "The Internet of Things: From RFID to the Next-Generation Pervasive Networked Systems"; Auerbach Publications; New York; available at least as early as 2008; pp. 1-35.
Thomas, Shane, "International Search Report", International Application No. PCT/US2018/023201, dated May 31, 2018, 3 pages.
Thomas, Shane, "Written Opinion", International Application No. PCT/US2018/023201, dated May 31, 2018, 10 pages.
U.S. Appl. No. 16/526,677, filed Jul. 30, 2019, Bohling Joshua.
Arah, Isaac Kojo et al.; "Preharvest and Postharvest Factors Affecting the Quality and Shelf Life of Harvested Tomatoes: A Mini Review"; http://downloads.hindawi.com/journals/ija/2015/478041.pdf; Available as early as Oct. 14, 2015; pp. 1-7.
Badia, Ricardo; "Cold Chain Logistics: Assessing the Challenge"; https://www.zestlabs.com/assessing-cold-chain-logistics/; Mar. 19, 2019; pp. 1-4.
Barthe, J.F.; "D.2.3.2. Database of consumer awareness, expectations and concerns on cold chain"; http://www.frisbee-project.eu/images/result/FRISBEE_DEL_2-3-2.pdf; Dec. 2, 2011; pp. 1-26.
Barthe, J.F.; "D.2.3.2.1 Survey questionnaires and materials for studies of consumer perspectives and attitudes towards refrigerated foods, the cold chain and relevant refrigeration technologies (Informed consent forms, privacy, personal data handling)"; http://www.frisbee-project.eu/images/result/FRISBEE_DEL_2-3-2-1.pdf;Feb. 8, 2012; pp. 1-21.
Bevan et al.; "Storage of Organically Produced Crops"; https://orgprints.org/8241/1/Storage_organic_produce_report.pdf; Dec. 1997; pp. 1-227.
Bogataj, M., et al.; "Stability of perishable goods in cold logistic chains"; International Journal of Production Economics, vol. 93-94; 2005; pp. 345-356.
Capgemini; "Schuitema Revolutionizes Food Quality Control Through RFID"; https://www.capgemini.com/se-en/wp-content/uploads/sites/29/2017/07/Schuitema_Revolutionizes_Food_Quality_Control_Through_RFID.pdf; Jul. 29, 2017; pp. 1-2.
Chainlink Research; "Achieving Consistent Product Quality"; https://www.zestlabs.com/wp-content/uploads/2016/12/Quality-Management-For-Produ ce.pdf; Available as early as Dec. 2016; pp. 1-8.
Chainlink Research; "Measuring Produce Freshness: The Key to Preventing Waste"; https://www.zestlabs.com/wp-content/uploads/2016/03/Measuring-Produce-Freshness. pdf; Available as early as Mar. 2016; pp. 1-12.
Chainlink Research; "Preemptive Freshness Management"; https://www.zestlabs.com/wp-content/uploads/2017/03/Preemptive-Freshness-Managem ent.pdf; Available as early as Mar. 2017; pp. 1-8.
Chainlink Research; "Blockchain's Role in the Produce Supply Chain"; https://www.zestlabs.com/wp-content/uploads/2018/01/Blockchains-Role-in-the-Prod uce-Supply-Chain.pdf; Available as early as Jan. 2018; pp. 1-20.
Chainlink Research; "Pallet-level Monitoring"; https://www.zestlabs.com/wp-content/uploads/2016/03/Pallet-Monitoring-for-the-Fr esh-Food-Supply-Chain.pdf; Available as early as Mar. 2016; pp. 1-9.
Chainlink Research; "Why Quality Consistency Matters"; https://www.zestlabs.com/wp-content/uploads/2016/03/Why-Food-Supply-Chain-Qualit y-Matters-1.pdf; Available as early as Mar. 2016; pp. 1-10.
Claussen, Ingrid C.; "Deliverable D.3.2.4.3 Literature review and experimental data of chilled, superchilled/supercooled fish quality and safety models"; http://www.frisbee-project.eu/images/result/FRISBEE_DEL_3-2-4-3.pdf; May 6, 2011; pp. 1-29.
Colmer, Christian; "Chill—ON! Transparent food quality all the way"; https://www.innovations-report.com/html/reports/medicine-health/chill-transparen t-food-quality-168201.html; Oct. 1, 2011; pp. 1-5.
Cotillon, C.; "Deliverable 8.2.1.1 Publication in Scientific Journals"; http://www.frisbee-project.eu/images/result/FRISBEE_DEL_8.2.1.1.pdf; Oct. 27, 2011; pp. 1-5.
Cotillon, C.; "Deliverable 8.3.3.1 Mini conferences"; http://www.frisbee-project.eu/images/result/FRISBEE_DEL_8.3.3.1.pdf; Dec. 7, 2011; pp. 1-8.
Cotillon, C.; "Deliverable 8.6.1 Report on collaboration with other EU projects"; http://www.frisbee-project.eu/images/result/FRISBEE_DEL_8.6.1.pdf; Dec. 5, 2011; pp. 1-12.
Dada, Ali, et al.; "Sensor Applications in the Supply Chain: The Example of Quality-Based Issuing of Perishables"; The Internet of Things. Lecture Notes in Computer Science, edited by Christian Floerkemeier, et al.; vol. 4952; 2008; pp. 140-154.
Desmedt, Frederique; "Deliverable 8.1.1 Project logo, Leaflet and PowerPoint presentation"; http://www.frisbee-project.eu/images/result/FRISBEE_DEL_8.1.1.pdf; Nov. 19, 2010; pp. 1-30.
Desmedt, Frederique; "Deliverable 8.1.2 Project internet and intranet website"; http://www.frisbee-project.eu/images/result/FRISBEE_DEL_8.1.2.pdf; Mar. 3, 2011; pp. 1-9.
Do Nascimento Nunes, M. C., et al.; "Improvement in fresh fruit and vegetable logistics quality: berry logistics field studies"; Philosophical Transactions of the Royal Society; http://dx.doi.org/10.1098/rsta.2013.0307; 2014; pp. 1-19.
Doyle, John P.; "Seafood Shelf Life as a Function of Temperature"; Alaska Sea Grant Marine Advisory Program; No. 30; 1989; pp. 1-6.
Evans, J.; "Deliverable D2.2.2 : Assessment of current refrigeration technologies of selected food industries and their potential improvement in current refrigeration"; http://www.frisbee-project.eu/images/result/FRISBEE_DEL_2-2-2.pdf; Jan. 30, 2012; pp. 1-181.
Evans, Judith et al.; "Deliverable D.2.2.3 : Analysis of potential of novel refrigeration technologies suitable for selected industries for application and improvement of food quality, energy consumption and environmental impact"; http://www.frisbee-project.eu/images/result/FRISBEE_DEL_2-2-3.pdf; Dec. 2, 2011; pp. 1-54.
Friedlos, Dave; "New Zealand Kiwifruit Processor Finds ROI"; https://www.rfidjournal.com/articles/view?4090; May 20, 2008; pp. 1-4.
Frisbee; "Frisbee european project—Archive"; https://web.archive.org/web/20180815100417/http://www.frisbee-project.eu/archive -results.html; Available as early as Aug. 15, 2018; pp. 1-5.
Frisbee; "Frisbee european project—Developing novel breakthrough technologies"; https://web.archive.org/web/20180316101206/http://www.frisbee-project.eu/researc h/92-developing-novel-breakthrough-technologies.html; Available as early Mar. 16, 2018; pp. 1-3.
Frisbee; "Frisbee european project—Frisbee at the Sixteenth Conference on Food Microbiology, Belgium"; http://www.frisbee-project.eu/news/40-frisbee-at-the-sixteenth-conference-on-foo d-microbiology.html; Nov. 15, 2011; pp. 1-1.
Frisbee; "Frisbee european project—Frisbee develops a Virtual Platform application"; http://www.frisbee-project.eu/news/90-frisbee-develops-a-virtual-platform-applic ation.html; Mar. 18, 2013; pp. 1-1.
Frisbee; "Frisbee european project—Frisbee dissemination activities"; http://www.frisbee-project.eu/news/91-frisbee-dissemination-activities.html; Mar. 18, 2013; pp. 1-1.
Frisbee; "Frisbee european project—Frisbee on the starting-blocks"; http://www.frisbee-project.eu/news/49-frisbee-on-the-starting-blocks.html; Mar. 9, 2012; pp. 1-2.
Frisbee; "Frisbee european project—Frisbee welcomes New Members Advisory Board"; http://www.frisbee-project.eu/news/48-new-members-advisory-board.html; Mar. 9, 2012; pp. 1-1.
Frisbee; "Frisbee european project—Frisbee: Latest Developments"; http://www.frisbee-project.eu/news/42-frisbee-project-latest-developments.html; Dec. 21, 2011; pp. 1-2.

(56) References Cited

OTHER PUBLICATIONS

Frisbee; "Frisbee european project—Join the first European Food Cold Chain Database!!!";http://www.frisbee-project.eu/news/55-database2.html; Jul. 9, 2012; pp. 1-2.
Frisbee; "Frisbee european project—Magnetic refrigeration technology. Frisbee's experts team work on this disruptive technology"; https://web.archive.org/web/20180316101206/http://www.frisbee-project.eu/researc h/51-magnetic-refrigeration-technology.html; Available as early as Mar. 16, 2018; pp. 1-3.
Frisbee; "Frisbee european project—MEP-scientist pairing scheme"; http://www.frisbee-project.eu/news/41-mep-scientist-pairing-scheme.html; Dec. 20, 2011; pp. 1-2.
Frisbee; "Frisbee european project—Nanoparticles, a concentrate of energy: PCM nanoparticles where low temperatures are needed"; https://web.archive.org/web/20180316101206/http://www.frisbee-project.eu/researc h/27-nanoparticles-a-concentrate-of-energy.html; Available as early as Mar. 16, 2018; pp. 1-2.
Frisbee; "Frisbee european project—Project Overview"; https://web.archive.org/web/20120211082956/http://www.frisbee-project.eu/project -overview.html; Available as early as Feb. 11, 2012; pp. 1-1.
Frisbee; "Frisbee european project—Saving energy by refrigeration predictive control"; https://web.archive.org/web/20180316101206/http://www.frisbee-project.eu/researc h/52-saving-energy-by-refrigeration-predictive-control.html; Available as early as Mar. 16, 2018; pp. 1-3.
Frisbee; "Frisbee european project—Superchilling! A new technology to have your food products fresher than fresh"; https://web.archive.org/web/20180316101206/http://www.frisbee-project.eu/researc h/50-superchilling.html; Available as early as Mar. 16, 2018; pp. 1-3.
Frisbee; "Frisbee european project—Taking Europe's temperature: Cold chain database"; http://www.frisbee-project.eu/news/89-taking-europe%E2%80%99s-temperature-cold-c hain-database.html; Mar. 18, 2013; pp. 1-2.
Frisbee; "Frisbee european project—Workpackages"; https://web.archive.org/web/20120210124516/http://www.frisbee-project.eu/workpac kages.html; Available as early as Feb. 10, 2012; pp. 1-2.
Frisbee; "Simulate a cold chain"; https://frisbee-etool.irstea.fr; Available as early as 2020; pp. 1-3.
Gapud, Veny; "Food Safety Trends Exploring Implications of Mandatory Safety Standards in Retail and Foodservice"; https://www.foodsafetymagazine.com/magazine-archive1/december-2009january-2010/f ood-safety-trends-exploring-implications-of-mandatory-safety-standards-in-retail -and-foodservice/; Dec. 12, 2019; pp. 1-20.
Gaukler, Gary et al.; "Establishing Dynamic Expiration Dates for Perishables: An Application of RFID and Sensor Technology"; International Journal of Production Economics; vol. 193; Jul. 25, 2017; pp. 617-632.
GEIE/CEMA/ITP; "Deliverable D 8.3.1.3 Newsletter edited by GEIE for industrial use N°3"; http://www.frisbee-project.eu/images/result/FRISBEE_DEL_8.3.1.3.pdf; Mar. 13, 2012; pp. 1-10.
GEIE/CEMA/ITP; "Deliverable D8.3.1.2 Newsletter edited by GEIE for industrial use N°2"; http://www.frisbee-project.eu/images/result/FRISBEE_DEL_8.3.1.2.pdf; Oct. 27, 2011; pp. 1-10.
Giannakourou, M. C., et al.; "Application of a TTI-Based Distribution Management System for Quality Optimization of Frozen Vegetables at the Consumer End"; Journal of Food Science, vol. 68, Issue 1; Jan. 2003; pp. 201-209.
Hertog, M. L. A. T. M., et al.; "Shelf-life modelling for first-expired-first-out warehouse management"; Philosophical Transactions of the Royal Society; http://dx.doi.org/10.1098/rsta.2013.0306; 2014; pp. 1-15.
IBM; "DHL Breaks New Ground with RFID-Based Real-Time Tracking of Sensitive Shipments"; ftp://ftp.software.ibm.com/software/solutions/pdfs/ODC00298-USEN-00.pdf; Available as early as Mar. 2007; pp. 1-4.
IBM; "Focus on Food Safety"; https://www.ibm.com/downloads/cas/ZN9EWKRQ; Available at least as early as 2018; pp. 1-2.
Infratab; "Infratab Freshtime RF Sensor Blockchain Solutions for the Fresh Seafood Cold Chain"; https://web.aimglobal.org/external/wcpages/wcecommerce/eComItemDetailsPage.aspx?ItemID=656; 2019; pp. 1-5.
Jedermann, Reiner, et al.; "Communication techniques and challenges for wireless food quality monitoring"; Philosophical Transactions of the Royal Society; http://dx.doi.org/10.1098/rsta.2013.0304; 2014; pp. 1-18.
Jedermann, Reiner, et al.; "Reducing food losses by intelligent food logistics"; Philosophical Transactions of the Royal Society; http://dx.doi.org/10.1098/rsta.2013.0302; 2014; pp. 1-20.
Kader, A. A.; "Pre- and Postharvest Factors Affecting Fresh Produce Quality, Nutritional Value, and Implications for Human Health"; Proceedings of the International Congress of Food Production and the Quality of Life, Sassari (Italy) Sep. 4-8, 2000, vol. 1, pp. 109-119.
Ketzenberg, M., et al.; "Expiration Dates and Order Quantities for Perishables"; European Journal of Operational Research; vol. 266, Issue 2; Apr. 2018; pp. 569-584.
Ketzenberg, M., et al.; "Managing Perishables with Time and Temperature History"; Production and Operations Management; vol. 24, Issue 1; Jan. 2015; pp. 54-70.
Ketzenberg, M., et al.; "The Value of RFID Technology Enabled Information to Manage Perishables"; https://pdfs.semanticscholar.org/bded/16af2e689b4fdcea7f8421f6e012a6041324.pdf; Apr. 2009; pp. 1-37.
Koutsoumanis, K., et al.; "Development of a safety monitoring and assurance system for chilled food product"; International Journal of Food Microbiology, vol. 100; 2005; pp. 253-260.
Leake, Linda L.; "The Search for Shelf Life Solutions"; https://www.ift.org/news-and-publications/food-technology-magazine/issues/2007/n ovember/columns/laboratory?page=viewall; Nov. 1, 2007; pp. 1-8.
McBeath, Bill; "Winning the Freshness Wars: Creating Shopper Loyalty and Improving Profitability in Retail Grocery"; https://www.zestlabs.com/wp-content/uploads/2016/11/ZL_WP_FreshnessWars_060415.p df; Available as early as Feb. 2013; pp. 1-16.
Mehring, Peter; "Blockchain for Food Safety—Addressing the Challenges"; https://www.zestlabs.com/will-blockchain-solve-food-safety-challenges/; Sep. 26, 2018; pp. 1-4.
Mehring, Peter; "Zest Labs CEO Peter Mehring on the Walmart Lawsuit"; https://www.zestlabs.com/zest-labs-ceo-peter-mehring-walmart-lawsuit/; Aug. 1, 2018; pp. 1-4.
Mitrokotsa et al.; "Integrated RFID and Sensor Networks: Architectures and Applications"; https://pdfs.semanticscholar.org/e5b0/c2a44971bad209cbf66afb6c825f89792723.pdf; Jun. 22, 2009; pp. 511-536.
NBC Bay Area; "Tech Company Helps Inspect Food During Shutdown"; https://www.nbcbayarea.com/news/tech/tech-company-helps-inspect-food-during-shut down_bay-area/4851; Jan. 11, 2019; pp. 1-6.
NRDC; "Wasted: How America is Losing up to 40 Percent of Its Food From Farm to Fork Landfill"; https://www.nrdc.org/sites/default/files/wasted-2017-report.pdf; Available as early as Aug. 2017; pp. 1-58.
Opatova, H.; "Deliverable 8.2.2.1 Organisation of a Workshop in Prague 2011 at International Congress of Refrigeration"; http://www.frisbee-project.eu/images/result/FRISBEE_DEL_8.2.2.1.pdf; Oct. 27, 2011; pp. 1-8.
Payne, Kevin; "New Verizon Ad Sheds Light on Important Food Safety Issues"; https://www.zestlabs.com/new-verizon-ad-sheds-light-on-important-food-safety-iss ues/; Dec. 15, 2017; pp. 1-4.
Payne, Kevin; "Agriculture Technology and "The Messy Middle""; https://www.zestlabs.com/agriculture-technology-messy-middle/; Jun. 25, 2019; pp. 1-4.
Payne, Kevin; "Are You Ready to Make 2018 Your Best Year Ever?" https://www.zestlabs.com/are-you-ready-to-make-2018-your-best-year-ever/; Feb. 13, 2018; pp. 1-4.
Payne, Kevin; "Blockchain for Fresh Food Supply Chains—Reality Sets In?"; https://www.zestlabs.com/blockchain-fresh-supply-chains-reality/; May 7, 2019; pp. 1-4.

(56) References Cited

OTHER PUBLICATIONS

Payne, Kevin; "Cold Chain Visibility: Who's Winning the Freshness Wars?"; https://www.zestlabs.com/cold-chain-visibility-freshness-wars/; Apr. 9, 2019; pp. 1-4.
Payne, Kevin; "Cold Supply Chain Variability—The Impact of Delays"; https://www.zestlabs.com/cold-supply-chain-variability/; Apr. 23, 2019; pp. 1-4.
Payne, Kevin; "Earth Day 2019 and Looking Ahead to 2020"; https://www.zestlabs.com/earth-day-2019/; Apr. 30, 2019; pp. 1-4.
Payne, Kevin; "Finding the Right Tools: Can Blockchain and IOT Fix the Fresh Food Supply Chain?—Register for the Webinar"; https://www.zestlabs.com/finding-the-right-tools-can-blockchain-and-iot-fix-the- fresh-food-supply-chain-register-for-the-webinar/; Feb. 27, 2018; pp. 1-4.
Payne, Kevin; "Food Grower and Supplier Challenges: The Top 10"; https://www.zestlabs.com/food-growers-suppliers-challenges/; Feb. 19, 2019; pp. 1-4.
Payne, Kevin; "Food Labels and Food Waste—A Solution"; https://www.zestlabs.com/food-labels-food-waste/; Mar. 12, 2019; pp. 1-4.
Payne, Kevin; "Food Safety Tips: Three Things to Consider"; https://www.zestlabs.com/food-safety-tips-three-things-to-consider/; Jul. 2, 2019; pp. 1-4.
Payne, Kevin; "Fresh Produce and Health: What's the Connection?"; https://www.zestlabs.com/fresh-produce-health-interrelationship/; Apr. 2, 2019; pp. 1-4.
Payne, Kevin; "Grocery Shopper Trends 2019: Key Insights"; https://www.zestlabs.com/grocery-shopper-trends-2019-key-insights/; Jul. 23, 2019; pp. 1-4.
Payne, Kevin; "How to Feed a Hungry Planet: Food for Thought"; https://www.zestlabs.com/feed-a-hungry-planet/; Aug. 6, 2019; pp. 1-4.
Payne, Kevin; "Hyped Up? Blockchain and Why a Hybrid Model is Best"; https://www.zestlabs.com/hyped-up-blockchain-the-fresh-food-supply-chain-and-why -a-hybrid-model-is-best/; Jan. 30, 2018; pp. 1-4.
Payne, Kevin; "I'll Never Look at Strawberries the Same Way"; https://www.zestlabs.com/ill-never-look-at-strawberries-the-same-way/; Dec. 15, 2017; pp. 1-4.
Payne, Kevin; "Improving Operational Efficiency: TQM for the Fresh Food Supply Chain"; https://www.zestlabs.com/improving-operational-efficiency-deming-drucker/; Aug. 27, 2019; pp. 1-4.
Payne, Kevin; "Increasing Trucking Costs Further Squeezes Grocery Margins—Don't Waste Your Money!" https://www.zestlabs.com/increasing-trucking-costs-further-squeezes-grocery-marg ins-dont-waste-your-money/; Feb. 6, 2018; pp. 1-4.
Payne, Kevin; "IoT Sensors and Reducing Food Waste"; https://www.zestlabs.com/iot-sensors-reduce-food-waste/; Feb. 12, 2019; pp. 1-4.
Payne, Kevin; "Millennials Want True Transperency"; https://www.zestlabs.com/millennials-want-true-transparency/; Jan. 9, 2018; pp. 1-4.
Payne, Kevin; "Myth Busting: Produce Shrink is Caused at the Store"; https://www.zestlabs.com/myth-busting-produce-shrink-occurs-at-the-store/; Feb. 20, 2018; pp. 1-4.
Payne, Kevin; "New Zest Fresh for Produce Modules: Rapid Implementations and Faster ROI"; https://www.zestlabs.com/zest-fresh-produce-modules/; Jul. 10, 2019; pp. 1-4.
Payne, Kevin; "Online Grocery Shopping Options Abound But . . . "; https://www.zestlabs.com/online-grocery-shopping/; Feb. 5, 2019; pp. 1-4.
Payne, Kevin; "Preventing Food Waste: Multiple Approaches"; https://www.zestlabs.com/preventing-food-waste-multiple-approaches/; Jul. 16, 2019; pp. 1-4.
Payne, Kevin; "Proactive Food Safety: Moving the Industry Forward"; https://www.zestlabs.com/proactive-food-safety/; Aug. 13, 2019; pp. 1-4.
Payne, Kevin; "Produce Marketing: Brandstorm Offers a Wealth of Insights"; https://www.zestlabs.com/produce-marketing-ideas/; Feb. 26, 2019; pp. 1-4.

Payne, Kevin; "Reducing Fresh Food Waste: Addressing the Problem"; https://www.zestlabs.com/reducing-fresh-food-waste-problem/; Mar. 5, 2019; pp. 1-4.
Payne, Kevin; "Rethinking Food Safety and the Supply Chain"; https://www.zestlabs.com/rethinking-food-safety-supply-chain/; May 14, 2019; pp. 1-5.
Payne, Kevin; "Salad Kits: How to Ensure Freshness"; https://www.zestlabs.com/salad-kits-fresh/; Apr. 16, 2019; pp. 1-4.
Payne, Kevin; "Shelf-life Variability at Grocery Stores: Half-bad is Not Good"; https://www.zestlabs.com/shelf-life-variability-among-leading-grocery-stores/; Jun. 10, 2019; pp. 1-4.
Payne, Kevin; "Start the Year Fresh!" https://www.zestlabs.com/start-the-year-fresh/; Jan. 16, 2018; pp. 1-4.
Payne, Kevin; "Supply Chain Waste: Can We Fix the Problem? (Yes)"; https://www.zestlabs.com/supply-chain-waste/; Jul. 30, 2019; pp. 1-5.
Payne, Kevin; "Sustainability and the Supply Chain"; https://www.zestlabs.com/sustainability-supply-chain/; Jun. 18, 2019; pp. 1-4.
Payne, Kevin; "Sustainability or Greenwashing" https://www.zestlabs.com/sustainability-or-greenwashing/; Jan. 23, 2018; pp. 1-4.
Payne, Kevin; "The "Best If Used by" Date Label: Will It Reduce Food Waste?"; https://www.zestlabs.com/best-if-used-by-date-label/; Jun. 4, 2019; pp. 1-4.
Payne, Kevin; "The Emergence of Brand Marketing in Produce"; https://www.zestlabs.com/brand-marketing-produce/; Aug. 20, 2019; pp. 1-4.
Payne, Kevin; "The Grocery Shopping Experience: Fresh Foods, Fresh Ideas"; https://www.zestlabs.com/grocery-shopping-experience-fresh-foods/; May 21, 2019; pp. 1-4.
Payne, Kevin; "To Use or Not to Use—What's Up With Date Labels" https://www.zestlabs.com/date-label/; Jan. 2, 2018; pp. 1-4.
Payne, Kevin; "Want to Improve Your Grocery Margins? Take a Look at Your Supply Chain"; https://www.zestlabs.com/want-to-improve-your-grocery-margins-take-a-look-at-you r-supply-chain/; Dec. 19, 2017; pp. 1-4.
Payne, Kevin; "World Hunger Day 2019: Sustainability"; https://www.zestlabs.com/world-hunger-day-2019-sustainability/; May 28, 2019; pp. 1-4.
Payne, Kevin; "Your Technology Roadmap for Digital Transformation"; https://www.zestlabs.com/technology-roadmap/; Mar. 26, 2019; pp. 1-4.
Payne, Kevin; "A Picture Is Worth . . . "; https://www.zestlabs.com/a-picture-is-worth/; Apr. 3, 2018; pp. 1-4.
Payne, Kevin; "Before and After—The Benefits of Digital Transformation"; https://www.zestlabs.com/benefits-digital-transformation/; Jan. 29, 2019; pp. 1-5.
Payne, Kevin; "Being Proactive: What We Can Learn from Football"; https://www.zestlabs.com/being-proactive-learn-from-football/; Jul. 17, 2018; pp. 1-4.
Payne, Kevin; "Digital Transformation Technology: Is It Finally Time?"; https://www.zestlabs.com/digital-transformation-technology/; Aug. 7, 2018; pp. 1-4.
Payne, Kevin; "Experience the Many Benefits of Family Meals"; https://www.zestlabs.com/benefits-family-meals/; Sep. 3, 2019; pp. 1-4.
Payne, Kevin; "First Principles Thinking and the Fresh Food Supply Chain"; https://www.zestlabs.com/first-principles-thinking/; Oct. 2, 2018; pp. 1-4.
Payne, Kevin; "Five Days? The Causes of Shelf-life Variability"; https://www.zestlabs.com/five-days-shelf-life-variability/; Nov. 20, 2018; pp. 1-4.
Payne, Kevin; "Food Service Delivery: This Isn't What I Ordered!"; https://www.zestlabs.com/isnt-what-ordered/; Aug. 28, 2018; pp. 1-4.
Payne, Kevin; "Food Spoilage: The Impact on Your Business"; https://www.zestlabs.com/food-spoilage-impact-business/; Jan. 15, 2019; pp. 1-4.
Payne, Kevin; "Food Sustainability Goals: Noble But Are They Viable?"; https://www.zestlabs.com/food-sustainability-goals/; Aug. 14, 2018; pp. 1-4.
Payne, Kevin; "Fresh Food Industry Trends 2019—Our Predictions"; https://www.zestlabs.com/fresh-food-industry-trends-2019/; Jan. 2, 2019; pp. 1-4.

(56) References Cited

OTHER PUBLICATIONS

Payne, Kevin; "Fresh Food Industry Trends from 2018"; https://www.zestlabs.com/fresh-food-industry-trends-2018/; Dec. 11, 2018; pp. 1-4.
Payne, Kevin; "Fresh Food Sustainability—It's More Than Field to Fork"; https://www.zestlabs.com/fresh-food-sustainability/; Jan. 22, 2019; pp. 1-4.
Payne, Kevin; "Freshness Capacity: Strawberries Are Like Your Cell Phone . . . "; https://www.zestlabs.com/your-fresh-strawberries-are-like-your-cellphone/; Jul. 10, 2018; pp. 1-4.
Payne, Kevin; "Grocers Are Applying Artificial Intelligence"; https://www.zestlabs.com/grocers-turning-artificial-intelligence/; Oct. 9, 2018; pp. 1-4.
Payne, Kevin; "Growers and Suppliers—What Really Happens in the Food Supply Chain"; https://www.zestlabs.com/what-happens-fresh-food-supply-chain/; Apr. 24, 2018; pp. 1-5.
Payne, Kevin; "Improving Post-Harvest Operational Efficiency"; https://www.zestlabs.com/improving-operational-efficiency/; Sep. 18, 2018; pp. 1-4.
Payne, Kevin; "Is Your Fresh Food Supply Chain Stuck in the '60s?"; https://www.zestlabs.com/is-your-fresh-food-supply-chain-stuck-in-the-60s/; Mar. 13, 2018; pp. 1-4.
Payne, Kevin; "It's (Past) Time for Freshness Management"; https://www.zestlabs.com/managing-fresh-food-shelf-life/; Nov. 27, 2018; pp. 1-4.
Payne, Kevin; "It's Like Waze for the Fresh Food Supply Chain"; https://www.zestlabs.com/waze-fresh-food-supply-chain/; Apr. 10, 2018; pp. 1-5.
Payne, Kevin; "Let's Celebrate National Salad Month!"; https://www.zestlabs.com/lets-celebrate-national-salad-month/; May 1, 2018; pp. 1-4.
Payne, Kevin; "Let's Start At the Beginning"; https://www.zestlabs.com/lets-start-at-the-beginning/; May 15, 2018; pp. 1-4.
Payne, Kevin; "Margins Matter—Don't Get Squeezed"; https://www.zestlabs.com/6931-2/; Apr. 17, 2018; pp. 1-4.
Payne, Kevin; "Perishable Food Waste Cuts Profits & Raises Greenhouse Gases"; https://www.zestlabs.com/food-waste-profits-greenhouse-gases/; Sep. 11, 2018; pp. 1-4.
Payne, Kevin; "PMA Fresh Summit 2018—Wow!"; https://www.zestlabs.com/pma-fresh-summit/; Oct. 23, 2018; pp. 1-4.
Payne, Kevin; "PMA's Fresh Summit: Eat Up!"; https://www.zestlabs.com/pma-fresh-summit-2018/; Oct. 16, 2018; pp. 1-4.
Payne, Kevin; "Poor Quality Produce: Never Going Back Again"; https://www.zestlabs.com/never-going-back-again/; Jul. 3, 2018; pp. 1-4.
Payne, Kevin; "Premature Food Spoilage: Uh Oh, It's the Fuzz!"; https://www.zestlabs.com/uh-oh-its-the-fuzz/; Jun. 19, 2018; pp. 1-4.
Payne, Kevin; "Produce Shelf Life Extenders and Fresh Food Waste"; https://www.zestlabs.com/shelf-life-extenders-food-waste/; Nov. 13, 2018; pp. 1-4.
Payne, Kevin; "Refed: Committed to Reducing U.S. Food Waste"; https://www.zestlabs.com/refed-committed-reducing-waste/; Oct. 30, 2018; pp. 1-4.
Payne, Kevin; "Romaine Lettuce Labeling—Zest Fresh Can Help"; https://www.zestlabs.com/romaine-lettuce-labeling/; Dec. 4, 2018; pp. 1-4.
Payne, Kevin; "Saving Money Day 1—Invest $1, Get $9 Back"; https://www.zestlabs.com/saving-money-day-1/; Nov. 6, 2018; pp. 1-4.
Payne, Kevin; "September Is National Family Meals Month"; https://www.zestlabs.com/september-family-meals-month/; Sep. 4, 2018; pp. 1-4.
Payne, Kevin; "Shelf-life Variability in Produce: The Five Causes"; https://www.zestlabs.com/shelf-life-variability-produce-five-causes/; Jan. 8, 2019; pp. 1-4.
Payne, Kevin; "Solving the Problem of Fresh Produce Waste"; https://www.zestlabs.com/solving-problem-fresh-food-waste/; Dec. 18, 2018; pp. 1-4.
Payne, Kevin; "Stay Cool! (And Visit Us at United Fresh!)"; https://www.zestlabs.com/stay-cool-and-visit-us-at-united-fresh/; Jun. 5, 2018; pp. 1-4.
Payne, Kevin; "Stop Doing That!"; https://www.zestlabs.com/stop-doing-that/; May 29, 2018; pp. 1-4.
Payne, Kevin; "Supply Chain Performance: The Fox and the Henhouse"; https://www.zestlabs.com/fox-hen-house/; Jun. 26, 2018; pp. 1-4.
Payne, Kevin; "The Fresh Food Industry and Charles Darwin"; https://www.zestlabs.com/charles-darwin-fresh-food-industry/; Aug. 21, 2018; pp. 1-4.
Payne, Kevin; "The Game of (Shelf) Life"; https://www.zestlabs.com/game-shelf-life/; Sep. 25, 2018; pp. 1-4.
Payne, Kevin; "Timing Is Everything—The Impact of Cut-To-Cool Time on Freshness"; https://www.zestlabs.com/timing-is-everything-the-impact-of-cut-to-cool-time-on- freshness/; May 8, 2018; pp. 1-5.
Payne, Kevin; "What to do to Build Grocery Store Loyalty?"; https://www.zestlabs.com/grocery-store-loyalty/; Jul. 24, 2018; pp. 1-4.
Payne, Kevin; "What? No Bacon? (Cue Ominous Music)"; https://www.zestlabs.com/what-no-bacon-cue-ominous-music/; Mar. 6, 2018; pp. 1-5.
Payne, Kevin; "What's in the Bag?"; https://www.zestlabs.com/whats-in-the-bag/; May 22, 2018; pp. 1-4.
Payne, Kevin; "Where's the Beef (Been)?"; https://www.zestlabs.com/wheres-the-beef-been/; Mar. 27, 2018; pp. 1-5.
Payne, Kevin; "Zest Labs Offers Fresh Wishes for the New Year"; https://www.zestlabs.com/zest-labs-fresh-wishes-new-year/; Dec. 24, 2018; pp. 1-4.
ReFED; "A Roadmap to Reduce U.S. Food Waste by 20 Percent"; https://www.refed.com/downloads/ReFED_Report_2016.pdf; 2016; pp. 1-96.
ReFED; "Restaurant Food Waste Action Guide"; https://www.refed.com/downloads/Restaurant_Guide_Web.pdf; 2018; pp. 1-44.
ReFED; "Retail Food Waste Action Guide"; https://www.refed.com/downloads/Retail_Guide_Web.pdf; 2018; pp. 1-44.
Ruiz-Garcia, Luis et al.; "Monitoring Cold Chain Logistics by Means of RFID"; http://cdn.intechweb.org/pdfs/8493.pdf; Feb. 1, 2010; pp. 1-16.
Ryan, John; "Why Blockchain Will Be Used to Improve Distribution Food Safety, Quality, and Traceability"; https://www.foodsafetymagazine.com/enewsletter/why-blockchain-will-be-used-to-improve-distribution-food-safety-quality-and-traceability/; Feb. 5, 2019; pp. 1-3.
Scalco, Dan; "5 Ways to Ensure Meals Stay Fresh and Safe in Transit"; https://www.zestlabs.com/meals-stay-fresh-safe-transit/; Jun. 12, 2018; pp. 1-4.
Scotto Di Tella, F.; "Deliverable D8.3.1.1 Newsletter edited by GEIE for industrial use N°1"; http://www.frisbee-project.eu/images/result/FRISBEE_DEL_8.3.1.1.pdf; May 6, 2011; pp. 1-9.
Shacklett, Mary; "Customer Retention and Growth in Today's Competitive Retail Grocery Environment"; https://www.zestlabs.com/downloads/Food-Freshness-and-Customer-Satisfaction-Transworld-Research-April-2019.pdf; Apr. 2019; pp. 1-7.
Shacklett, Mary; "Improving Profits and Operational Efficiency on the Farm"; https://www.zestlabs.com/downloads/Improving-Operational-Efficiency-on-the-Farm- Transworld-Research-2018.pdf; Available as early as 2018; pp. 1-6.
Shacklett, Mary; "Optimizing Profit Margins in a Changing Retail Grocery Industry"; https://www.zestlabs.com/downloads/Optimizing-Profit-Margins-Transworld.pdf; 2018; pp. 1-10.
Siawsolit, Chokdee et al.; "The Value of Demand Information in Omni-Channel Grocery Retailing"; https://www.researchgate.net/publication/331048136_The_Value_of_Demand_Information_in_Omni-Channel_Grocery_Retailing; Available as early as Jan. 2019; pp. 1-11.
Stahl, Valerie et al.; "Deliverable D.3.2.4.2 Literature review and experimental data of chilled and frozen meat quality and safety models"; http://www.frisbee-project.eu/images/result/FRISBEE_DEL_3.2.4.2.pdf; Jun. 6, 2011; pp. 1-28.

(56) References Cited

OTHER PUBLICATIONS

Sunny George, Gwanpua; "Deliverable D3.2.4.1 Literature review and experimental data of chilled apple quality models"; http://www.frisbee-project.eu/images/result/FRISBEE_DEL_3.2.4.1.pdf; Mar. 1, 2011; pp. 1-24.
Swedberg, Claire; "DOD Considers RFID-based Solutions for Tracking Food's Shelf Life"; https://www.rfidjournal.com/articles/pdf?11423; Feb. 11, 2014; pp. 1-3.
Swedberg, Claire; "Researchers Seek to Reduce Wastage for First-Strike Rations"; https://www.rfidjournal.com/articles/pdf?9162; Jan. 26, 2012; pp. 1-4.
Swedberg, Claire; "Schuitema Ponders Future of Fresh-Chain Pilot"; https://www.rfidjournal.com/articles/pdf?3793; Dec. 10, 2007; pp. 1-4.
Swedberg, Claire; "Starbucks Keeps Fresh with RFID"; https://www.rfidjournal.com/articles/view?2890; Dec. 13, 2006; pp. 1-1.
Taoukis, P. S., et al.; "Applicability of Time-Temperature Indicators as Shelf Life Monitors of Food Products"; Journal of Food Science; vol. 54, Issue 4; Jul. 1989; pp. 783-788.
Taoukis, P. S., et al.; "Use of time-temperature integrators and predictive modelling for shelf life control of chilled fish under dynamic storage conditions"; International Journal of Food Microbiology, vol. 53; 1999; pp. 21-31.
Taoukis, Petros et al.; "Deliverable D.2.1.2 Temperature monitoring techniques and traceability systems along the cold chain";http://www.frisbee-project.eu/images/result/FRISBEE_DEL_2%201%202.pdf; Jul. 26, 2011; pp. 1-28.
Taoukis, Petros; "Deliverable D 3.2.4.4 Literature review and experimental data of frozen milk products and vegetables quality models"; http://www.frisbee-project.eu/images/result/FRISBEE_DEL_3-2-4-4.pdf; Jun. 6, 2011; pp. 1-24.
This New World by Huffpost; "Eating Ugly: The Food Waste That Could Refeed America"; https://www.facebook.com/ThisNewWorldHuffPost/videos/428476821288487; Apr. 22, 2019; pp. 1-9.
Trust in Food™; "Sustainability Research Report 2019"; https://www.zestlabs.com/downloads/Trust-In-Food-Sustainability-Survey-2019.pdf; Available as early as Jul. 18, 2019; pp. 1-19.
United States Army Medical Command; "U.S. Army Veterinary Command Guidelines and Procedures"; https://www.dla.mil/Portals/104/Documents/TroopSupport/Subsistence/Rations/qapub s/medcom/40-13.pdf; Feb. 13, 2006; pp. 1-171.
Wells, John H., et al.; "A Kinetic Approach to Food Quality Prediction using Full-History Time-Temperature Indicators"; Journal of Food Science; vol. 53, Issue 6; Nov. 1988; pp. 1866-1871.
Wells, John H., et al.; "A Quality-Based Inventory Issue Policy for Perishable Foods"; Journal of Food Processing & Preservation; vol. 12, Issue 4; Jan. 1989; pp. 271-292.
Wells, John Henry, et al.; "Application of Time-Temperature Indicators in Monitoring Changes in Quality Attributes of Perishable and Semiperishable Foods"; Journal of Food Science; vol. 53, Issue 1; Jan. 1988; pp. 148-152, 156.
Weston, L.A. et. al.; "Preharvest Factors Affecting Postharvest Quality of Vegetables"; HortScience; vol. 32(5), Aug. 1997, pp. 812-816.
Williamson, Katie et al.; "Climate Change Needs Behavior Change"; https://www.zestlabs.com/downloads/2018-CCNBC-Report.pdf; 2018; pp. 1-22.
Zelem, MC.; "Deliverable D.2.3.1 National legal and ethical requirements for the surveys"; http://www.frisbee-project.eu/images/result/FRISBEE_DEL_2.3.1.pdf; Jun. 23, 2011; pp. 1-68.
*Zest Labs, Inc.* v *Walmart*; Bohling, Joshua; "Transcript of the Testimony of Bohling, Joshua"; Bushman Court Reporting; Case No. 4:18-CV-00500-JM; Aug. 15-16, 2019; pp. 5-6, 47-48, 52-69, 78, 80-82, 85, 87, 98-102, 107-134, 137-145, 158-163, 182-184, 209-210, 233-234, 239-242, 246, and 357.
*Zest Labs, Inc.* v *Walmart*; Dickinson, Q. Todd; "Expert Report of Q. Todd Dickinson"; United States District Court for the Eastern District of Arkansas; Case No. 4:18-CV-00500-JM; Oct. 29, 2019; pp. 1-33.
*Zest Labs, Inc.* v *Walmart*; Kunin, Stephen G.; "Rebuttal Expert Report of Stephen G. Kunin"; United States District Court for the Eastern District of Arkansas; Case No. 4:18-CV-00500-JM; Nov. 25 2019; pp. 1-38.
*Zest Labs, Inc.* v *Walmart*; Zest Labs, Inc. et al.; "Complaint"; United States District Court for the Eastern District of Arkansas; Case No. 4:18-CV-00500-JM; Aug. 1, 2018; pp. 1-26.
Zest Labs; "Blockchain for Supply Chains"; https://www.zestlabs.com/challenges/blockchain-for-supply-chains/; Available as early as Jul. 18, 2019; pp. 1-4.
Zest Labs; "Food Safety and the Supply Chain"; https://www.zestlabs.com/challenges/food-safety/; Available as early as Jul. 18, 2019; pp. 1-5.
Zest Labs; "Food Supplier Operational Efficiency"; https://www.zestlabs.com/challenges/food-supplier-operational-efficiency/; Available as early as Jul. 18, 2019; pp. 1-5.
Zest Labs; "Food Waste is a Significant Problem"; https://www.zestlabs.com/challenges/food-waste-challenge/; Available as early as Jul. 18, 2019; pp. 1-6.
Zest Labs; "Fresh Food Supply Chain"; https://www.zestlabs.com/challenges/fresh-food-supply-chain/; Available as early as Jul. 18, 2019; pp. 1-5.
Zest Labs; "Fresh Food Sustainability"; https://www.zestlabs.com/challenges/fresh-food-sustainability/; Available as early as Jul. 18, 2019; pp. 1-4.
Zest Labs; "Fresh Produce"; http://www.zestlabs.com/fresh-produce; Available as early as Oct. 21, 2017; pp. 1-14.
Zest Labs; "On-Demand Delivery"; https://www.zestlabs.com/on-demand-delivery/; Available as early as Oct. 22, 2017; pp. 1-7.
Zest Labs; "On-demand meal quality visibility from the restaurant to consumer delivery"; https:// www.zestlabs.com/zest-delivery/; Available as early as Oct. 22, 2017; pp. 1-7.
Zest Labs; "Post-Harvest Technology"; https://www.zestlabs.com/challenges/post-harvest-technology/; Available as early as Jul. 18, 2019; pp. 1-8.
Zest Labs; "The Freshest Produce"; https://www.zestlabs.com/resources; Available as early as May 2, 2018; pp. 1-16.
Zest Labs; "Zest Fresh—Deep Dive"; https://www.zestlabs.com/resources; Available as early as May 2, 2018; pp. 1-15.
Zest Labs; "Zest Fresh Differentiation"; https://www.zestlabs.com/zest-fresh-differentiation/; Available as early as Jul. 18, 2019; pp. 1-6.
Zest Labs; "Zest Fresh for Beef, Poultry, Pork and Seafood"; https://www.zestlabs.com/zest-fresh-for-protein/; Available as early as Jul. 18, 2019; pp. 1-5.
Zest Labs; "Zest Fresh for Grocers"; https://www.zestlabs.com/zest-fresh-for-produce-for-grocers/; Available as early as Jul. 18, 2019; pp. 1-13.
Zest Labs; "Zest Fresh for Growers, Packers, and Shippers"; https://www.zestlabs.com/zest-fresh-for-growers-and-suppliers/; Available as early as Jul. 18, 2019; pp. 1-17.
Zest Labs; "Zest Fresh for Restaurants"; https://www.zestlabs.com/zest-fresh-for-produce-for-restaurants/; Available as early as Jul. 18, 2019; pp. 1-13.
Zest Labs; "Zest Fresh Grower Testimonial"; https://www.zestlabs.com/resources; Available as early as May 2, 2018; pp. 1-13.
Zest Labs; "Zest Fresh Overview"; https://www.zestlabs.com/resources; Available as early as May 2, 2018; pp. 1-19.
Zest Labs; "Zest Fresh Use Cases"; https://www.zestlabs.com/zest-fresh-use-cases/; Available as early as Jul. 18. 2019; pp. 1-6.
Zest Labs; "Zest Fresh: Pallet-level Quality Management from Harvest to Store"; http://www.zestlabs.com/zest-fresh; Available as early as Oct. 29, 2017; pp. 1-10.
Zest Labs; "Zest Labs Overview"; https://www.zestlabs.com/resources; Available as early as Aug. 1, 2018; pp. 1-13.
Zest Labs; ". . . Not Worth a Thousand Words—Why Traditional Temperature Loggers and Imaging Technologies are Inadequate to Determine Freshness and Reduce Waste"; https://www.zestlabs.com/wp-content/uploads/2018/03/WP-05-0318-Not-Worth-A-Thous and-Words.pdf; Mar. 5, 2018; pp. 1-6.
Zest Labs; "10 Limitations of Traditional Temperature Data Loggers and Why They're No Longer Adequate for the Cold Chain";

(56) References Cited

OTHER PUBLICATIONS https://www.zestlabs.com/wp-content/uploads/2018/05/PB-04-0418-10-Limitations-of -Data-Loggers.pdf; May 4, 2018; pp. 1-3.
Zest Labs; "Before and After—The Benefits of Digital Transformation in the Fresh Food Supply Chain"; https://www.zestlabs.com/downloads/Before-and-After-Digital-Transformation.pdf; Jan. 13, 2019; pp. 1-6.
Zest Labs; "Blockchain and Achieving True Transparency—Proactively Managing Food Safety and Freshness with Blockchain and IoT Technologies"; https://www.zestlabs.com/wp-content/uploads/2018/01/WP-08-0118.Blockchain.and_.Achieving.True_.Transparency-1.pdf; Jan. 8, 2018; pp. 1-4.
Zest Labs; "Blockchain and Its Value to Suppliers"; https://www.zestlabs.com/downloads/Blockchain-and-Its-Value-to-Suppliers.pdf; Available as early as Jul. 18, 2019; pp. 1-5.
Zest Labs; "Comparing Pallet- and Trailer-level Temperature Monitoring—Implications on Quality, Freshness, Traceability and Profitability for Retail Grocers"; https://www.zestlabs.com/wp-content/uploads/2018/03/WP-04-0318-Pallet-vs-Trailer .pdf; Mar. 4, 2018; pp. 1-4.
Zest Labs; "Freshness Baseline Study—Sample Report"; http://www.zestlabs.com/wp-content/uploads/2018/03/Zest-Labs-Sample-Baseline-Rep ort.pdf; Available as early as Mar. 2018; pp. 1-11.
Zest Labs; "Freshness Myths—False Beliefs That Lead to Food Waste"; https://www.zestlabs.com/downloads/Freshness-Myths.pdf; Aug. 7, 2018; pp. 1-5.
Zest Labs; "Half-bad Is Not Good"; https://www.zestlabs.com/downloads/Grocery-Store-Variability.pdf; Jun. 15, 2019; pp. 1-11.
Zest Labs; "Improve Operational Efficiency—Optimize Labor and Process Adherence to Reduce Costs"; https://www.zestlabs.com/downloads/Improving-Operational-Efficiency.pdf; Available as early as Jul. 18, 2019; pp. 1-3.
Zest Labs; "Improving Quality and Profitability for Retail Grocers—The Benefits of Pallet-level Monitoring for the Fresh and Perishable Food Cold Chain"; https://www.zestlabs.com/wp-content/uploads/2017/12/WP-01-1117.Improving.Quality .and_.Profitability.for_.Retail.Grocers.pdf; Nov. 1, 2017; pp. 1-8.
Zest Labs; "Let's Start at the Beginning—Reducing Shrink Begins at Harvest"; https://www.zestlabs.com/wp-content/uploads/2018/05/WP-12-0518-Lets-Start-at-the -Beginning.pdf; May 12, 2018; pp. 1-4.
Zest Labs; "Margins Matter—Reducing Fresh Food Waste to Improve Product Margins by 6% or More"; https://www.zestlabs.com/wp-content/uploads/2018/04/WP-11-0418-Margins-Matter-1. pdf; Apr. 11, 2018; pp. 1-6.
Zest Labs; "Measuring and Managing Operational Efficiency for Growers and Suppliers"; https://www.zestlabs.com/downloads/Zest-Fresh-Metrics-Datasheet.pdf; Aug. 25, 2019; pp. 1-5.
Zest Labs; "Monitoring the Safety and Quality of Fresh, Frozen and Processed Foods"; https://www.zestlabs.com/wp-content/uploads/2016/03/IN-SB-FreshProduce_RestaurantFoodService_031016.pdf; Mar. 10, 2016; pp. 1-2.
Zest Labs; "Pallet-level Quality Management from Harvest to Store"; https://www.zestlabs.com/wp-content/uploads/2016/03/IN_SB_FoodIndustry_ProduceGr owers_031016.pdf; Mar. 10, 2016; pp. 1-2.
Zest Labs; "Poor Customer Experiences—Half-Bad is Not Good! A Shelf-Life Variability Study"; https://www.zestlabs.com/downloads/Variability-Infographic.pdf; Available as early as Jul. 2019; pp. 1-1.
Zest Labs; "Proactive Freshness Management: Modernizing the Fresh Food Supply Chain to Reduce Waste and Improve Profitability"; https://www.zestlabs.com/downloads/Proactive-Freshness-Management.pdf; Feb. 6, 2019; pp. 1-7.
Zest Labs; "Reduce Shrink, Improve Profitability and Quality for Fresh Food"; https://www.zestlabs.com/wp-content/uploads/2016/03/IN-SB-FreshProduce_RetailGro cers_031016.pdf; Mar. 10, 2016; pp. 1-3.
Zest Labs; "Shelf-life Variability Begins in the Field—Produce Pallets Harvested on the Same Day Vary by as Much as 86 Percent, Contributing to Shrink and Lost Profits"; https://www.zestlabs.com/wp-content/uploads/2018/02/WP-10-0218-Shelf-life-Variab ility.pdf; Feb. 10, 2018; pp. 1-4.
Zest Labs; "Strawberries—Shelf-Life Variability"; https://www.zestlabs.com/downloads/Zest-Fresh-Strawberries-Report.pdf; Available as early as Jul. 2019; pp. 1-2.
Zest Labs; "The Best of Zest 2018—A Collection of Our Most Popular Blogs"; https://www.zestlabs.com/downloads/The-Best-of-Zest-2018.pdf; Available as early as 2018; pp. 1-15.
Zest Labs; "The ZIPR Code Freshness Metric—Dynamically providing the current freshness of each pallet to help you intelligently manage product and reduce shrink throughout the fresh food supply chain"; https://www.zestlabs.com/downloads/The-ZIPR-Code.pdf; Jun. 1, 2018; pp. 1-3.
Zest Labs; "Today, You Saved $67,571—How Zest Fresh for Managing the Produce Cold Chain Reduces Waste and Saves Retailers Money . . . Beginning on Day One"; https://www.zestlabs.com/downloads/Today-You-Saved.pdf; Jun. 3, 2018; pp. 1-6.
Zest Labs; "True Transparency for Freshness Management, Food Safety, Authenticity and Traceability"; https://www.zestlabs.com/wp-content/uploads/2018/03/SO-04-0218-Zest-Fresh-for-Protein-Solution-Overview.pdf; Feb. 4, 2018; pp. 1-2.
Zest Labs; "Zest Labs FAQ and Reference Guide"; https://www.zestlabs.com/downloads/Zest-Labs-FAQ-and-Reference-Guide.pdf; Jul. 1, 2018; pp. 1-6.
Zest Labs; "Zest Labs Professional Services"; https://www.zestlabs.com/wp-content/uploads/2018/03/SO-05-0318-Zest-Labs-Professional-Services.pdf; Mar. 5, 2018; pp. 1-2.
Unknown, "Material Inspection Using a Cloud Software" iQA Team, http://iqalims.com/wp-content/uploads/2015/02/MAT_INSP.pdf, pp. 1-5.
Unknown, "Inspection Planning / Quality Inspection / SPC / LIMS", Compact.Net, CAQ Software—Inspection Planning / Quality Inspection / SPC / LIMS—Incoming/Outgoing Goods Inspection, SPC/Control Charts, Statistics, Jan. 27, 2017, https://ww.caq.de/en/Software/InspectionPlanning_QualityInspection_SPC, pp. 1-4.
Unknown, "SE Inspection Incoming/Outgoing Goods Inspection and Supplier Management", Soft Expert, https://www.softexpert.com/inspectionevaluationgoods.php, Jan. 27, 2017, pp. 1-3.
Unknown, "Quality Control Inspection Software", Mipsis Software, http://www.mipsis.com/QualityInspectionSoftware.html, Jan. 27, 2017, pp. 1-3.
Anzilotti, Eillie; "These High-Tech Sensors Track Exactly How Fresh Our Produce Is So We Stop Wasting Food"; https://www.fastcompany.com/40424163/these-high-tech-sensors-track-exactly-how-fresh-our-produce-is-so-we-stop-wasting-food; May 26, 2017; pp. 1-3.
Teijin—Human Chemistry, Human Solutions, Teijin's RFID Smart Shelf-Management System Used for Mass Document Management. Retrieved online at: http://www.teijin.com/news/2014/ebd140307_11.html. 2 pages, Mar. 7, 2014.
The NeWave® Smart Inventory Managment System: Take Your Management to the Next Level, NeWave Sensor Solutions Innovation Center, Oct. 7, 2016; pp. 1-2.
3M; "3M MonitorMark Time Temperature Indicators"; https://www.3m.com/3M/en_US/company-us/all-3m-products/~/MONMARK-3M-MonitorMark-Time-Temperature-Indicators/?N=5002385+3293785721&rt=rud; Available at least as early as Feb. 7, 2019; pp. 1-4.
Agrofresh; "FreshCloud™ Storage Insights helps you monitor fruit in storage for added peace of mind"; https://www.agrofresh.com/technologies/freshcloud/storage-insights/; Available at least as early as Feb. 7, 2019; pp. 1-4.
Ahearn, Brianna; "Kroger Wins for Food Temperature Innovation"; https://www.retailsupplychaininsights.com/doc/kroger-wins-for-food-temperature-innovation-0001; Jun. 4, 2015; pp. 1-2.
Ambrosus; "Decentralised IoT Networks for Next-Generation Supply Chains"; https://ambrosus.com/#home; Available at least as early as Feb. 7, 2019; pp. 1-12.
BT9 Intelligent Supply Chain Solutions; "Multi Segment, Real Time, Cold Chain Perishable Information"; http://www.bt9-tech.com; Published 2018; pp. 1-6.

(56) References Cited

OTHER PUBLICATIONS

Business Wire; "Emerson Expands Global Capabilities in Fresh Food Monitoring with Acquisitions of Locus Traxx and PakSense"; https://www.businesswire.com/news/home/20160830005136/en/Emerson-Expands-Global-Capabilities-Fresh-Food-Monitoring; Aug. 30, 2016; pp. 1-2.

Cao, Jordan; "Intelligent Container—powered by SAP HANA"; https://blogs.saphana.com/2018/09/27/intelligent-container-powered-sap-hana/; Sep. 27, 2018; pp. 1-5.

Carrefour Group; "Carrefour launches Europe's first food blockchain"; http://www.carrefour.com/current-news/carrefour-launches-europes-first-food-blockchain; Mar. 6, 2018; pp. 1-2.

De Troch, Stefan; "Item-level cold chain monitoring, another cool NFC solution"; https://blog.nxp.com/internet-of-things-2/item-level-cold-chain-monitoring-another-cool-nfc-solution; Aug. 30, 2016; pp. 1-5.

Digi; "Digi Honeycomb Keeping food safe just got easier and cheaper. Digi Honeycomb lets you monitor your entire Cold Chain System"; https://s3.amazonaws.com/telusdigital-marketplace-production/iot/user-content/product/64aa-o.pdf; Available at least as early as Feb. 7, 2019; pp. 1-2.

DJI Ferntech; "Drones for Agriculture"; https://www.djistore.co.nz/agriculture; Available at least as early as Feb. 7, 2019; pp. 1-13.

Ecoark Holdings, Inc.; "Ocean Mist Farms Selects Zest Fresh to Optimize Freshness Management"; https://www.globenewswire.com/news-release/2018/12/04/1661680/0/en/Ocean-Mist-Farms-Selects-Zest-Fresh-to-Optimize-Freshness-Management.html; Dec. 4, 2018; pp. 1-3.

Emerson; "ProAct Services and ProAct Transport"; https://www.emerson.com/en-us/commercial-residential/proact; Available at least as early as Feb. 7, 2019; pp. 1-4.

Emerson; "Real-Time Temperature & Location Trackers"; https://climate.emerson.com/en-us/products/controls-monitoring-systems/cargo-tracking-monitoring/trackers; Available at least as early as Feb. 7, 2019; pp. 1-4.

Emerson; "Supply Chain Data Loggers"; https://climate.emerson.com/en-us/products/controls-monitoring-systems/cargo-tracking-monitoring/loggers; Available at least as early as Feb. 7, 2019; pp. 1-4.

Fast Casual; "Wireless temperature-monitoring, tracking solution available for shipping perishable goods"; https://www.fastcasual.com/news/wireless-temperature-monitoring-and-tracking-solution-now-available-for-shipping-perishable-goods/; Aug. 15, 2017; pp. 1-10.

Food and Agriculture Organization of the United Nations; "Flying robots for food security"; http://www.fao.org/zhc/detail-events/en/c/428256; Aug. 10, 2016; pp. 1-3.

Freshai; "AI-powered waste reduction for smart food businesses."; http://freshai.farmsteadapp.com/; Available as early as Feb. 7, 2019; pp. 1-5.

freshfruitportal.com; "Zest Labs fights food waste by routing pallets according to real-time freshness"; https://www.freshfruitportal.com/news/2018/07/19/technology-zest-labs-food-waste-profits-sensors; Jul. 19, 2018; pp. 1-5.

Friedman, Phil; "AI, machine learning, and more efficient routing"; https://www.omnitracs.com/blog/ai-machine-learning-and-more-efficient-routing; Jun. 28, 2018; pp. 1-6.

Gabbett, Rita Jane; "Amazon using artificial intelligence to monitor food safety issues"; http://www.micausa.org/amazon-using-artificial-intelligence-monitor-food-safety-issues/; May 9, 2018; pp. 1-3.

Grand View Research; "Cold Chain Market Size Worth $447.50 Billion by 2025 | CAGR: 15.1%"; https://www.grandviewresearch.com/press-release/global-cold-chain-market; Mar. 2019; pp. 1-10.

Greenwalt, Megan; "Acquisition Leads to New, Fresh Food Waste Solution"; https://www.waste360.com/mergers-and-acquisitions/acquisition-leads-new-fresh-food-waste-solution; Aug. 15, 2018; pp. 1-6.

Hagen, Christian et al.; "A Fresh Look: Perishable Supply Chains Go Digital"; https://www.atkearney.com/operations-performance-transformation/article?/a/a-fresh-look-perishable-supply-chains-go-digital; Available at least as early as Feb. 7, 2019; pp. 1-22.

Harvard Business Review; "How Blockchain Will Accelerate Business Performance and Power the Smart Economy"; https://hbr.org/sponsored/2017/10/how-blockchain-will-accelerate-business-performance-and-power-the-smart-economy; Oct. 27, 2017; pp. 1-8.

Hsu, Jenny W.; "Freshippo Customers Can Track Farm-To-Shelf Journey for Food"; https://www.alizila.com/hema-food-tracking/; Aug. 7, 2018; pp. 1-6.

Husseini, Talal; "Walmart's 'Eden' artificial intelligence technology to inspect fresh food for spoilage"; https://www.foodprocessing-technology.com/news/walmarts-eden-artificial-intelligence-technology-inspect-fresh-food-spoilage; Mar. 2, 2018; pp. 1-4.

IBM; "Take your food data further with Fresh Insights for IBM Food Trust"; https://www.ibm.com/blockchain/solutions/food-trust/freshness; Available at least as early as Feb. 7, 2019; pp. 1-3.

Impact Vision; "Non-invasive, real time food quality information"; https://www.impactvi.com/; Available at least as early as Feb. 7, 2019; pp. 1-18.

Impinj; "Hy-Vee Grocery Automates Cold Chain Monitoring"; https://www.impinj.com/library/customer-stories/hy-vee-cold-chain-monitoring-increases-shelf-life/; Available as early as Feb. 7, 2019; pp. 1-3.

Infratab; "Products"; https://infratab.com/products/; Available at least as early as Feb. 7, 2019; pp. 1-2.

Intel; "Intelligent Dynamic Store Merchandising Solution Cuts Losses on Perishables and Raises Brand Awareness"; Available at least as early as Feb. 7, 2019; pp. 1-12.

Kroger; "Kroger Gets HarvestMark Allows consumers to trace the origin of salads"; https://www.cspdailynews.com/foodservice/kroger-gets-harvestmark; Oct. 29, 2009; pp. 1-11.

Marvin, Rob; "Blockchain: The Invisible Technology That's Changing the World"; https://in.pcmag.com/amazon-web-services/112363/blockchain-the-invisible-technology-thats-changing-the-world; Aug. 30, 2017; pp. 1-29.

Mazur, Michal; "Six Ways Drones Are Revolutionizing Agriculture"; https://www.technologyreview.com/s/601935/six-ways-drones-are-revolutionizing-agriculture; Jul. 20, 2016; pp. 1-5.

Moorthy, Rahul et al.; "On-Shelf Availability in Retailing"; vol. 116—No. 23; International Journal of Computer Applications; Apr. 2015; pp. 47-51.

Musani, Parvez; "Eden: The Tech That's Bringing Fresher Groceries to You"; https://blog.walmart.com/innovation/20180301/eden-the-tech-thats-bringing-fresher-groceries-to-you; Mar. 1, 2018; pp. 1-4.

My Devices; "Alibaba Cloud and myDevices Partner to Launch Turnkey IoT Solutions in China"; https://mydevices.com/newspost/alibaba-cloud-mydevices-partner-launch-turnkey-iot-solutions-china/; Sep. 11, 2018; pp. 1-3.

Oracle; "Oracle Unveils Business-Ready Blockchain Applications"; https://www.oracle.com/nz/corporate/pressrelease/oow18-oracle-blockchain-applications-cloud-2018-10-23.html; Oct. 23, 2018; pp. 1-4.

Palanza, Rich; "IoT Monitoring: Rapidly Deliver on the Promise of IoT"; https://business.weather.com/blog/iot-monitoring-rapidly-deliver-on-the-promise-of-iot; May 16, 2018; pp. 1-4.

Peterson, Hayley; "Walmart is saving $2 billion with a machine called 'Eden' that inspects food and knows when it will spoil"; https://www.businessinsider.in/walmart-is-saving-2-billion-with-a-machine-called-eden-that-inspects-food-and-knows-when-it-will-spoil/articleshow/63127641.cms; Mar. 1, 2018; pp. 1-12.

Pridevel; "IoT Cold Chain Monitoring"; http://www.pridevel.com/sap-iot-cold-chain-monitoring; Available at least as early as Feb. 7, 2019; pp. 1-3.

Qa; "Carrefour and SGS Launch Visual Trust in China"; https://www.qualityassurancemag.com/article/carrefour-and-sgs-launch-visual-trust-in-china/; Sep. 28, 2017; pp. 1-4.

Ripple News Tech Staff; "Alibaba is Using Blockchain to Improve Consumer Confidence and Fight Food Fraud"; https://ripplenews.tech/2018/05/03/alibaba-is-using-blockchain-to-improve-consumer-confidence-and-fight-food-fraud/; May 3, 2018; pp. 1-7.

(56) References Cited

OTHER PUBLICATIONS

Sensefly; "Why Use Agriculture Drones?"; https://www.sensefly.com/industry/agricultural-drones-industry; Available at least as early as Feb. 7, 2019; pp. 1-15.
Sensegrow; "Supply Chain Monitoring with Real-time IoT Platform"; http://www.sensegrow.com/blog/supply-chain-monitoring; May 10, 2018; pp. 1-5.
Smart Sense; "Supermarket Remote Monitoring Solutions"; https://www.smartsense.co/industries/retail/supermarkets; Available at least as early as Feb. 7, 2019; pp. 1-6.
Smilo; "The latest generation hybrid blockchain platform"; https://smilo.io/files/Smilo_White_Paper_V1.8.1.pdf; Available at least as early as Feb. 7, 2019; pp. 1-33.
Springer, Jon; "Walmart, Kroger join suppliers in blockchain food safety initiative"; https://www.supermarketnews.com/news/walmart-kroger-join-suppliers-blockchain-food-safety-initiative; Aug. 22, 2017; pp. 1-4.
TCS Worldwide; "TCS Cargo Monitoring Solution: Track freshness of perishable cargo"; https://www.tcs.com/cargo-monitoring-solution; Available at least as early as Feb. 7, 2019; pp. 1-7.
TE-FOOD; "TE-FOOD Partners with HALAL TRAIL Bringing Halal Food Companies to the Blockchain"; https://www.reuters.com/brandfeatures/venture-capital/article?id=38153; May 31, 2018; pp. 1-6.
Tech Mahindra; "Cold Chain Monitoring"; https://www.techmahindra.com/services/NextGenSolutions/DES/Solutions/Cold_Chain_Monitoring.aspx; Available at least as early as Feb. 7, 2019; pp. 1-4.
Tech Mahindra; "Farm to fork"; https://www.techmahindra.com/services/NextGenSolutions/DES/Solutions/Farm_to_fork.aspx; Available at least as early as Feb. 7, 2019; pp. 1-2.
Tive; "A Complete Supply Chain Visibility System"; https://tive.co/product; Available at least as early as Feb. 7, 2019; pp. 1-7.
Tive; "Environmental Monitoring for Perishables"; https://tive.co/solution/environmental-monitoring-for-perishables/; Available at least as early as Feb. 7, 2019; pp. 1-5.
TraQtion; "TraQtion's Supply Chain Solution Manages Global Food Supplier Compliance and Audits"; https://www.traqtion.com/documents/TraQtion-Costco.pdf; Available as early as Feb. 7, 2019; pp. 1-2.
Trimble; "Trimble Acquires HarvestMark to Provide Food Traceability and Quality Control"; https://www.prnewswire.com/news-releases/trimble-acquires-harvestmark-to-provide-food-traceability-and-quality-control-300070050.html; Apr. 22, 2015; pp. 1-6.
Tsenso; "The Fresh Index: A Real-Time Shelf Life Indicator"; https://tsenso.com/en/freshindex-instead-of-bestbefore; Available at least as early as Feb. 7, 2019; pp. 1-5.
Verigo; "Introducing Pod Quality Continuous Product Life Data, From Farm to Store"; https://www.farmtoforkfresh.com/; Available at least as early as Feb. 7, 2019; pp. 1-8.
Wageningen UR Food & Biobased Research; "Food & Biobased Research"; https://www.worldfoodinnovations.com/userfiles/documents/FBR%20Corporate%20Brochure.pdf; Jul. 2014; pp. 1-24.
Whelan, Jenny; "Kelsius to Install FoodCheck Monitoring System in SuperValu and Centra Stores"; https://www.checkout.ie/kelsius-signs-deal-to-put-foodcheck-monitoring-system-in-supervalu-and-centra-stores/; Aug. 6, 2015; pp. 1-4.
Wynne-Jones, Stephen; "Maxima Group Unveils 'Electronic Nose' to Track Freshness"; https://www.esmmagazine.com/maxima-group-unveils-elecrtronic-nose-track-freshness/29589; Jul. 5, 2016; pp. 1-4.
Xinfin; "Enterprise Ready Hybrid Blockchain for Global Trade and Finance"; https://www.xinfin.org; Available at least as early as Feb. 7, 2019; pp. 1-13.
Yiannas, Frank; "How Walmart's SPARK Keeps Your Food Fresh"; https://blog.walmart.com/sustainability/20150112/how-walmarts-spark-keeps-your-food-fresh; Jan. 12, 2015; pp. 1-16.
Zest Labs; "Zest Fresh for Growers, Retailers and Restaurants"; https://www.zestlabs.com/zest-fresh-for-produce/; Available at least as early as Feb. 7, 2019; pp. 1-7.
Haard, Norman F., et al.; "Characteristics of Edible Plant Tissues"; Food Chemistry, edited by Owen R. Fennema; 3rd Ed.; Marcel Dekker, Inc.; 1996; pp. 943-1011.
Haugen, John E., et al.; "Application of gas-sensor array technology for detection and monitoring of growth of spoilage bacteria in milk: A model study"; Analytica Chimica Acta; vol. 565, No. 1; https://doi.org/10.1016/j.aca.2006.02.016; Feb. 23, 2006; pp. 10-16.
Kader, Adel A., et al .; "Technologies to Extend the Refrigerated Shelf Life of Fresh Fruit"; Food Storage Stability, edited by Irwin A. Taub, et al.; Boca Raton; CRC Press; 1998; pp. 1-27.
Kong, F. et al.; "Chemical Deterioration and Physical Instability of Foods and Beverages"; The Stability and Shelf Life of Food, edited by Persis Subramaniam; 2nd Ed.; Woodhead Publishing; 2016; pp. 1-21.
Labuza, T. P., et al.; "The Relationship Between Processing and Shelf Life"; Foods for the '90s, edited by Gordon G. Birch, et al.; Elsevier Applied Science; Aug. 1, 1990; pp. 1-21.
Robertson, Gordon L.; "Food Packaging: Principles and Practice"; 3rd Ed.; Boca Raton; CRC Press; 2013; pp. 1-33.
Singh, R. P.; "Scientific Principles of Shelf-Life Evaluation"; Shelf-Life Evaluation of Foods, edited by Dominic Man, et al.; 2nd Ed.; Aspen Publishers, Inc.; 2000; pp. 1-23.
Singh, R. Paul et al.; "Introduction to Food Engineering"; 5th Ed.; Academic Press; 2014; pp. 1-31.
Wells, John H. et al.; "Quality Management During Storage and Distribution"; Food Storage Stability, edited by Irwin A. Taub, et al.; Boca Raton; CRC Press; 1998; pp. 1-29.
Wells, John H., et al.; "Temperature Tolerance of Foods during Distribution"; Handbook of Food Engineering Practice, edited by Kenneth J. Valentas, et al.; Boca Raton; CRC Press; 1997; pp. 1-29.
Wells, John H., et al.; "The Application of Time-Temperature Indicator Technology to Food Quality Monitoring and Perishable Inventory Management"; Mathematical Modelling of Food Processing Operations, edited by Stuart Thorne; Elsevier Applied Science; 1992; pp. 1-41.
Kader, Adel A.; "Postharvest Technology of Horticultural Crops"; 2002; 3rd Ed.; University of California Agriculture and Natural Resources; Oakland; 56 pages.
Kader, Adel A.; "Postharvest Technology of Horticultural Crops"; 2002; 3rd Ed.; University of California Agriculture and Natural Resources; Oakland; 74 pages.
Kader, Adel A.; "Postharvest Technology of Horticultural Crops"; 2002; 3rd Ed.; University of California Agriculture and Natural Resources; Oakland; pp. 113-196.
Kader, Adel A.; "Postharvest Technology of Horticultural Crops"; 2002; 3rd Ed.; University of California Agriculture and Natural Resources; Oakland; pp. 197-250.
Kader, Adel A.; "Postharvest Technology of Horticultural Crops"; 2002; 3rd Ed.; University of California Agriculture and Natural Resources; Oakland; pp. 251-314.
Kader, Adel A.; "Postharvest Technology of Horticultural Crops"; 2002; 3rd Ed.; University of California Agriculture and Natural Resources; Oakland; pp. 315-384.
Kader, Adel A.; "Postharvest Technology of Horticultural Crops"; 2002; 3rd Ed.; University of California Agriculture and Natural Resources; Oakland; pp. 385-434.
Kader, Adel A.; "Postharvest Technology of Horticultural Crops"; 2002; 3rd Ed.; University of California Agriculture and Natural Resources; Oakland; pp. 435-480.
Kader, Adel A.; "Postharvest Technology of Horticultural Crops"; 2002; 3rd Ed.; University of California Agriculture and Natural Resources; Oakland; pp. 67-112.
*Zest Labs, Inc.* v *Walmart*; ECF No. 002; Zest Labs, Inc. et al.; "Motion for Leave to File Complaint Under Seal and to Establish Briefing Schedule Relating to Potentially Confidential Information in Complaint"; United States District Court for the Eastern District of Arkansas; Case No. 4:18-CV-00500-JM; Aug. 1, 2018; pp. 1-4.
*Zest Labs, Inc.* v *Walmart*; ECF No. 003; Zest Labs, Inc. et al.; "Brief in Support of Motion for Leave to File Complaint Under Seal and to Establish Briefing Schedule Relating to Potentially Confidential Information Complaint"; United States District Court for the Eastern District of Arkansas; Case No. 4:18-CV-00500-JM; Aug. 1, 2018; pp. 1-4.

(56) References Cited

OTHER PUBLICATIONS

*Zest Labs, Inc.* v *Walmart*; ECF No. 035; Walmart; "Defendant'S Response to Plaintiffs' Motion for Leave to File Complaint Under Seal"; United States District Court for the Eastern District of Arkansas; Case No. 4:18-CV-00500-JM; Aug. 27, 2018; pp. 1-3.
*Zest Labs, Inc.* v *Walmart*; ECF No. 038; Zest Labs, Inc. et al.; "Plaintiffs' Reply in Support of Plaintiffs' Motion for Leave to File Complaint Under Seal"; United States District Court for the Eastern District of Arkansas; Case No. 4:18-CV-00500-JM; Aug. 31, 2018; pp. 1-3.
*Zest Labs, Inc.* v *Walmart*; ECF No. 041; Walmart; "Defendant'S Motion for Leave to File Under Seal"; United States District Court for the Eastern District of Arkansas; Case No. 4:18-CV-00500-JM; Sep. 4, 2018; pp. 1-3.
*Zest Labs, Inc.* v *Walmart*; ECF No. 098; Walmart; "Defendant'S Brief in Support of Its Motion for Protective Order and to Compel Identification of Alleged Trade Secrets"; United States District Court for the Eastern District of Arkansas; Case No. 4:18-CV-00500-JM; Feb. 11, 2019; pp. 1-29.
*Zest Labs, Inc.* v *Walmart*; ECF No. 101-01; Sammi, P. Anthony; "Exhibit A"; United States District Court for the Eastern District of Arkansas; Case No. 4:18-CV-00500-JM; Feb. 15, 2019; pp. 1-3.
*Zest Labs, Inc.* v *Walmart*; ECF No. 101-02; Tulin, Edward L.; "Exhibit B"; United States District Court for the Eastern District of Arkansas; Case No. 4:18-CV-00500-JM; Feb. 15, 2019; pp. 1-4.
*Zest Labs, Inc.* v *Walmart*; ECF No. 101-03; Tulin, Edward L.;" Exhibit C"; United States District Court for the Eastern District of Arkansas; Case No. 4:18-CV-00500-JM; Feb. 15, 2019; pp. 1-5.
*Zest Labs, Inc.* v *Walmart*; ECF No. 101-04; Zest Labs, Inc. et al.; "Exhibit D Filed Under Seal Pursuant to Order Dated Sep. 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101-05; Zest Labs, Inc. et al.; "Exhibit E Filed Under Seal Pursuant to Order Dated Sep. 7, 2018"; United States District Court for the Eastern District of Arkansas; Case No. 4:18-CV-00500-JM; Feb. 15, 2019; 1 page.
*Zest Labs, Inc.* v *Walmart*; ECF No. 101; Zest Labs, Inc. et al.; "Plaintiffs' Brief in Opposition to Defendant's Motion for Protective Order and to Compel Identification of Trade Secrets"; United States District Court for the Eastern District of Arkansas; Case No. 4:18-CV-00500-JM; Feb. 15, 2019; pp. 1-28.
*Zest Labs, Inc.* v *Walmart*; ECF No. 102-01; Zest Labs, Inc. et al.; "Exhibit A"; United States District Court for the Eastern District of Arkansas; Case No. 4:18-CV-00500-JM; Feb. 20, 2019; pp. 1-28.
*Zest Labs, Inc.* v *Walmart*; ECF No. 102-02; Walmart; "Exhibit B"; United States District Court for the Eastern District of Arkansas; Case No. 4:18-CV-00500-JM; Feb. 20, 2019; pp. 1-59.
*Zest Labs, Inc.* v *Walmart*; ECF No. 102-03; Zest Labs, Inc. et al.; "Exhibit C Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-04; Walmart; "Exhibit D"; United States District Court for the Eastern District of Arkansas; Case No. 4:18-CV-00500-JM; Feb. 20, 2019; pp. 1-10.
*Zest Labs, Inc.* v *Walmart*; ECF No. 102-06; Zest Labs, Inc. et al.; "Exhibit F Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-07; Zest Labs, Inc. et al.; "Exhibit G Filed Under Seal"; United States District Court for the Eastern District of Arkansas; Case No. 4:18-CV-00500-JM; Feb. 20, 2019; 1 page.
*Zest Labs, Inc.* v *Walmart*; ECF No. 102-08; Williams, Fred I.; "Exhibit H"; United States District Court for the Eastern District of Arkansas; Case No. 4:18-CV-00500-JM; Feb. 20, 2019; pp. 1-5.
*Zest Labs, Inc.* v *Walmart*; ECF No. 102-09; Simons, Michael; "Exhibit I"; United States District Court for the Eastern District of Arkansas; Case No. 4:18-CV-00500-JM; Feb. 20, 2019; pp. 1-8.
*Zest Labs, Inc.* v *Walmart*; ECF No. 102-10; Williams, Fred I.; "Exhibit J"; United States District Court for the Eastern District of Arkansas; Case No. 4:18-CV-00500-JM; Feb. 20, 2019; pp. 1-4.
*Zest Labs, Inc.* v *Walmart*; ECF No. 102-11; Simons, Michael; "Exhibit K"; United States District Court for the Eastern District of Arkansas; Case No. 4:18-CV-00500-JM; Feb. 20, 2019; pp. 1-2.
*Zest Labs, Inc.* v *Walmart*; ECF No. 102-12; Tulin, Edward L.; "Exhibit L"; United States District Court for the Eastern District of Arkansas; Case No. 4:18-CV-00500-JM; Feb. 20, 2019; pp. 1-4.
*Zest Labs, Inc.* v *Walmart*; ECF No. 102-13; Sammi, P. Anthony; "Exhibit M"; United States District Court for the Eastern District of Arkansas; Case No. 4:18-CV-00500-JM; Feb. 20, 2019; pp. 1-3.
*Zest Labs, Inc.* v *Walmart*; ECF No. 102-14; Sammi, P. Anthony; "Exhibit N"; United States District Court for the Eastern District of Arkansas; Case No. 4:18-CV-00500-JM; Feb. 20, 2019; pp. 1-3.
*Zest Labs, Inc.* v *Walmart*; ECF No. 102; Zest Labs, Inc. et al.; "Plaintiffs' Motion to Compel Supplemental Responses to Interrogatories and Requests for Production From Defendant"; United States District Court for the Eastern District of Arkansas; Case No. 4:18-CV-00500-JM; Feb. 20, 2019; pp. 1-6.
*Zest Labs, Inc.* v *Walmart*; ECF No. 103; Zest Labs, Inc. et al.; "Plaintiffs' Brief in Support of Motion to Compel Supplemental Responses to Interrogatories and Requests for Production From Defendant"; United States District Court for the Eastern District of Arkansas; Case No. 4:18-CV-00500-JM; Feb. 20, 2019; pp. 1-24.
*Zest Labs, Inc.* v *Walmart*; ECF No. 105-1; Walmart; "Exhibit A—Filed Under Seal Pursuant to Order Dated Sep. 7, 2018"; United States District Court for the Eastern District of Arkansas; Case No. 4:18-CV-00500-JM; Feb. 25, 2019; 1 page.
*Zest Labs, Inc.* v *Walmart*; ECF No. 105; Walmart; "Defendant'S Response to Plaintiffs' Motion to Compel"; United States District Court for the Eastern District of Arkansas; Case No. 4:18-CV-00500-JM; Feb. 25, 2019; pp. 1-21.
*Zest Labs, Inc.* v *Walmart*; ECF No. 125; Zest Labs, Inc. et al.; "Plaintiffs' Motion to Compel Defendant Walmart to Comply With the Court's Mar. 6, 2019 Order and Otherwise Produce Technical Discovery"; United States District Court for the Eastern District of Arkansas; Case No. 4:18-CV-00500-JM; Apr. 22, 2019; pp. 1-9.
*Zest Labs, Inc.* v *Walmart*; ECF No. 126; Zest Labs, Inc. et al.; "Plaintiffs' Brief in Support of Motion to Compel Defendant Walmart to Comply With the Court'S Mar. 6, 2019 Order and Otherwise Produce Technical Discovery"; United States District Court forthe Eastern District of Arkansas; Case No. 4:18-CV-00500-JM; Apr. 22, 2019; pp. 1-21.
*Zest Labs, Inc.* v *Walmart*; ECF No. 130-1; Sammi, P. Anthony; "*Zest* v. *Walmart*: Mar. 29, 2019 M. Simons Letter to P. Sammi Re Deficient Production of Technical Documents"; United States District Court for the Eastern District of Arkansas; Case No. 4:18-CV-00500-JM; May 8, 2019; pp. 1-2.
*Zest Labs, Inc.* v *Walmart*; ECF No. 130-2; Tulin, Edward L.; "*Zest* v. *Walmart*: Deposition Notices"; United States District Court for the Eastern District of Arkansas; Case No. 4:18-CV-00500-JM; May 8, 2019; pp. 1-2.
*Zest Labs, Inc.* v *Walmart*; ECF No. 130-3; Simons, Michael; "*Zest* v. *Walmart*: Deposition Notices"; United States District Court for the Eastern District of Arkansas; Case No. 4:18-CV-00500-JM; May 8, 2019; pp. 1-3.
*Zest Labs, Inc.* v *Walmart*; ECF No. 130-4; Walmart; "Exhibit D—Filed Under Seal Pursuant to Order Dated Sep. 7, 2018"; United States District Court for the Eastern District of Arkansas; Case No. 4:18-CV-00500-JM; May 8, 2019; 1 page.
*Zest Labs, Inc.* v *Walmart*; ECF No. 130-5; Simons, Michael; "*Zest Labs* v. *Walmart*—Walmart's Apr. 5, 2019 Production"; United States District Court for the Eastern District of Arkansas; Case No. 4:18-CV-00500-JM; May 8, 2019; pp. 1-2.
*Zest Labs, Inc.* v *Walmart*; ECF No. 130; Walmart; "Defendant's Response to Plaintiffs' Motion to Compel Compliance With the Mar. 6, 2019 Order and Technical Discovery"; United States District Court forthe Eastern District of Arkansas; Case No. 4:18-CV-00500-JM; May 8, 2019; pp. 1-26.
*Zest Labs, Inc.* v *Walmart*; ECF No. 131-1; Walmart; "Exhibit A—Filed Under Seal Pursuant to Order Dated Sep. 7, 2018"; United

(56) References Cited

OTHER PUBLICATIONS

States District Court for the Eastern District of Arkansas; Case No. 4:18-CV-00500-JM; May 8, 2019; 1 page.
*Zest Labs, Inc.* v *Walmart*; ECF No. 131-2; Walmart; "Exhibit B—Filed Under Seal Pursuant to Order Dated Sep. 7, 2018"; United States District Court for the Eastern District of Arkansas; Case No. 4:18-CV-00500-JM; May 8, 2019; 1 page.
*Zest Labs, Inc.* v *Walmart*; ECF No. 131-3; Sammi, P. Anthony; "Re: 4:18-CV-00500-JM Zest Labs Inc et al v. Wal-Mart Inc"; United States District Court for the Eastern District of Arkansas; Case No. 4:18-CV-00500-JM; May 8, 2019; 1 page.
*Zest Labs, Inc.* v *Walmart*; ECF No. 131-4; Simons, Michael; "Re: 4:18-CV-00500-JM Zest Labs Inc et al v. Wal-Mart Inc"; United States District Court for the Eastern District of Arkansas; Case No. 4:18-CV-00500-JM; May 8, 2019; 1 page.
*Zest Labs, Inc.* v *Walmart*; ECF No. 131; Walmart; "Defendant's Sur-Reply Brief in Further Opposition to Plaintiffs' Motion to Compel"; United States District Court for the Eastern District of Arkansas; Case No. 4:18-CV-00500-JM; May 8, 2019; pp. 1-21.
*Zest Labs, Inc.* v *Walmart*; ECF No. 250; Walmart; "Defendant's Reply Brief in Support of Its Motion to Exclude Proposed Expert Testimony of Patent Attorney Q. Todd Dickinson"; United States District Court for the Eastern District of Arkansas; Case No. 4:18-CV-00500-JM; Mar. 27, 2020; pp. 1-13.
*Zest Labs, Inc.* v *Walmart*; ECF No. 257-1; Walmart; "Defendant's Surreply in Further Opposition to Zest Labs, Inc.'S Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-168.
*Zest Labs, Inc.* v *Walmart*; ECF No. 257-1; Walmart; "Defendant's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 169-336.
*Zest Labs, Inc.* v *Walmart*; ECF No. 257-1; Walmart; "Defendant's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 337-342.
*Zest Labs, Inc.* v *Walmart*; ECF No. 257; Walmart; "Defendant's Motion for Leave to File Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Mar. 31, 2020; pp. 1-3.
*Zest Labs, Inc.* v *Walmart*; ECF No. 261-1; Blitzer, Rachel R.; "Declaration of Rachel R. Blitzer Regarding Walmart's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-169.
*Zest Labs, Inc.* v *Walmart*; ECF No. 261-1; Blitzer, Rachel R.; "Declaration of Rachel R. Blitzer Regarding Walmart's Surreply in Further Opposition to Zest Labs, Inc.'S Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 170-337.
*Zest Labs, Inc.* v *Walmart*; ECF No. 261; Walmart; "Defendant's Surreply in Further Opposition to Zest Labs, Inc.'s Motion for Partial Summary Judgment That Walmart Used and Disclosed Zest's Information in the Walmart Application"; United States District Court for the Eastern District of Arkansas; Case No. 4:18-CV-00500-JM; Apr. 6, 2020; pp. 1-5.
*Zest Labs, Inc.* v *Walmart*; ECF No. 262; Walmart; "Brief in Support of Defendant's Motion for Summary Judgment"; United States District Court for the Eastern District of Arkansas; Case No. 4:18-CV-00500-JM; Apr. 21, 2020; pp. 1-54.
*Zest Labs, Inc.* v *Walmart*; ECF No. 263; Walmart; "Defendant's Motion to Exclude Certain Proposed Expert Testimony of Mark Lanning"; United States District Court for the Eastern District of Arkansas; Case No. 4:18-CV-00500-JM; Apr. 21, 2020; pp. 1-6.
*Zest Labs, Inc.* v *Walmart*; ECF No. 264; Walmart; "Brief in Support of Defendant's Motion to Exclude Proposed Expert Testimony of Mark Lanning"; United States District Court for the Eastern District of Arkansas; Case No. 4:18-CV-00500-JM; Apr. 21, 2020; pp. 1-26.
*Zest Labs, Inc.* v *Walmart*; ECF No. 265; Walmart; "Defendant's Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-7.
*Zest Labs, Inc.* v *Walmart*; ECF No. 266; Walmart; "Brief in Support of Defendant's Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-22.
*Zest Labs, Inc.* v *Walmart*; ECF No. 267; Walmart; "Defendant's Response to Zest Labs, Inc.'s Motion for Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-23.
*Zest Labs, Inc.* v *Walmart*; ECf No. 268; Walmart; "Defendant's Response to Zest Labs, Inc.'s Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-29.
*Zest Labs, Inc.* v *Walmart*; ECF No. 269; Walmart; "Defendant's Response to Plaintiffs' Motion to Exclude Testimony of Walmart's Damages Expert, Dr. William Choi"; United States District Court for the Eastern District of Arkansas; Case No. 4:18-CV-00500-JM; Apr. 21, 2020; pp. 1-17.
*Zest Labs, Inc.* v *Walmart*; ECF No. 270; Walmart; "Defendant's Response to Plaintiffs' Motion to Exclude Testimony of Walmart's Technical Expert, Dr. David Dobkin, Ph.D."; United States District Court for the Eastern District of Arkansas; Case No. 4:18-CV-00500-JM; Apr. 21, 2020; pp. 1-13.
*Zest Labs, Inc.* v *Walmart*; ECF No. 271; Walmart; "Defendant's Response to Plaintiffs' Motion to Exclude Testimony of Walmart's Technical Expert, Dr. Catherine Adams Hutt, Ph.D."; United States District Court for the Eastern District of Arkansas; Case No. 4:18-CV-00500-JM; Apr. 21, 2020; pp. 1-25.
*Zest Labs, Inc.* v *Walmart*; ECF No. 272; Walmart; "Defendant's Reply Brief in Support of Its Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-22.
*Zest Labs, Inc.* v *Walmart*; ECF No. 273; Walmart; "Defendant's Reply Brief in Support of Its Motion for Summary Judgment"; United States District Court for the Eastern District of Arkansas; Case No. 4:18-CV-00500-JM; Apr. 21, 2020; pp. 1-56.
*Zest Labs, Inc.* v *Walmart*; ECF No. 274; Walmart; "Defendant's Reply Brief in Support of Its Motion to Exclude Proposed Expert Testimony of Mark Lanning"; United States District Court for the Eastern District of Arkansas; Case No. 4:18-CV-00500-JM; Apr. 21, 2020; pp. 1-22.
*Zest Labs, Inc.* v *Walmart*; ECF No. 275; Zest Labs, Inc. et al.; "Zest Labs Inc.'s Motion for Partial Summary Judgment That Walmart Used and Disclosed Zest's Information in the Walmart Applications"; United States District Court for the Eastern District of Arkansas; Case No. 4:18-CV-00500-JM; Apr. 21, 2020; pp. 1-4.
*Zest Labs, Inc.* v *Walmart*; ECF No. 276; Zest Labs, Inc et al.; "Plaintiffs' Motion to Exclude Testimony of Walmart's Expert, Dr. David P. DOBKIN"; United States District Court for the Eastern District of Arkansas; Case No. 4:18-CV-00500-JM; Apr. 21, 2020; pp. 1-3.
*Zest Labs, Inc.* v *Walmart*; ECF No. 277; Zest Labs, Inc. et al.; "Brief in Support of Plaintiffs' Motion to Exclude the Testimony of Walmart's Expert Witness, Dr. David P. DOBKIN"; United States

(56) References Cited

OTHER PUBLICATIONS

District Court for the Eastern District of Arkansas; Case No. 4:18-CV-00500-JM; Apr. 21, 2020; pp. 1-59.
Zest Labs, Inc. v Walmart; ECF No. 278; Zest Labs, Inc. et al.; "Plaintiffs' Motion to Exclude Testimony of Walmart Expert, Dr. Catherine Adams Hutt"; United States District Court for the Eastern District of Arkansas; Case No. 4:18-CV-00500-JM; Apr. 21, 2020; pp. 1-4.
Zest Labs, Inc. v Walmart; ECF No. 279; Zest Labs, Inc. et al.; "Brief in Support of Plaintiffs' Motion to Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-64.
Zest Labs, Inc. v Walmart; ECF No. 280; Zest Labs, Inc. et al.; "Zest Labs Inc.'S Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-4.
Zest Labs, Inc. v Walmart; ECF No. 281; Zest Labs, Inc. et al.; "Plaintiffs' Motion to Exclude Testimony of Walmart's Damages Expert, Dr. William Choi"; United States District Court for the Eastern District of Arkansas; Case No. 4:18-CV-00500-JM; Apr. 21, 2020; pp. 1-4.
Zest Labs, Inc. v Walmart; ECF No. 282; Zest Labs, Inc. et al.; "Plaintiffs' Brief in Support of Motion to Exclude Testimony of Walmart's Damages Expert, Dr. William Choi"; United States District Court for the Eastern District of Arkansas; Case No. 4:18-CV-00500-JM; Apr. 21, 2020; pp. 1-30.
Zest Labs, Inc. v Walmart; ECF No. 283; Zest Labs, Inc. et al.; "Zest Labs Inc.'S Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-159.
Zest Labs, Inc. v Walmart; ECF No. 284; Zest Labs, Inc. et al.; "Zest Labs Inc.'S Brief in Support of Its Motion for Partial Summary Judgment That Walmart Used and Disclosed Zest Labs' Information in the Walmart Applications"; United States District Court for the Eastern District of Arkansas; Case No. 4:18-CV-00500-JM; Apr. 21, 2020; pp. 1-165.
Zest Labs, Inc. v Walmart; ECF No. 285; Zest Labs, Inc. et al.; "Zest Labs Inc.'S Motion for Summary Judgment on Its Claim for Breach of Contract"; United States District Court for the Eastern District of Arkansas; Case No. 4:18-CV-00500-JM; Apr. 21, 2020; pp. 1-3.
Zest Labs, Inc. v Walmart; ECF No. 286; Zest Labs, Inc. et al.; "Zest Labs Inc.'S Brief in Support of Its Motion for Summary Judgment on Its Claim for Breach of Contract"; United States District Court for the Eastern District of Arkansas; Case No. 4:18-CV-00500-JM; Apr. 21, 2020; pp. 1-30.
Zest Labs, Inc. v Walmart; ECF No. 287; Zest Labs, Inc. et al.; "Plaintiffs' Response to Defendant's Motion for Summary Judgment"; United States District Court for the Eastern District of Arkansas; Case No. 4:18-CV-00500-JM; Apr. 21, 2020; pp. 1-138.
Zest Labs, Inc. v Walmart; ECF No. 288; Zest Labs, Inc. et al.; "Plaintiffs' Opposition to Defendant's Motion to Exclude Testimony of Damages Expert Stephen L. Becker, Ph.D."; United States District Court for the Eastern District of Arkansas; Case No. 4:18-CV-00500-JM; Apr. 21, 2020; pp. 1-63.
Zest Labs, Inc. v Walmart; ECF No. 289; Zest Labs, Inc. et al.; "Plaintiffs' Brief in Opposition of Defendant's Motion to Exclude Proposed Expert Testimony of Patent Attorney Q. Todd Dickinson"; United States District Court for the Eastern District of Arkansas; Case No. 4:18-CV-00500-JM; Apr. 21, 2020; pp. 1-180.
Zest Labs, Inc. v Walmart; ECF No. 290; Zest Labs, Inc. et al.; "Plaintiffs' Brief in Opposition of Defendant's Motion to Exclude Proposed Expert Testimony of Mark Lanning"; United States District Court for the Eastern District of Arkansas; Case No. 4:18-CV-00500-JM; Apr. 21, 2020; pp. 1-62.
Zest Labs, Inc. v Walmart; ECF No. 291; Zest Labs, Inc. et al.; "Zest Labs Inc.'S Reply Brief in Support of Its Motion for Partial Summary Judgment That Information in Walmart's Patent Application Was Not Generally Known or Readily Ascertainable"; United States District Court for the Eastern District of Arkansas; Case No. 4:18-CV-00500-JM; Apr. 21, 2020; pp. 1-18.
Zest Labs, Inc. v Walmart; ECF No. 292; Zest Labs, Inc. et al.; "Plaintiffs' Reply in Support of Their Motion to Exclude Testimony of Walmart's Damages Expert Dr. William Choi"; United States District Court fort he Eastern District of Arkansas; Case No. 4:18-CV-00500-JM; Apr. 21, 2020; pp. 1-20.
Zest Labs, Inc. v Walmart; ECF No. 293; Zest Labs, Inc. et al.; "Brief in Support of Plaintiffs' Motion to Exclude the Testimony of Walmart's Expert Witness, Dr. David P. DOBKIN"; United States District Court for the Eastern District of Arkansas; Case No. 4:18-CV-00500-JM; Apr. 21, 2020; pp. 1-13.
Zest Labs, Inc. v Walmart; ECF No. 294; Zest Labs, Inc. et al.; "Zest Labs Inc.'s Reply in Support of Their Motion for Partial Summary Judgment That Walmart Used and Disclosed Zest's Information in the Walmart Application"; United States District Court for the Eastern District of Arkansas; Case No. 4:18-CV-00500-JM; Apr. 21, 2020; pp. 1-39.
Zest Labs, Inc. v Walmart; ECF No. 295; Zest Labs, Inc. et al.; "Plaintiffs' Reply in Support of Their Motion to Exclude the Testimony of Walmart's Expert Witness, Dr. Catherine Adams Hutt"; United States District Court for the Eastern District of Arkansas; Case No. 4:18-CV-00500-JM; Apr. 21, 2020; pp. 1-23.
Zest Labs, Inc. v Walmart; ECF No. 296; Zest Labs, Inc. et al.; "Plaintiffs' Objections to and Motion to Strike Evidence Cited in Walmart's Responses to Zest Labs, Inc.'S Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.
Zest Labs, Inc. v Walmart; ECF No. 297; Zest Labs, Inc. et al.; "Plaintiffs' Memorandum in Support of Objections to and Motion to Strike Evidence Cited in Walmart's Responses to Zest Labs, Inc.'S Statement of Material Facts in Support of Its Motions for Partial for Summary Judgement and Motion for Summary Judgment"; United States District Court for the Eastern District of Arkansas; Case No. 4:18-CV-00500-JM; Apr. 21, 2020; pp. 1-5.
Zest Labs, Inc. v Walmart; ECF No. 298; Walmart; "Defendant's Consolidated Brief in Opposition to Plaintiffs' Objections to and Motions to Strike Evidence Cited by Walmart in Connection With Summary Judgment Motions (Dkts. 222 & 248)"; United States District Court for the Eastern District of Arkansas; Case No. 4:18-CV-00500-JM; May 4, 2020; pp. 1-18.

* cited by examiner

AUTOMATED INSPECTION SYSTEM

BACKGROUND

In providing goods to customers, in particular with regards to perishable items, produce, and food items, it is important to check that goods conform to government regulations, and industry and company standards. Conforming to these regulations and standards is an increasingly difficult task in today's global economy. At the same time, competitive demands require more efficient processes.

SUMMARY

Examples of the disclosure provide for an automated inspection system. The system includes an inspection component implemented on at least one computing device with at least one sensor configured to capture data about a good; and a communication component communicatively coupled to the computing device and configured to receive information regarding regulations and quality control standards associated with the good, and transmit the information regarding the acceptability of a good to an inventory system.

Other examples of the disclosure provide a method for inspecting a good. For example, captured image data of a good is obtained from a camera sensor on the computing device. The captured image data is processed to identify a good, further identify a good type associated with the good, and determine whether there are one or more defects associated with the good. An alert is generated if the good is deemed unacceptable. Notifications and alerts may also be sent when a good is deemed acceptable and/or becomes part of inventory.

Still other examples provide one or more computer storage devices storing computer-executable instructions for inspecting a good. The computer-executable instructions are executed by a computer to cause the computer to perform operations, including identifying a good and corresponding good type, obtaining information regarding regulations and quality control standards associated with a good type, obtaining sensor data of a computing device regarding a good; processing the obtained sensor data to identify one or more defects associated with the good; and generating an alert responsive to the good being deemed unacceptable.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Corresponding reference characters indicate corresponding parts throughout the drawings.

DETAILED DESCRIPTION

Figure 1:
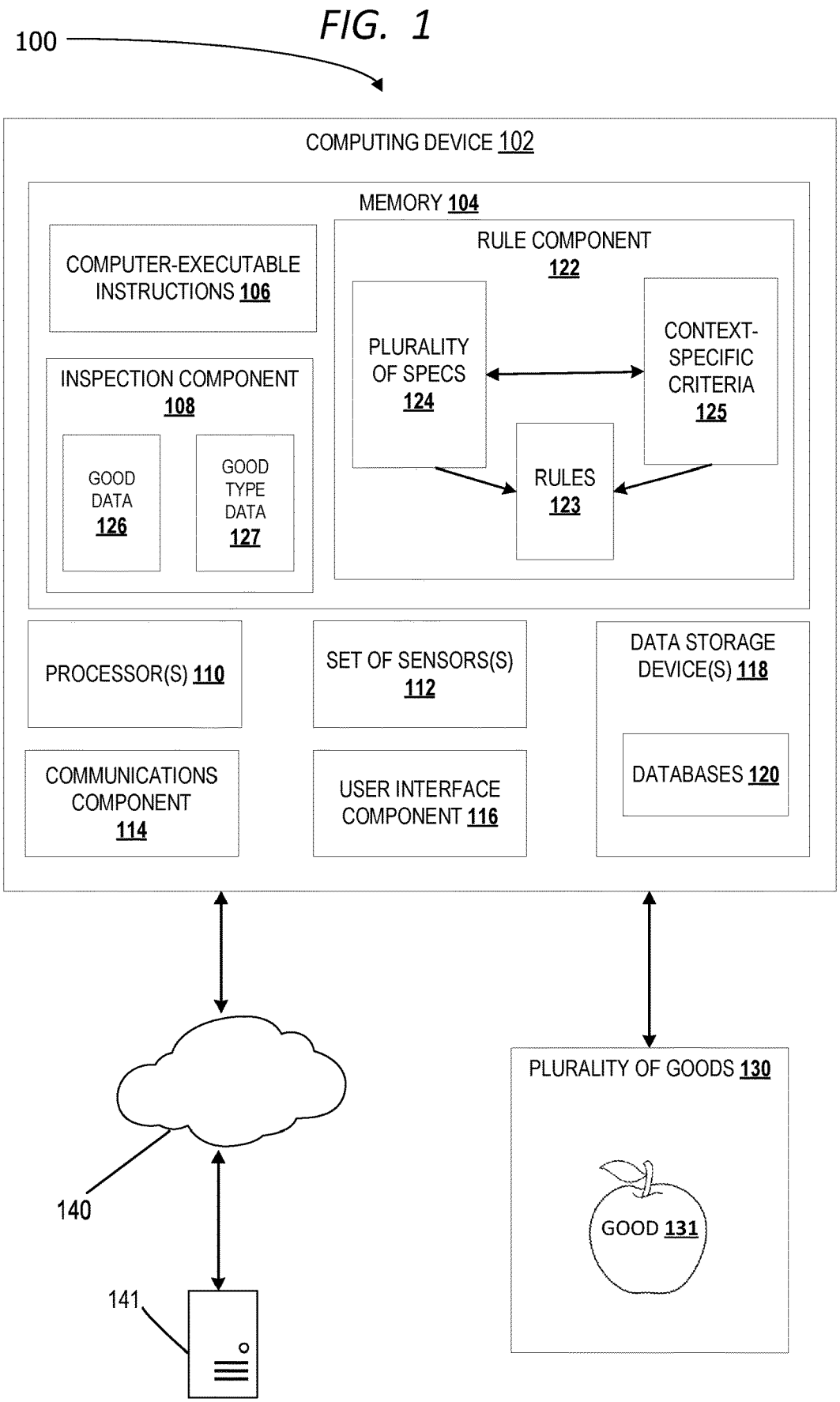
FIG. 1 is an exemplary block diagram illustrating a computing device for inspecting a good.

Goods, particularly perishable ones, are typically checked throughout acquisition, production, transportation, storage, and/or sales for any defects and other problems. For example, foods may become damaged during transportation and may become unsuitable for human consumption. Other items may be unsuitable even before leaving the facility where it was produced or grown.

To protect people, governments often require goods to meet certain regulations before they may be sold to the public. In addition to government regulations, many corporations and/or industries have their own standards. For instance, some companies may only want to sell produce grown or produced locally. The company may use such selectivity as a differentiating factor when comparing itself to its competitors. Furthermore, companies or local governmental agencies may implement local, regional, or seasonal standards for products. Recall notices for goods or other health and safety alerts also need to be addressed to ensure a good does not harm a person. Meeting the regulations and standards of the various governmental and corporate entities in today's complex and fast paced global economy is time consuming and may be financially prohibitive for many corporations.

In addition, the regulations and standards may change periodically or with very little notice, and changes may only affect certain goods and not others. Suppliers, distributors, and retailers are required to keep abreast of the changes. Additionally, companies that sell such goods may face significant sanctions in the form of fines or other measures that adversely affect the company if the proper regulations and standards are not followed. Currently, human operators manually check goods to ensure that they conform with regulations and standards. Thus, while human monitors may use certain types of equipment to assist, the overall process is manually labor intensive.

Referring to the figures, examples of the disclosure enable inspecting a good to ensure compliance with regulations and standards in an efficient manner. In some examples, an inspection component is provided for automatic analysis of one or more goods using a set of rules associated with a good by analyzing sensor data received from at least one of a set of sensors associated with the mobile computing device. The inspection component automates identifying defects or unsuitable characteristics associated with a good. The inspection component further minimizes human error while minimizing costs associated with the monitoring.

In other examples, the set of sensors include a set of one or more cameras or other image capture devices. The set of cameras provide real-time imaging of the one or more item(s) and/or data recording to the computing device. Images captured are used to identify defects in goods and/or determine if a good or goods meet specified criteria. Images may also be used to identify a good that is subject to an error notification. Images can also be used to track a good as it passes through the inspection process.

Other examples provide at least one infrared (IR) camera associated with a computing device. The IR camera(s) enables infrared thermography to generate accurate, automated non-contact temperature measurements of a good. This enables more non-contact monitoring of one or more goods for improved quality assurance of perishable goods more efficiently than thermocouples or other contact temperature sensors.

Moreover, the computing device in some examples connects to one or more remote computing devices via a network connection. This enables seamless integration with other inspection and process control systems for improved scalability over manual systems.

Referring to FIG. 1, an exemplary block diagram illustrates an automated inspection system 100 for inspecting one or more goods. In the example of FIG. 1, the computing device 102 communicating with a set of sensors 112 for gathering sensor data associated with a good 131 of a plurality of goods 130. Good 131 is evaluated based on a set of rules 123, which are generated from plurality of specifications 124 and context-specific criteria 125, to determine whether good 131 is acceptable for addition to inventory.

The computing device 102 represents any device executing instructions (e.g., as application programs, operating system functionality, or both) to implement the operations and functionality associated with the computing device 102. The computing device 102 may be a smartphone, mobile telephone, laptop, tablet, personal digital assistant, scanner, computing pad, netbook, gaming device, wearable device, and/or portable media player.

The computing device 102 may also include less portable devices such as personal computers, servers, kiosks, tabletop devices, and industrial control devices. Additionally, the computing device 102 may represent a group of processing units or other computing devices.

In some examples, the computing device 102 includes one or more processor(s) 110, a memory 104, and a communications component 114. The one or more processor(s) include any quantity of processing units. At least one processor of the one or more processors(s) 110 is programmed to execute computer-executable instructions 106 for implementing the examples herein. The computer-executable instructions 106 may be performed by the processor or by multiple processors within the computing device 102, or performed by a processor external to the computing device 102. In some examples, the processor is programmed to execute instructions such as those illustrated in the figures (e.g., FIG. 2 and FIG. 3).

In some examples, the one or more processor(s) represent an implementation of analog techniques to perform the operations described herein. For example, the operations may be performed by an analog computing device and/or a digital computing device.

The computing device 102 further has one or more computer readable media such as the memory 104. The memory 104 includes any quantity of media associated with or accessible by the computing device 102. The memory 104 may be internal to the computing device (as shown in FIG. 1), external to the computing device (e.g. external server 141), or both. In some examples, the memory 104 includes read-only memory and/or memory wired into an analog computing device.

The memory 104 stores data, such as one or more applications. The applications, when executed by the processor, operate to perform functionality on the computing device. The applications may communicate with counterpart applications or services such as web services accessible via a network. For example, the applications may represent downloaded client-side applications that correspond to server-side services executing in a cloud.

The memory 104 further stores one or more computer-executable components. Exemplary components include an inspection component 108. In other examples, the memory 104 includes an analysis engine, sensor data, image capture data, and/or processed sensor data.

In some examples, the inspection component 108, when executed by the processor of the computing device 102, causes the processor to obtain sensor data corresponding to a good from sensors associated with the computing device; process the obtained sensor data to identify a good and good type, retrieve a set of rules associated with the good type, and determine whether the good is acceptable based on the set of rules associated with the good type. Inspection component 108 may further comprise good data 126 and good type data 127 to identify goods and good types being inspected. In some instances, good data 126 and good type data 127 may be stored in databases 120 or external server 141, and retrieved by inspection component 108.

The set of sensors 112 is a set of one or more sensors associated with the computing device 102. The set of sensors may be used by computing device 102 to scan or obtain data regarding a good, and may include one or more image capture devices, one or more thermometers, one or more hygrometers, one or more barometers, one or more motion sensors, one or more spectrometers, or any other type of sensor. An image capture device may include an analog camera, a digital camera, an IR camera, or other type of camera. The set of sensors 112 may include one or more sensors integrated within the computing device 102 in some examples. In other examples, the set of sensors 112 includes one or more sensors exterior to the computing device 102. The inspection component 108 receives and/or obtains sensor data from the set of sensors 112. In some examples, the inspection component 108 analyzes camera image data and/or other sensor data to identify defects associated with a good. In other instances, a thermometer may be used to monitor heat radiating from a sealed good indicating whether a given good is properly sealed and/or enclosed within packaging. In other examples, a spectrometer may be used to determine information about an object or substance through analysis of its light properties.

Computing device 102, in some examples, communicates with external devices, cloud infrastructure, and networks via communications component 114. In FIG. 1, network 140 is depicted. External server 141 is communicatively coupled to network 140. Networks may include, without limitation, a local area network (LAN), such as an Ethernet connection, or a wide area network (WAN), such as the Internet. Networks may be a wired network or a wireless network, such as WI-FI. In other examples, the inspection component 108 may request the sensor data from a set of sensors (not shown) via the network 140. The set of sensors may transmit sensor data via the network in response to a request from an inspection component such as inspection component 108. In other examples, the set of sensors automatically transmits sensor data to the inspection component 108 in real time as the sensor data is generated. In still other examples, the sensor data is sent at regular intervals or in response to a predetermined event.

Communications component 114 may include a network interface card and/or computer-executable instructions (e.g., a driver) for operating the network interface card. Communication between the computing device and other devices may occur using any protocol or mechanism over any wired or wireless connection. In some examples, the communications interface is operable with short range communication technologies such as by using near-field communication (NFC) tags.

In some examples, an alert or notification is generated and output to one or more user interfaces via a user interface component 116. A user interface may be a screen that displays the alert to a user or a speaker that generates an audible sound which the user can hear. Other user interfaces are also possible. Examples of other interfaces are command line prompts, graphical user interfaces, augmented reality, tactile and feedback interfaces, digital menus, and the like.

The user interface component 116 may include a graphics card for displaying data and alerts to one or more users, as well as receiving data from one or more users. The user interface component 116 may also include computer-executable instructions (e.g., a driver) for operating the graphics card. Further, the user interface component 116 may include a display (e.g., a touch screen display or natural user interface) and/or computer-executable instructions (e.g., a driver) for operating the display. The user interface component 116 may also include one or more of the following to provide data to the user or receive data from the user: speakers, a sound card, a camera, a microphone, a vibration motor, one or more accelerometers, a BLUETOOTH brand communication module, global positioning system (GPS) hardware, and a photoreceptive light sensor. For example, the user may input commands or manipulate data by moving the computing device in a particular manner.

Rule component 122 may be used to generate a set of rules 123 by which a good is to be inspected. Aspects of rules 123 used to evaluate a good may be referred to as parameters of rules 123. The rule component 122 in this example is stored within the memory 104. In other examples, rule component 122 may be stored within one or more database(s) 120 within one or more data storage devices(s) 118. Databases 120 may store information regarding goods and good types, such as good data 126 and good type data 127 which may be used by the inspection component 108 to identify good 131 and/or a good type of good 131 or any other good in the of plurality of goods 130

In other examples, the data storage device(s) may also be implemented externally to computing device 102 such as in external server 141 and accessed via network 140. The data storage device(s) may include rotational storage, such as a disk. The data storage device(s) may also include non-rotational storage media, such as a solid-state drive (SSD) or flash memory. In some non-limiting examples, the data storage device(s) provide a shared data store accessible by two or more hosts in a cluster. For example, the data storage device may include a hard disk, a redundant array of independent disks (RAID), a flash memory drive, a storage area network (SAN), or other data storage device.

Rule component 122 generates a set of rules 123 from a plurality of specifications 124 and context-specific criteria 125. The plurality of specifications 124, in some instances, includes a set of one or more government regulations such as USDA regulations, industry standards, corporate policies, or any similar set of data governing standard for acceptable goods in a given environment, by which customized rules may be generated. Plurality of specifications 124 may comprise specifications such as a primary set of specifications and secondary set of specifications. A primary specification may be, for example, United States Department of Agriculture (USDA) specifications. A secondary set of specifications may be, for example, a company specification.

The different sets of specifications may be used together to generate a set of rules 123. For example, a primary specification may state that a good may not have any visible holes. A secondary specification may state the same good should be a specific color. Rule component 122 analyzes both primary and secondary specifications to generate a customized rule or set of rules. These rules may indicate, for example, that the good should be both free of holes and be a certain color in order to be deemed acceptable. Once rule component 122 generates a set of rules 123, rules 123 may be used by inspection component 108 to inspect a good or plurality of goods. It should be appreciated that one set of specifications may be used to modify another set of specifications or may be used to modify a set of rules generated from another set of specifications.

In addition to specifications, context-specific criteria 125 may be used to generate or modify rules 123. Context-specific criteria 125 may include, for example, location of the inspection, the season during which inspection is to occur, the supplier of the good, or government notifications or recall notifications pertaining to the good. For example, a peach inspected in Georgia may be required to be a different size than in other parts of the country. Therefore, context-specific criteria 125 for an inspection in Georgia may include the minimum size required for a peach. In another example, a recall notice may be issued for all peaches from a specific supplier. Therefore, context-specific criteria 125 for an inspection in all stores may mandate a rejection of all peaches from the specific supplier. In some instances, context-specific criteria 125 may be used together with plurality of specifications 124 to generate a customized set of rules 123. Alternatively, context-specific criteria 125 may be used to modify plurality of specifications 124 or rules 123. As an example of modifying plurality of specifications 124, if a specific store changes its context-specific criteria, that change may be propagated to other stores by changing certain specifications.

Rule component 122 may also implement decision making algorithms or hierarchical models to in generating rules 123. It should be appreciated that rules 123 is a customized set of rules created to analyze a good, such as good 131. Although a harmonious process may be envisioned, the possibility exists that conflicts may arise between each set of specifications and between the plurality of specifications 124 and the context-specific criteria 125. In such a case, rule component 122 may need to determine which specification or context-specific criteria will be used to generate rules 123. Differences between the plurality of specifications may be ascertained by rules component 122, in addition to differences between the specifications and the context-specific criteria. These differences may then be resolved to determine the appropriate parameter to be used to create rules 123. In some instances, plurality of specifications 124 may take priority over context-specific criteria 125. For example, if the USDA requires a maximum of 5% blemishes on a piece of fruit, and context-specific criteria allows for 7%, the USDA requirement would take precedence (such an instance may occur in a situation where the USDA requirement is updated prior to updating context-specific criteria). In this case, rules 123 would not be modified by context-specific criteria 125.

It should also be appreciated that conflict need not arise between the various specifications and context-specific criteria. Each of the specifications and the context-specific criteria may, in some cases, be directed to different aspects or parameters of the inspection. For example, a primary specification may concern the percentage of blemishes on a good, a secondary specification may concern the color of the good, and context-specific criteria may concern the size of the good. In other cases, even if the various specifications and context-specific criteria concern the same aspect or parameter (e.g. percentage of blemishes), each might work harmoniously. The primary specification may define a threshold value, a secondary specification may define an industry standard, while the context-specific criteria may define a regional requirement.

Thus, rules 123 may be generated in a variety of manners using plurality of specifications 124 and context-specific criteria 125. Rule component 122 is able to implement logic to determine which of the specifications and context-specific criteria will be used to generate or modify rules 123. It should also be noted, that rule component 122 may also modify previously existing rules stored in the device, or to update plurality of specifications 124 and context-specific criteria 125.

Specifications and context-specific criteria may be obtained from a variety of sources. They may be downloaded from remote servers, such as external server 141, uploaded via external devices or input by a user. Additionally, different sources may be used to obtain information for different specifications and context-specific criteria. For example, government accessible servers or websites may be used to obtain USDA specifications that may be used as primary specifications. Such servers may also be used to obtain alerts or recall notifications. Non-government sources such as industry group websites or trade organization databases may be used a source of secondary specifications. Internal servers may, in some cases, be used to obtain company specifications or requirements.

Specifications used to generate rules may relate to aspects or parameters of the inspection such as visible defects, unusual markings, temperature, indications of damage such as tears or punctures, smell, color consistency, packaging imperfections, and presence of other substances such as mold. Context-specific criteria used to generate and/or modify rules may include location, season, suppliers, and government notifications/recall notices, for example. Different context-specific criteria may be used for different goods, or even for the same good in different locations. An example of the latter—the previously cited example of the size of a peach in Georgia as compared to the size of a peach in other parts of the country. Context-specific criteria may also be combined in making determinations or generating rules. For example, a peach in Georgia may not just be required to be a certain size, but may also be required to be a certain color. A generated or modified rule based on context-specific criteria, may state a specific color and size. Another example would a recall notice issued for a particular supplier of peaches. A generated or modified rule in this case may require that any peach identified from a particular supplier be rejected. The above examples of specifications, context-specific criteria, and rules are non-limiting. Any attribute of a product that may be sensed by a sensor, directly or indirectly, or calculated based on sensor data, may be a basis for specifications, context-specific criteria, or a rule for a good. Additionally, external information sources (such as alerts from the USDA) may be used to generate or modify rules.

Figure 2:
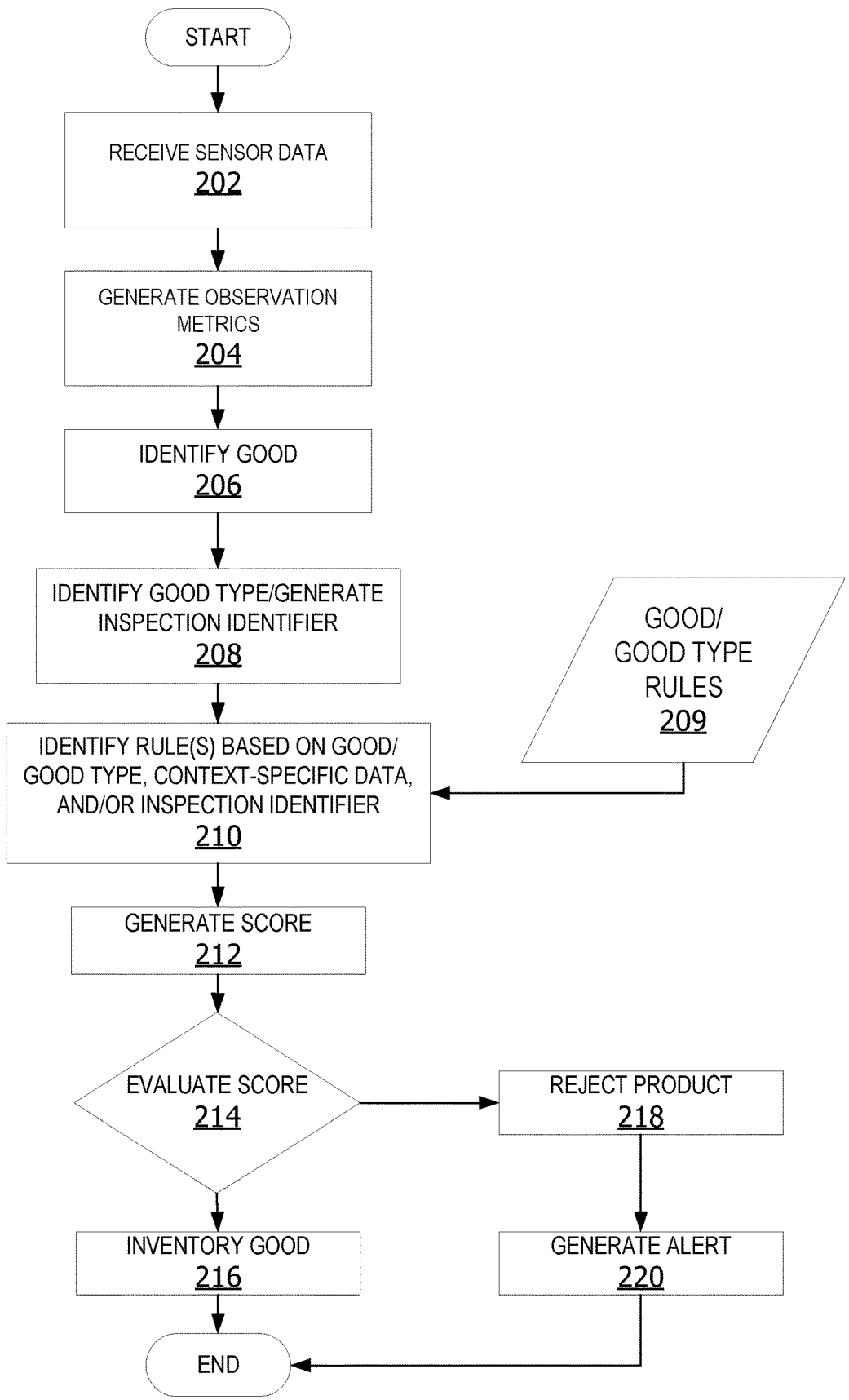
FIG. 2 is an exemplary flow chart of a process for determining whether a good is acceptable.

FIG. 2 is an exemplary flowchart illustrating operation of an automated system for inspecting a good or set of goods. The process shown in FIG. 2 may be performed by an inspection component executing on a computing device, such as, but not limited to, the inspection component 108 in FIG. 1. Further, execution of the operations illustrated in FIG. 2 is not limited to an inspection component. One or more computer-readable storage media storing computer-readable instructions may execute to cause at least one processor to implement the operations illustrated in FIG. 2.

The process begins at operation 202 when sensor data is received from one or more sensors. Sensor data may correspond to the images of the good, temperature of the good, state of the good, location of the inspection, or any attribute able to be sensed by the sensors. Sensor data may be generated by set of sensors 112. Additionally, a computing device such as computing device 102 may be calibrated using certain contextual sensor data such as location and time. Sensor data obtained at operation 202 may be used to determine whether a good is able to be inspected. If a good is not able to be inspected, operation 202 may issue a recommendation to remove the good or select a different good. The sensor data is processed at operation 204 by the inspection component, an analysis engine, and/or a machine learning component to generate observation metrics associated with a good. Observation metrics refer to any observed or calculated data related to a good, such as size, visible appearance, color, weight, and the like. Observation metrics may also comprise context-specific data such as location or time of year. At operation 206, the inspection component identifies the good based on the generated observation metrics by comparing the observation metrics to stored data such as good data 126 shown in FIG. 1 regarding various goods. For example, observation metrics may match the size, shape, and color of good 131 to an apple as depicted in FIG. 1. At operation 208, the inspection component identifies a good type based on stored data regarding various goods, such as good type data 127. For example, an apple may be identified as a fruit in the good type data 127. In other cases, an apple may be specifically identified as a "golden delicious apple" using good type data 127. Thus, good type data 127 may be used to store information regarding a certain type or classification of a good or a set of goods. In other words, good type data 127 may relate to a broader or narrower category depending on the system. It will be appreciated by one of skill in the art that the steps of identifying a good or good type may be combined or reversed with respect to certain types of goods.

The inspection component 108 may generate an inspection identifier at operation 208 related to the inspection of a good. The inspection identifier may be used to retrieve a set of stored customized rules, identify the inspection of a good in subsequent analysis, and/or may be used by the computing device to generate or retrieve primary and secondary specifications or context-specific criteria used to create one or more sets of customized rules for inspecting a good. The inspection identifier may be associated with a newly generated rule set and stored with the new rule set. The inspection identifier may then be used to retrieve the newly generated rule set a later point in time. The inspection identifier may be considered an identifier unique to a particular type of inspection. For example, if a banana is inspected in New York, a customized set of rules may be created for this inspection. By using an inspection identifier and associating it with a banana and New York, the customized set of rules can be easily retrieved the next time a banana in New York is inspected.

After a good or good type has been identified and/or an inspection identifier has been generated at operation 208 by the inspection component, one or more customized rules or sets of rules associated with the good or good type, the inspection identifier, and/or the context-specific data, is identified at operation 210. In some respects, the one or more customized rules or sets of rules may be present on the computing device and retrieved based on the inspection identifier. In other cases, the one or more customized rules or sets of rules may be obtained from a remote device, such as external server 141, using good/good type identification, the inspection identifier, and/or the context-specific data. In still other instances, a customized rule or set of rules may be created on demand in part by using context-specific criteria and an inspection identifier. Inspection component 108 may issue a request for customized rules along with an inspection identifier. At operation 210, the relevant specifications and context-specific criteria are used to create a customized rule or set of rules, and is associated with the inspection identifier. The customized set of rules may then be stored in the computing device for immediate use or future retrieval.

Good/good type rules 209 is an example of a customized rule or set of rules generated by a rule component, such as rule component 122 in FIG. 1. Good/good type rules 209 may be generated or customized on computing device 102 in FIG. 1 or retrieved from external server 141 in FIG. 1, as examples. Other sources of good/good type rules 209 are also possible. In some instances, a plurality of customized rules or sets of rules is stored on the computing device along with an inspection identifier. In other instances, only rules or a set of rules pertaining to an identified good are stored, and may be customized on demand.

If no rules or sets of rules associated with the identified good/good type and/or inspection identifier exist, a request may be issued to generate a rule set for a good associated with an inspection identifier. If no primary specification exists to create the appropriate rule or set of rules, the user may be prompted to provide a primary specification to generate the one or more rules or sets of rules. In some cases, a template may be provided to the user to provide the primary specification. A secondary specification may then be used to customize the primary specification. Additionally, if no secondary specification exists, the user may be prompted to provide a secondary specification. A template may be provided to the user to provide the secondary specification. The secondary specification may be then used in conjunction with the primary specification, or the secondary specification may be used to customize or modify the primary specifications. Furthermore, the rule or rule set may then be customized or modified by any context-specific criteria. The resulting customized rule or set of rules may then be stored with an associated inspection identifier. In this way, the inspection identifier may be used to store and retrieve customized rules or sets of rules.

Although depicted as being generated by specifications and context-specific criteria, customized rules or sets of rules may be generated in any manner, from data downloaded by the computing device, or by user input. Customized rules may also be created from a combination of other rules. For example, rules may be specific to a good or to a good type, either one or the other, or a combination. There may be specific rules regarding a banana, and general rules regarding fruit, which may be applicable to a particular good being inspected. There may also exist other rules specific to a particular location. Thus, a customized rule set may be generated that factors in the each of these rules. Other examples of customized rules are also possible. In some respects, the one or more rules or sets of rules may be a digitized representation of government requirements. In other aspects, the one or more rules or sets of rules may be a set of corporate policies. In still other aspects, the one or more rules or sets of rules may be related to industry standards. Other sources of one or more rules are also possible.

Based on the observation metrics determined at operation 204 which are used to identify a good at operation 206, context-specific data and/or good type at operation 208, a relevant customized rule or set of customized rules is identified at operation 210. For instance, if the observation metrics identify the good as a banana in California, a set of customized rules pertaining to bananas and fruit in California may be identified. These customized rules may be generated from USDA specifications stating that only bananas with less than 10% blemished surface may be sold, and from company specifications stating that only bananas of a certain size may be sold. Additionally, this customized rule or set of rules may state that only bananas of a certain ripeness are acceptable. In some instances, the computing device 102 may store customized rules associated with a variety of goods in memory 104 or databases 120 with an inspection identifier. If sensor data related to aspects of a good have not been obtained, such sensor data may be requested. In other instances, one or more customized rules are retrieved on an on-demand basis, for example, from external server 141, using an inspection identifier, such that only rules associated with the good under analysis is retrieved. Different specifications, and different priorities may be applied in generating a customized set of rules depending on the type of good or goods. For example, USDA specifications may take priority for generating a customized set of rules for a piece of fruit that may be sold to a consumer, whereas a store specific rule may take priority for generating a customized set of rules for clothing.

At operation 212, a score is generated based on an analysis of the good in relation to the one or more customized rules. The score may take the form of a numeric value, in which the inspection component generates the numeric value for the good being analyzed based on the one or more rules or set of customized rules. At operation 214, the score generated at operation 212 is evaluated to determine whether the good under analysis is acceptable A threshold score may be required in order for a good to be deemed acceptable. In other cases, a simple pass/fail analysis may be performed.

Additionally, grades may be assigned to the good based on the score. For example, a score of over ninety may result in the good being deemed "A" grade. In other instances, a grade may be used in place of a score. Grades may also be used to create customized rules or sets of rules or to generate scores or in combination with other processes described above. A piece of fruit labeled grade "A" may be more strictly inspected, or have a different set of rules associated with it, than another piece of fruit. For example, an apple labeled as grade "A" may only be allowed to have 2% blemishes as opposed to an unlabeled apple that is allowed to have 5% blemishes. Thus, an apple with 5% blemishes, as evaluated based on the observation metrics, might have a lower score if it is labeled as a grade "A" apple, and may be rejected as a result. Each aspect of the customized rules or sets of rules may be considered a parameter by which the good is the be evaluated.

If the good is deemed acceptable, i.e. its score is high enough or it meets the pass criteria, the good becomes part of inventory at operation 216. In some aspects, acceptability may mean that the good is deemed fit for another inspection to occur. This may be the case when a first inspection is performed at a gathering facility or the like, and a second inspection is performed at a distribution center. Other possibilities exist in which the steps of FIG. 2 may be performed multiple times. In some respects, the score generated may be evaluated along with other context-specific criteria, such as the time of year, location of inspection, or other criteria not particular to the good, in determining whether the good is deemed acceptable. A notification may be sent to a user device associated with a user, system, inventory tracker or the like, if a good is deemed acceptable. Additionally, operation 216 may comprise recommendations concerning inventory of the good. Recommendations may be based on observation metrics. For example, if observation metrics indicates that the good is frozen, operation 216 may recommend freezer inventory for the good.

If the good is not deemed acceptable, the good is rejected at operation 218. Rejection may be for any number of reasons, such as a score below a defined threshold, a score determined to be a "failing" score, or an insufficient score relative to other criteria such as location of the distribution center. If rejected, the good will not become part of inventory. In some respects, the good may be passed onto a secondary inspection. A secondary inspection may be a manual inspection, or an inspection at another facility. A secondary inspection may be performed whether or not the good passes a first inspection. If the good is rejected, an alert is generated at operation 220. In some cases, the generated alert is output to a user interface associated with a user device, such as a screen. In other cases, the generated alert may be sent to another computing device or inventory checker. The process terminates thereafter. Notifications and alerts may be sent whether a good is deemed acceptable or not. The notifications may identify a good or good type for which inspection has been performed. In addition to notifications, scores, alerts and the like, recommendations related to a good or good type. For example, a good that meets USDA specifications but not a context-specific rule may be deemed appropriate for sale at another location or through another channel. Multiple recommendations may be generated for a particular good or good type. Recommendations are not limited to rejected goods.

In FIG. 2, sensor data received from a sensor is processed to identify a good or good type. In some examples, sensor data processed to identify the good or good type may be images from a camera, data from a temperature sensor sucas a, thermometer, or other sensor.

While the operations illustrated in FIG. 2 are performed by a computing device or server, aspects of the disclosure contemplate performance of the operations by other entities. For example, a cloud service may perform one or more of the operations.

Figure 3:
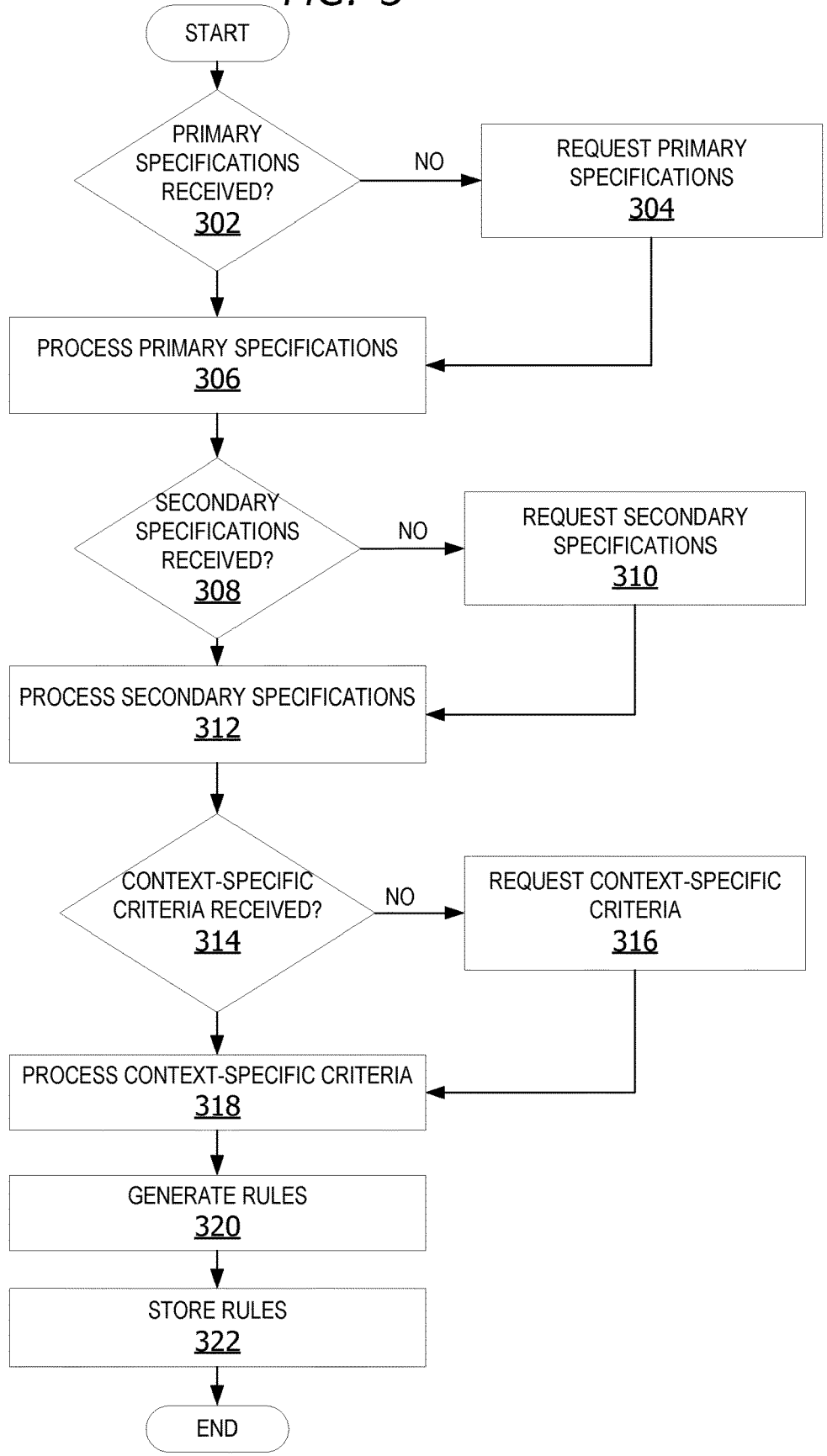
FIG. 3 is an exemplary flow chart of a process for creating a set of rules for a good.

FIG. 3 is an exemplary flow chart of a process for creating a customized rule or set of rules for a good. Other possibilities exist as to how a customized rule or set of rules may be generated. The process shown in FIG. 3 may be performed by a rule component executing on a computing device, such as, but not limited to, the rule component 122 in FIG. 1. Further, execution of the operations illustrated in FIG. 3 is not limited to a rule component. One or more computer-readable storage media storing computer-readable instructions may execute to cause at least one processor to implement the operations illustrated in FIG. 3.

A determination is made as to whether primary specifications are received from one or more sources at operation 302. Primary specifications, in some examples, include one or more government regulations or other industry standards and may be stored locally on a device or on a remote system. Other sources are also possible such as web servers, web services, internet servers, remote databases, and the like. In some aspects, the sources of primary specifications may be external to the computing device, such as a external server 141 in FIG. 1 or cloud infrastructure. In other aspects, the sources may be local to the device or added to the device using a USB drive or similar device. If the primary specifications have not been received, primary specifications are requested at operation 304 by a rule component, such as rule component 122 in FIG. 1 for example, or another similar component. The primary specifications are processed at operation 306 by the rule component, an analysis engine, and/or a like component. Processing is performed to generate relevant data regarding a customized set of rules to be created, associated with the primary specifications.

A determination is made as to whether secondary specifications are received from one or more sources at operation 308. Secondary specifications in some examples include corporate standards or policies. In some examples, the sources of secondary specifications may be external to the computing device, such as networked servers or drives. As with primary specifications, secondary specifications may be from web servers, web services, internet servers, remote databases, and the like. In other aspects, the secondary specification sources may be local to the device or added to the device using a USB drive or similar device. If the secondary specifications have not been received, secondary specifications are requested at operation 310 by a rule component, such as rule component 122 in FIG. 1 for example, or another similar component. The secondary specifications are processed at operation 312 by the inspection component, an analysis engine, and/or a like component. Processing is performed to generate relevant data regarding a customized set of rules to be created associated with the secondary specifications. Additionally, processing at this stage may resolve conflicts or determine associations with data generated from processing of the primary specifications. In a similar manner as explained with regards to primary and secondary specifications, the presence of context-specific criteria is determined at operation 314, requested at operation 316, and processed at operation 318. Similar to operation 312, processing at operation 318 may entail resolving conflicts or determining associations with primary or secondary specifications.

At operation 320, a customized rule or set of rules are generated based on the primary specifications, the secondary specifications, and the context-specific criteria. Customized rules may be specific to a particular good or good type, and to a specific location or entity. The customized rules may comprise a plurality of parameters by which a good is to be inspected. For example, a banana may have a specification of being yellow over at least 70% of its surface. Another specification may state that since a banana is a fruit, it may not have any puncture marks. Context-specific criteria may state that for organic labeling, the banana should be locally sourced. These different specifications and context-specific criteria may be used together to generate a rule or set of rules comprising parameters related to color, defects, and supplier, to be used when inspecting a particular banana. Additional specifications or context-specific criteria may be used that are specific to certain seasons or locations. For example, a set of specifications or context-specific criteria of a store in Georgia may specify that a peach should be of a certain color or size. Another specification or context-specific criteria may state that in a particular season, such as spring, the peach should be of a certain size relative to that season. Still other specifications or context-specific criteria may comprise an error notification, notifying a user and/or the system that a good or good type may be excluded outright, or that there is an exception to be implemented, or that further inspection may be required.

A customized rule or set of customized rules may be generated from any number of specifications or context-specific criteria. In some instances, as depicted in FIG. 3, a primary specification and a secondary specification may be used along with context-specific criteria to generate a customized set of rules. Although it is anticipated that specifications and context-specific criteria will work harmoniously, in instances of discrepancy, a hierarchy of specifications may be established. For instance, in the United States, regulations promogulated by the United States Department of Agriculture (USDA) may be prioritized over specifications of a local store. This may happen, for instance, when the USDA updates its specifications but certain local specifications have not been changed.

The generated set of customized rules are stored at operation 322. Rules may be stored on a computing device, such as computing device 102, in memory 104 for example, or databases 120, or external server 141 accessed via network 140. Rules may be storied with an inspection identifier to assist in future retrieval of the customized rules. Although the process described in FIG. 3 envisions government regulations as primary specifications and corporate standards as secondary specifications, regulations, standards, policies or any of the like may be used as either the primary or secondary specifications, or as context-specific criteria.

FIG. 3 depicts one embodiment of generating a customized rule or set of rules 123. Other embodiments are contemplated to generate rules 123 customized to a particular location, region, or season; or standardized for a set of stores or all stores. While the operations illustrated in FIG. 3 are performed by a computing device, aspects of the disclosure contemplate performance of the operations by other entities. For example, a cloud service may perform one or more of the operations.

Figure 4:
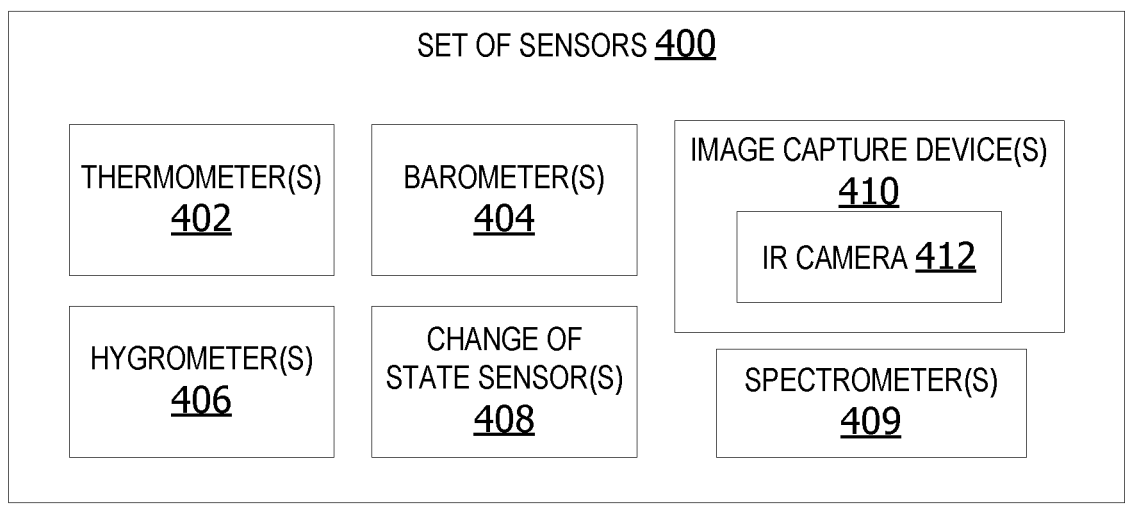
FIG. 4 is an exemplary block diagram illustrating a set of sensors.

FIG. 4 is an exemplary block diagram illustrating a set of sensors. The set of sensors 400 is a set of one or more sensors. In some cases, set of sensors 400 may be part of computing device 102 implementing inspection component 108. In other cases, set of sensors 400 may be communicatively coupled to computing device 102. The set of sensors 400 may be used to scan or obtain data regarding a good. The set of sensors 400 in some examples includes one or more thermometer(s) 402, one or more barometer(s) 404, one or more hygrometer(s) 406, one or more change of state sensor(s) 408, a spectrometer(s) 409, and/or one or more image capture device(s) 410. In some examples, the image capture device(s) 410 includes at least one IR camera 412. The sensors are used to generate or obtain sensor data, including context-specific data, related to a good. In some cases, sensors may work together or with other devices.

For instance, a GPS system may be used to identify the location of an inspection, which would result in an inspection system identifying a particular aspect of the good to be inspected. The relevant sensor data is acquired by the inspection system from the sensors. The context-specific data may then be used to retrieve context-specific criteria associated with the good. For example, if the GPS system informs that a peach being inspected is in Georgia, the context-specific data regarding location of the peach may be used to retrieve context-specific criteria, such as size requirements for peaches in Georgia.

A change of state sensor is a non-electrical, non-reversing sensor that monitors a change of state of the good, such as a change in temperature, a change in a state of matter, a change in a moisture level or texture, etc. A change of state of matter includes a change from ice to water, a change from water to steam, etc. A spectrometer is used to determine information about an object or substance through analysis of its light properties.

Sensor data from the thermometer(s) 402, barometer(s) 404, hygrometer(s) 406, and/or change of state sensor(s) 408, spectrometer(s) 409, may be sent in concert with image capture data generated by image capture device(s) 410 to the inspection component for evaluation. For example, hygrometer data indicating moisture levels of the good may be sent with IR image data to the inspection component. The inspection component analyzes the moisture data and IR data to determine whether a food item is moist and/or drying out.

Figure 5:
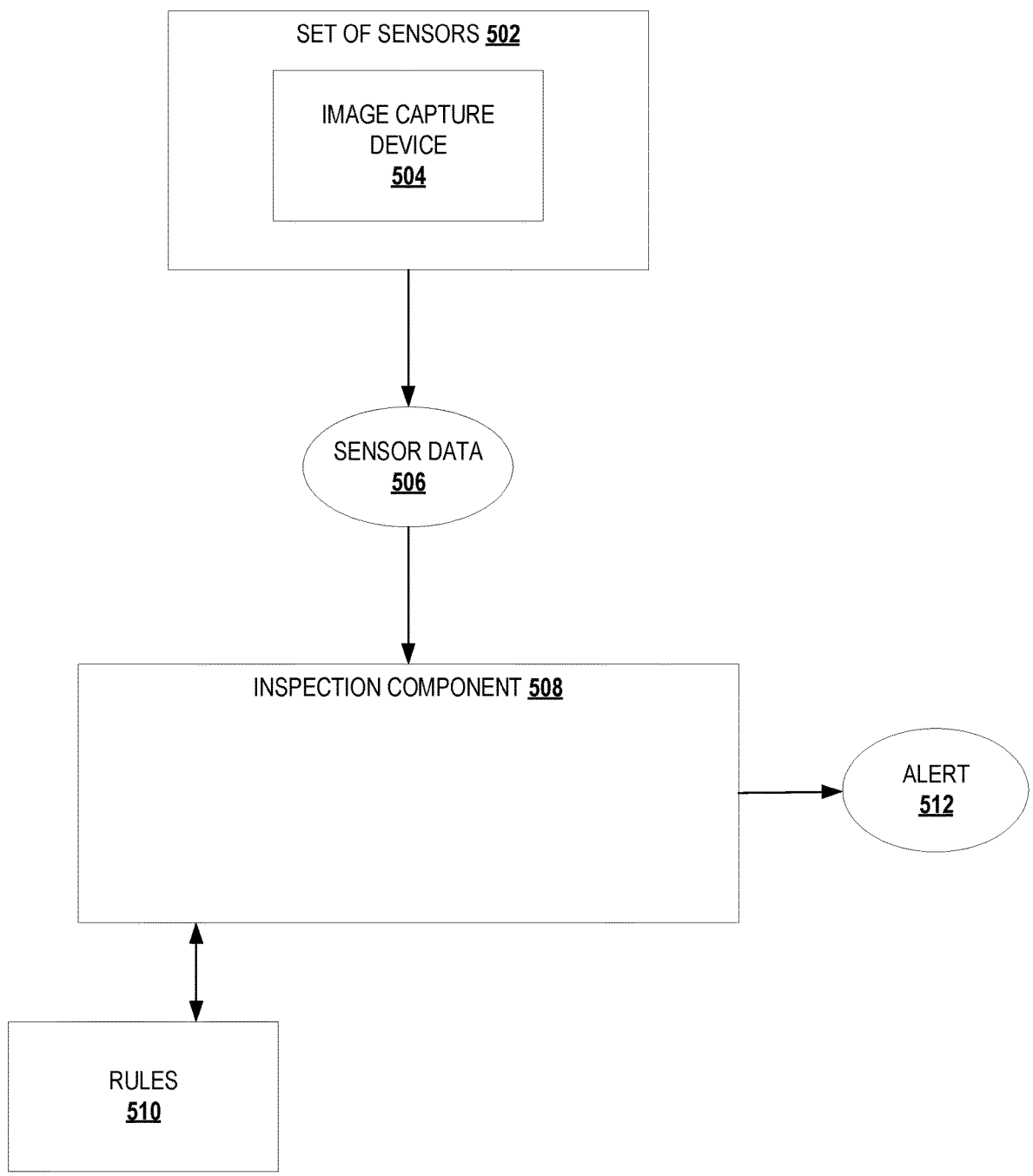
FIG. 5 is an exemplary block diagram illustrating a system for inspecting acceptability of a good.

FIG. 5 is an exemplary block diagram illustrating an automated inspection system for inspecting a good. The set of sensors 502 obtains data regarding the one or more goods. The set of sensors 502 includes one or more sensors for inspecting the good and/or the environment within and/or around the good. In this example, the set of sensors 502 incudes at least one image capture device 504. The image capture device 504 may be implemented as any type of device for capturing images. The image capture device 504 may generate still images or a series of images in a video. The image capture device 504 in this example may be implemented as an IR camera using thermographic sensors to generate images and/or a non-IR camera using light sensors to generate images.

In some examples, the image capture device 504 is permanently mounted. In other examples, the image capture device 504 is moveably mounted such that the image capture device may be moved or relocated to a non-permanent position. The image capture device 504 may include a color scale or gray scale. The image capture device 504 may optionally be set up with the color scale or gray scale to optimize the images generated by the image capture device 504.

The set of sensors 502 sends and/or provides sensor data 506 to an inspection component 508. In some examples, the sensor data may include IR camera still images, IR camera video images, digital video output, or other image data. For example, the sensor data 506 may include Moving Pictures Experts Group (MPEG) video output. In still other examples, the sensor data 506 may include temperature data, timestamp data, barometer data, hygrometer data, change of state data, non-IR digital video data, analog video data, still images, light properties or other data generated by one or more sensors.

In some examples, the inspection component 508 compares the sensor data 506 to good data stored in a database to identify a good, good type, good location, good temperature, good packaging integrity, good freshness, moisture level, or other factors associated with the good.

In other examples, inspection component 508 analyzes the sensor data 506 to detect environment changes around the good, as well as changes within the good.

The inspection component 508 retrieves rules 510. Rules 510 may be a customized set of rules generated by a rule component, such as rule component 122 in FIG. 1. Rules 510 may be generated from specifications pertaining to government regulations, industry standards, company policies or the like. Rules 510 may be specific to a particular good, a set of goods, a type of good, or a classification of goods. Rules 510 may be applied to a sample good or to each good in a batch. In some aspects, rules 510 may be generated locally on the computing device, while in other aspects, rules 510 may be retrieved from another device, network server, or cloud infrastructure. Rules 510 may also be based on specifications specific to a particular store, group of stores, region, or other location. Additionally, rules 510 may be further customized in any given manner and various combinations of specifications may be combined to create rules 510. It should be appreciated by one of skill in the art that rules 510 may be customized in a variety of ways to address the needs of specific stores, institutions, inspections, personnel, agencies, management, or the like.

The inspection component utilizes rules 510 in combination with sensor data 506 to determine whether a good is acceptable. Any attribute of a good that may be sensed or calculated from a sensor is thus an attribute that may be used as a basis or parameter of a rule. Rules 510 may thus cover any attribute of a good that may be sensed or calculated from a sensor. By way of example, a computing device implementing an inspection component with an image sensor such as image capture device 504 may take a picture of a good The computing device comprising the image capture device 504 includes one or more GPS sensors in some examples. Based on analysis of image data generated by the image capture device and analyzed by an inspection component of an inspection system, the computing device determines whether the good has any defects, such as a puncture. Based on analysis of GPS data to determine location, the computing device retrieves location specific criteria, such as a minimum size of a good in a particular location, for example. Thus, a set of rules regarding defects and location-specific criteria may be implement by a computing device with an image capture device, such as image capture device 504, and GPS sensor, in some examples. In other examples, inspection component 508 may be calibrated for a specific location and identify rules and criteria to use in analyzing sensor data based on the calibrated location. Data such as location and season may be considered context-specific data.

The inspection component 508 in some examples analyzes the sensor data 506 to determine when a factor exceeds a threshold and/or a state of an item changes. In response to a factor exceeding a threshold and/or a state change, the inspection component 508 generates an alert 512 for one or more users. The alert 512 may be a screen notification, audible alarm, a light, a flashing light, a verbal warning, a visual or other textual notification displayed by an output device, or other alarm.

An alert 512 may be generated based on any number of factors. For example, an alert 512 may be generated upon inspection of a good upon the determination that a foreign substance is present on the good. The presence of a foreign substance may be determined by inspecting a good and determining the presence of a substance on the surface of the good that is not related to the good based on the good data retrieved. For example, based on identifying characteristics, such as color or texture, the foreign substance may be determined to be mold. The alert 512 identifies one or more users associated with the inspection system to perform a secondary inspection and/or remove a good from a set of goods being inspected, in some examples.

Figure 6:
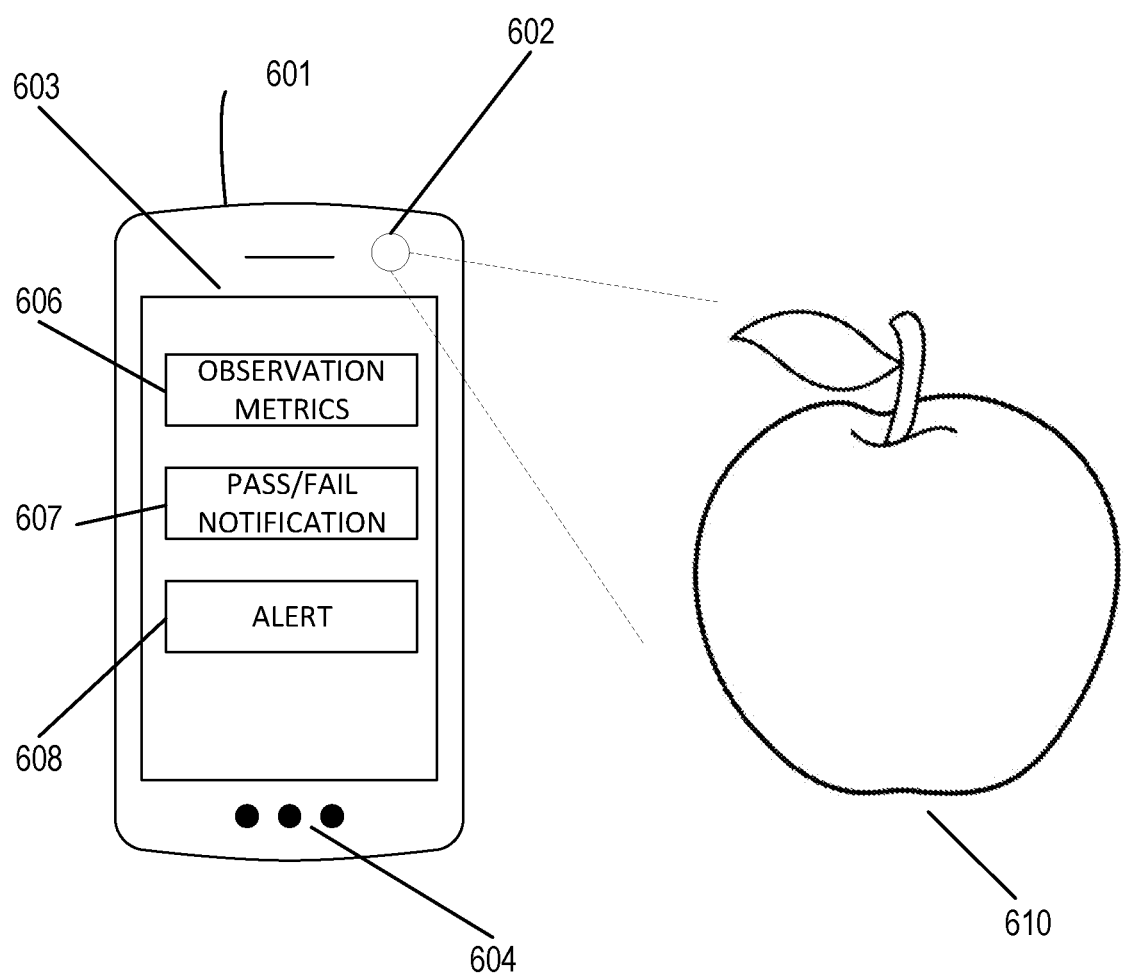
FIG. 6 is an exemplary illustration of a computing device inspecting a good.

FIG. 6 is an exemplary illustration of an inspection device inspecting a good. Inspection device 601 may be an illustrative example of one implementation of computing device 102 in FIG. 1. Inspection device 601 comprises image sensor 602 and touchscreen 603. Additionally, inspection device 601 may comprise other sensors represented at 604. Inspection device 601 uses image sensor 602 to obtain sensor data regarding good 610. Sensor data is analyzed by the inspection component (not shown) on inspection device 601 to generate observation metrics 606. In some instances, the inspection component may reside on a remote computing device or remote server such as external server 141 in FIG. 1. In some instances, observation metrics 606 may be presented to a user via touchscreen 603. In other instances, observation metrics 606 may be transmitted for further analysis, such as to external server 141 in FIG. 1. In addition to observation metrics 606, any data associated with the inspection may be sent to an external or remote server for further analysis. For example, sensor data, identification of a good or identification of a good type, inspection scores, pass/fail determination or any of the like may be sent to an external or remote server. Such data may be used for historical tracking, to build a knowledge database, to create a baseline for machine learning, to aid in quality control review or any such data driven analysis.

Observation metrics 606 are compared against a rule or set of rules (not shown) generated by a rule component, such as rule component 122 in FIG. 1, and stored in memory 104, databases 120, or external server 141 (and accessed via network 140) as depicted in FIG. 1, to determine whether good 610 is acceptable. In some instances, when good 610 is deemed acceptable, a notification 607 is generated and shown on touchscreen 603. Likewise, if good 610 is deemed unacceptable, notification 607 regarding its unacceptability may be displayed on touchscreen 603. In addition to notifications, an alert 608 may be sent to inspection device 601 and displayed on touchscreen 603.

In some instances, an alert 608 may be generated if a particular reason for unacceptability may cause other goods to be deemed unacceptable. For example, if sensor data indicates that the good is contaminated. An alert 608 may also be generated if the sensor data indicates a good does not meet one or more of a set of rules. For example, one rule for an item may be the absence of any puncture or hole. Another rule may be a certain threshold percentage of defects permitted over the surface of a good. In some examples, if analysis of the sensor data indicates the identified defects of a good exceeds the rule (higher or lower than the threshold), an alert 608 is generated and output via the user interface component 116.

Figure 7:
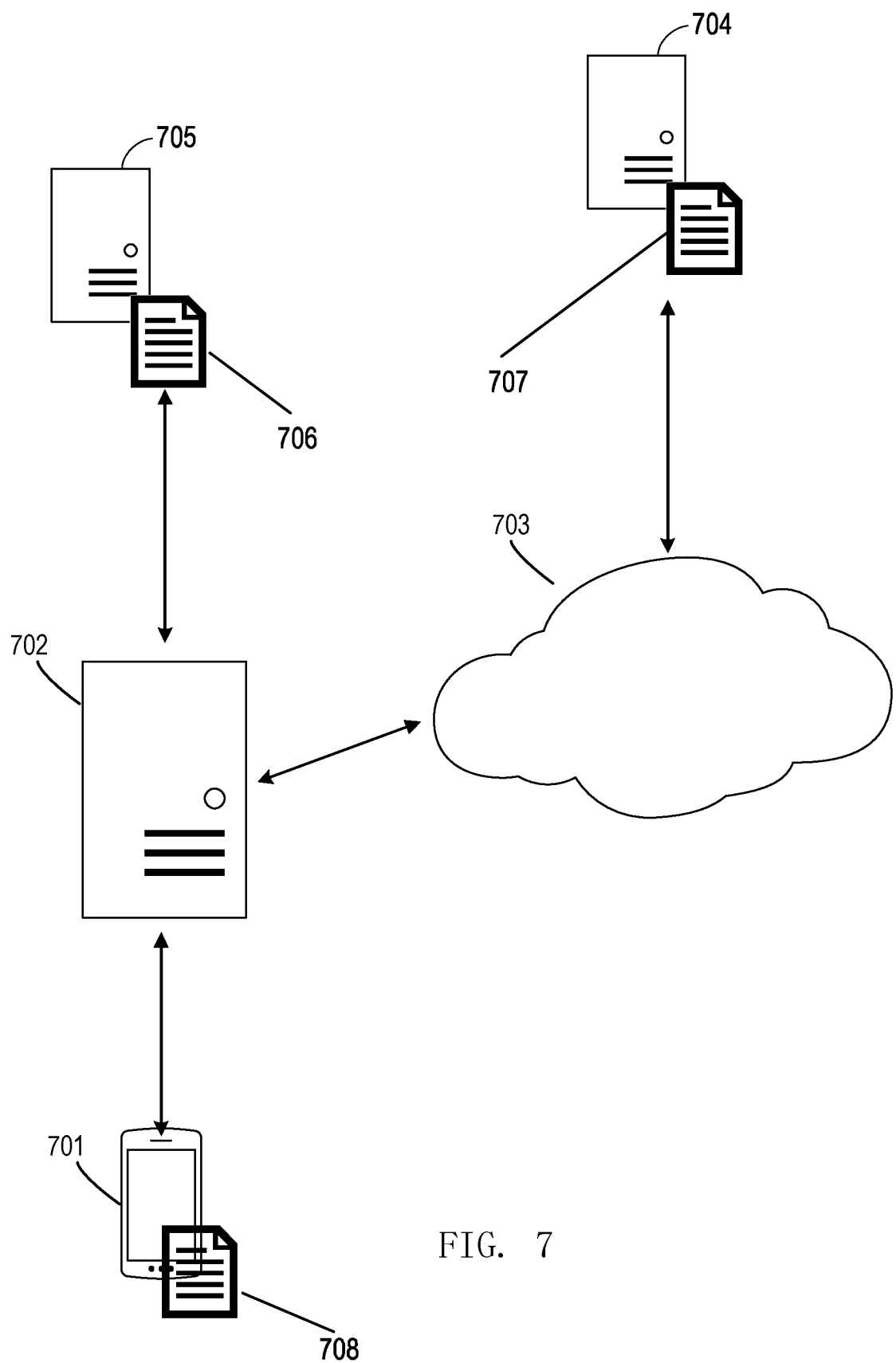
FIG. 7 is an exemplary illustration of a system for a computing device obtaining specifications to generate a set of rules.

FIG. 7 is an exemplary illustration of a system for a computing device obtaining specifications to generate a set of rules. Referring to FIG. 7, inspection device 701 is communicatively coupled to local server 702. Connectivity may be accomplished through WIFI or BLUETOOTH or other wireless or wired protocols. Local server 702 is communicatively coupled to other servers on the network such as network server 705. Local server 702 is also communicatively coupled to remote server 704 through cloud infrastructure 703. In some instances, inspection device 701 may be communicatively coupled to network server 705 and cloud infrastructure 703 directly. Specifications 706 and 707 are stored on network server 705 and remote server 704 respectively. Specifications 706 and 707 are downloaded to inspection device 701 to generate rules 708 as described in relation to FIG. 3. In some instances, rules 708 may be generated on inspection device 701 from specifications 706 and 707. In other instances, rules 708 may be generated on a remote device, such as network server 705 and downloaded to inspection device 701. Still other variations are possible, such as part of the generation of rules 708 taking place on inspection device 701 and part of generation of rules 708 taking place on network server 705. Additionally, rules 708 may be generated on demand, or generated and stored on inspection device 701 or network server 705 for later use. The process shown in FIG. 7 may be performed by a processor, such as, but not limited to, processor 110 in FIG. 1. Further, execution of the operations illustrated in FIG. 7 is not limited to a specific processor. One or more computer-readable storage media storing computer-readable instructions may execute to cause at least one processor to implement the operations illustrated in FIG. 7.

Additional Examples

At least a portion of the functionality of the various elements in FIG. 2, FIG. 3, FIG. 5, FIG. 6 and FIG. 7 may be performed by other elements in FIG. 1, FIG. 4, FIG. 5, FIG. 6 and FIG. 7, or an entity (e.g., processor, web service, server, application program, computing device, etc.) not shown in FIG. 1, FIG. 4, FIG. 5, FIG. 6 and FIG. 7.

In some examples, the operations illustrated in FIG. 2, FIG. 3, FIG. 5, FIG. 6 and FIG. 7 may be implemented as software instructions encoded on a computer readable medium, in hardware programmed or designed to perform the operations, or both. For example, aspects of the disclosure may be implemented as a system on a chip or other circuitry including a plurality of interconnected, electrically conductive elements. Operations may be performed on a single device, or multiple devices communicatively coupled together. Aspects of the disclosure may be performed at one location or different locations communicatively coupled together. Additionally, results of some operations may be sent as copies to different devices. For instance, a network server may be used to generate a rule or set of rules. The rule or set of rules may then be sent to a plurality of computing devices. Additionally, aspects of the disclosure such as notifications and alerts may be sent to a single device, multiple devices or used by other applications or programs.

Specifications used to generate rules may be obtained from a variety of sources. For instance, The United States Department of Agriculture provide instructions in PDF format on how to grade/score various types of produce. For example, USDA Grade beef may be prime, select, or choice; produce may be extra fancy, fancy, US 1, US 2. These grades represent different levels of quality based on mostly objective measures. Another example involves USDA allowed tolerances—percentages of defects acceptable for a good to be saleable to the public, and different grades have different tolerances. USDA also sets standards for defects, bruising, or injury, and appearance of a good. In addition to government specifications, company or local specifications may also be used, either independently, or in combination with other specifications.

Similar to specifications, good data and good type data may be obtained from a variety of sources, such as, but without limitation, historical data collected by companies, trade groups, or other such organizations. Data associated with a good may be manually input by users or those with knowledge of the good. Information gathered by sensors may be used to not only to determine whether a good is acceptable but also its shelf life, i.e., for how long it may be acceptable. Other determinations may include expiration date, use-by dates, sell-by dates etc. For instance, bananas stored in special rooms may be treated with temperature and/or gas to ripen or delay ripening, which may help determine the shelf life. Ripeness would assist in forecasting sell-by dates.

Communication and storage may be accomplished by a variety of devices and through a variety of means. Communication may be over wireless networks such as BLUETOOTH or Wi-Fi or over wired networks such as ethernet and phone lines. Communication may be direct through devices, through corporate intranets, the internet, cloud based services or the like. Similarly, storage of data and components may be on computing devices, local servers, network servers, remote servers, cloud applications and devices, mobile devices, kiosks etc.

While the aspects of the disclosure have been described in terms of various examples with their associated operations, a person skilled in the art would appreciate that a combination of operations from any number of different examples is also within scope of the aspects of the disclosure.

Alternatively, or in addition to the other examples described herein, examples include any combination of the following:

wherein the sensors are external to the computing device;

wherein the good type is identified based on the generated sensor data;

wherein the one or more sensors include at least one of a thermometer, an infrared sensor, a camera, a barometer, a hygrometer, or a change-of-state sensor;

wherein the one or more sensors include at least one of a thermometer, an infrared sensor, a camera, a barometer, a hygrometer, or a change-of-state sensor;

wherein the image capturing device is an infrared camera;

process data received from the image capturing device and identify one or more defects associated with a good;

wherein the one or more goods are edible;

wherein the one or more observation metrics is used to generate one or more grades associated with the one or more observation metrics, the inspection score generated based on the one or more grades;

wherein the one or more parameters of the one or more observation metrics are included in the first rule set;

wherein the one or more observation metrics are used to generate a recommendation for storing the first good;

wherein the processor is further configured to execute the computer-executable instructions to determine whether to modify the first rule set;

wherein the first rule set is a customized context-specific rule set associated with the identified good type and an identified location;

performing an inspection of the first good using the first rule set to generate an inspection score for determining whether to accept the first good;

obtaining sensor data from one or more sensors associated with the computing device;

processing the obtained sensor data to identify the one or more observation metrics;

wherein the alert comprises at least one of an alert to replace items, an alert to remove items, an alert to add items, an alert to relocate items, or an alert associated with contamination;

receiving a request to customize the one or more rule sets, the request including an inspection identifier;

generating a secondary specification set template for prompting a user to provide the one or more secondary specification sets;

comparing the one or more secondary specification sets with the one or more primary specification sets to identify one or more differences between the one or more secondary specification sets and the one or more primary specification sets;

analyzing the one or more differences to identify one or more parameters for generating the one or more rule sets;

scanning the one or more goods to generate sensor data associated with the one or more goods;

analyzing the sensor data to generate a selection recommendation for selecting, from the one or more goods, the first good;

scanning the first good to generate sensor data associated with the first good;

analyzing the sensor data to identify a good type associated with the first good;

analyzing the sensor data to generate an inspection recommendation for inspecting the first good;

comparing the one or more observation metrics with one or more parameters included in the first rule set to generate one or more grades associated with the one or more observation metrics, the inspection score generated using the one or more grades;

identifying one or more second observation metrics associated with a second good of the one or more goods;

identifying inventory data associated with the first good;

analyzing the inventory data to determine whether to modify the first rule set;

analyzing the one or more observation metrics to generate a storage recommendation for storing the first good.

The term "Wi-Fi" as used herein refers, in some examples, to a wireless local area network using high frequency radio signals for the transmission of data. The term "BLUETOOTH" as used herein refers, in some examples, to a wireless technology standard for exchanging data over short distances using short wavelength radio transmission. The term "cellular" as used herein refers, in some examples, to a wireless communication system using short-range radio stations that, when joined together, enable the transmission of data over a wide geographic area. The term "NFC" as used herein refers, in some examples, to a short-range high frequency wireless communication technology for the exchange of data over short distances.

Example Operating Environment

Figure 8:
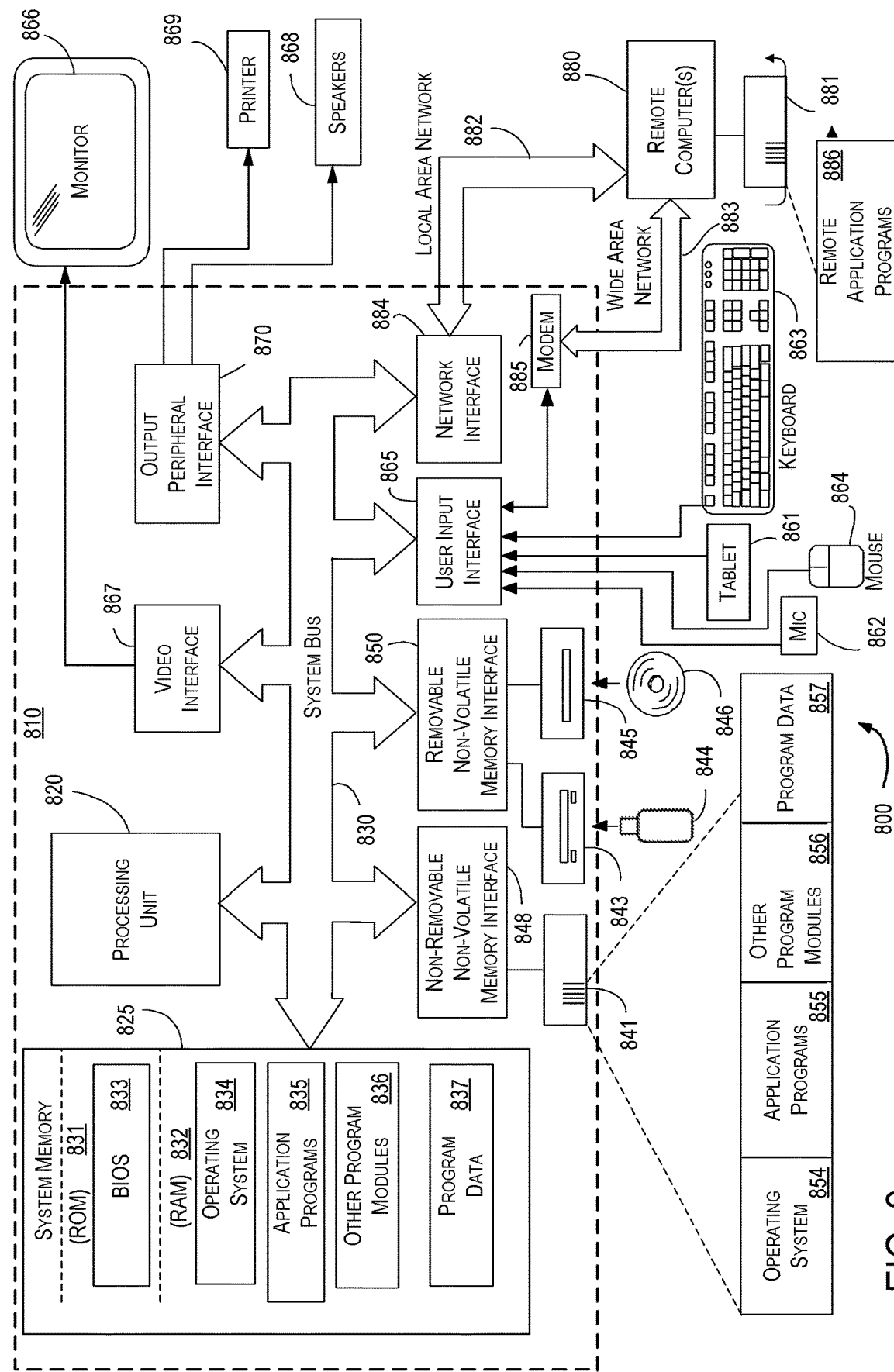
FIG. 8 is an exemplary embodiment of a computing environment for implementing processes and methods described herein.

FIG. 8 is a block diagram illustrating an example operating environment 800 for a computing device (e.g., computing device 102). The operating environment 800 is only one example of a suitable computing environment and is not intended to suggest any limitation as to the scope of use or functionality of the disclosure. Neither should the operating environment 800 be interpreted as having any dependency or requirement relating to any one or combination of components illustrated in the example operating environment 800.

The disclosure is operational with numerous other general purpose or special purpose computing system environments or configurations. Examples of well-known computing systems, environments, and/or configurations that may be suitable for use with the disclosure include, but are not limited to: personal computers, desktop computers, laptop computers, tablet devices, netbooks, handheld devices, mobile telephones, wearables, gaming devices, portable media players, server computers, kiosks, set top boxes, tabletop devices, multiprocessor systems, microprocessor-based systems, programmable consumer electronics, network PCs, minicomputers, mainframe computers, distributed computing environments that include any of the above systems or devices, and the like.

The disclosure may be described in the general context of computer-executable instructions, such as program modules, being executed by a computer. Generally, program modules include routines, programs, objects, components, data structures, and so forth, which perform particular tasks or implement particular abstract data types. The disclosure may also be practiced in distributed computing environments where tasks are performed by remote processing devices that are linked through a communications network. In a distributed computing environment, program modules may be located in local and/or remote computer storage media including memory storage devices and/or computer storage devices. As used herein, computer storage devices refer to hardware devices.

With reference to FIG. 8, an example system for implementing various aspects of the disclosure may include a general purpose computing device in the form of a computer 810. Components of the computer 810 may include, but are not limited to, a processing unit 820, a system memory 825, and a system bus 830 that couples various system components including the system memory to the processing unit 820. The system bus 830 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 810 typically includes a variety of computer-readable media. Computer-readable media may be any available media that may be accessed by the computer 810 and includes both volatile and nonvolatile media, and removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or the like. Read only memory (ROM) 831 and random access memory (RAM) 832 are examples of computer storage media. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which may be used to store the desired information and which may be accessed by the computer 810. Computer storage media does not, however, include propagated signals. Rather, computer storage media excludes propagated signals. Any such computer storage media may be part of computer 810.

Communication media typically embodies computer-readable instructions, data structures, program modules or the like in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

The system memory 825 includes computer storage media in the form of volatile and/or nonvolatile memory such as ROM 831 and RAM 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 8 illustrates operating system 834, application programs, such as application programs 835 (e.g., appliance management environment), other program modules 836 and program data 837.

The computer 810 may also include other removable/non-removable, volatile/nonvolatile computer storage media. By way of example only, FIG. 8 illustrates a hard disk drive 841 that reads from or writes to non-removable, nonvolatile magnetic media, a universal serial bus (USB) port 843 that provides for reads from or writes to a removable, nonvolatile memory 844, and an optical disk drive 845 that reads from or writes to a removable, nonvolatile optical disk 846 such as a CD ROM or other optical media. Other removable/non-removable, volatile/nonvolatile computer storage media that may be used in the example operating environment include, but are not limited to, magnetic tape cassettes, flash memory cards, digital versatile disks, digital video tape, solid state RAM, solid state ROM, and the like. The hard disk drive 841 is typically connected to the system bus 830 through a non-removable memory interface such as interface 848, and USB port 843 and optical disk drive 845 are typically connected to the system bus 830 by a removable memory interface, such as interface 850.

The drives and their associated computer storage media, described above and illustrated in FIG. 8, provide storage of computer-readable instructions, data structures, program modules and other data for the computer 810. In FIG. 8, for example, hard disk drive 841 is illustrated as storing operating system 854, application programs 855 (e.g., an appliance management environment), other program modules 856 and program data 857. Note that these components may either be the same as or different from operating system 834, application programs 835, other program modules 836, and program data 837. Operating system 854, application programs 855, other program modules 856, and program data 857 are given different numbers herein to illustrate that, at a minimum, they are different copies.

A user may enter commands and information into the computer 810 through input devices such as a tablet, or electronic digitizer 861, a microphone 862, a keyboard 863 and pointing device 864, commonly referred to as mouse, trackball or touch pad. Other input devices not shown in FIG. 8 may include a joystick, game pad, digital camera, scanner, or the like. These and other input devices are often connected to the processing unit 820 through a user input interface 865 that is coupled to the system bus, but may be connected by other interface and bus structures, such as a parallel port, game port or a universal serial bus (USB). A monitor 866 or other type of display device is also connected to the system bus 830 via an interface, such as a video interface 867. The monitor 866 may also be integrated with a touchscreen panel or the like. Note that the monitor and/or touchscreen panel may be physically coupled to a housing in which the computer 810 is incorporated, such as in a tablet device. In addition, computers such as the computer 810 may also include other peripheral output devices such as speakers 868 and printer 869, which may be connected through an output peripheral interface 870 or the like.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810, although only a memory storage device 881 has been illustrated in FIG. 8. The logical connections depicted in FIG. 8 include one or more local area networks (LAN) 882 and one or more wide area networks (WAN) 883, but may also include other networks. Such networking environments are commonplace in offices, enterprise-wide computer networks, intranets and the Internet.

When used in a LAN networking environment, the computer 810 is connected to the LAN 882 through a network interface controller or adapter 884. When used in a WAN networking environment, the computer 810 typically includes a modem 885 or other means for establishing communications over the WAN 883, such as the Internet. The modem 885, which may be internal or external, may be connected to the system bus 830 via the user input interface 860 or other appropriate mechanism. A wireless networking component such as comprising an interface and antenna may be coupled through a suitable device such as an access point or peer computer to a WAN or LAN. In a networked environment, program modules depicted relative to the computer 810, or portions thereof, may be stored in the remote memory storage device. By way of example, and not limitation, FIG. 8 illustrates remote application programs 886 as residing on memory storage device 881. It may be appreciated that the network connections shown are exemplary and other means of establishing a communication link between the computers may be used.

The examples illustrated and described herein as well as examples not specifically described herein but within the scope of aspects of the disclosure constitute an example appliance management environment. For example, the elements illustrated in FIG. 1, FIG. 4, FIG. 5, FIG. 6 and FIG. 7, such as when encoded to perform the operations illustrated in in FIG. 2, FIG. 3, FIG. 5, FIG. 6 and FIG. 7, constitute an example means for sensing data pertaining to a good (e.g. sensors 112), an example means for inspecting data related to a good (e.g., inspection component 108,); an example means for generating a rule or set of rules pertaining to a good (e.g., rule component 122); and/or an example means for sending notifications and alerts related to a good (e.g. communications component 114, user interface component 116)

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

While the disclosure is susceptible to various modifications and alternative constructions, certain illustrated examples thereof are shown in the drawings and have been described above in detail. It should be understood, however, that there is no intention to limit the disclosure to the specific forms disclosed, but on the contrary, the intention is to cover all modifications, alternative constructions, and equivalents falling within the spirit and scope of the disclosure. Exemplary computer readable media include flash memory drives, digital versatile discs (DVDs), compact discs (CDs), floppy disks, and tape cassettes. By way of example and not limitation, computer readable media comprise computer storage media and communication media. Computer storage media include volatile and nonvolatile, removable and non-removable media implemented in any method or technology for storage of information such as computer readable instructions, data structures, program modules and the like. Computer storage media are tangible and mutually exclusive to communication media. Computer storage media are implemented in hardware and exclude carrier waves and propagated signals. Computer storage media for purposes of this disclosure are not signals per se. Exemplary computer storage media include hard disks, flash drives, and other solid-state memory. In contrast, communication media typically embody computer readable instructions, data structures, program modules, or the like, in a modulated data signal such as a carrier wave or other transport mechanism and include any information delivery media.

Although described in connection with an exemplary computing system environment, examples of the disclosure are capable of implementation with numerous other general purpose or special purpose computing system environments, configurations, or devices.

Examples of well-known computing systems, environments, and/or configurations that may be suitable for use with aspects of the disclosure include, but are not limited to, mobile computing devices, personal computers, server computers, hand-held or laptop devices, multiprocessor systems, gaming consoles, microprocessor-based systems, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, and the like. Such systems or devices may accept input from the user in any way, including from input devices such as a keyboard or pointing device, via gesture input, proximity input (such as by hovering), and/or via voice input.

Examples of the disclosure may be described in the general context of computer-executable instructions, such as program modules, executed by one or more computers or other devices in software, firmware, hardware, or a combination thereof. The computer-executable instructions may be organized into one or more computer-executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other examples of the disclosure may include different computer-executable instructions or components having more or less functionality than illustrated and described herein.

In examples involving a general-purpose computer, aspects of the disclosure transform the general-purpose computer into a special-purpose computing device when configured to execute the instructions described herein.

The examples illustrated and described herein as well as examples not specifically described herein but within the scope of aspects of the disclosure constitute exemplary means for inspecting a good. For example, the elements illustrated FIG. 1, FIG. 4, FIG. 5, FIG. 6 and FIG. 7, such as when encoded to perform the operations illustrated in in FIG. 2, FIG. 3, FIG. 5, FIG. 6 and FIG. 7, constitute exemplary means for inspecting a good; and exemplary means for generating a rule or set of rules pertaining to a good.

In other examples, the elements illustrated in FIG. 1, FIG. 4, FIG. 5, FIG. 6 and FIG. 7, such as when encoded to perform the operations illustrated in in FIG. 2, FIG. 3, FIG. 5, FIG. 6 and FIG. 7, constitute exemplary means for obtaining sensor data related to a good; exemplary means for sending notifications and alerts related to a good; and exemplary means for obtaining specifications and data related to a good or good type.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A computing system for inspecting one or more goods, the computing system comprising:
   at least one sensor configured to scan the one or more goods, the one or more goods being perishable food items comprising at least one of fruits and vegetables;
   a memory device storing data associated with one or more rule sets and computer-executable instructions, the one or more rule sets governing acceptable parameters of the one or more goods;
   a database configured to store electronic identifying information associated with the one or more goods; and a processor configured to execute the computer-executable instructions to:
obtain the electronic identifying information associated with the one or more goods from the database;
generate sensor data associated with a first good based on a scan of the one or more goods by the at least one sensor;
analyze the sensor data obtained by the at least one sensor associated with the first good of the one or more goods;
identify the first good of the one or more goods and a good type associated with the identified first good based on analysis, by the processor, of the sensor data in view of the electronic identifying information associated with the first good obtained from the database;
identify context-specific data associated with the first good;
determine, from the one or more rule sets, a first rule set associated with the identified good type and the context-specific data associated with the first good;
generate one or more observation metrics associated with the first good;
compare the one or more observation metrics with one or more of the parameters included in the first rule set to generate one or more grades associated with the one or more observation metrics;
generate an inspection score for the first good using the determined first rule set, the inspection score generated based on the one or more grades; and
based on the generated inspection score, output a notification for the first good, the notification indicating whether or not the first good is acceptable.

2. The computing system of claim 1, wherein the processor is further configured to execute the computer-executable instructions to:
analyze the sensor data to generate one or more of a first recommendation for selecting the first good from the one or more goods, or a second recommendation for inspecting the first good.

3. The system of claim 1,
wherein the one or more rule sets include government-based and industry-based standards for the one or more goods and supplier-based standards for the one or more goods;
wherein the context-specific data includes at least one of a geographic location where the first good is inspected, a season during which the first good is inspected, recall restrictions imposed on the first good, and restrictions imposed on one or more suppliers of the first good; and
wherein the processor is configured to execute the computer-executable instructions to determine the first rule set associated with the first good based on the one or more rule sets and the context-specific data associated with the first good, the first rule set including the government-based and industry-based standards for the first good, the supplier-based standards for the first good, the geographic location where the first good is inspected, the season during which the first good is inspected, the recall restrictions imposed on the first good, and the restrictions imposed on one or more suppliers of the first good.

4. The computing system of claim 1, wherein the processor is further configured to execute the computer-executable instructions to determine whether to modify the first rule set.

5. The computing system of claim 1, wherein the processor is further configured to execute the computer-executable instructions to:
analyze the one or more observation metrics to generate a recommendation for storing the first good.

6. A computer-implemented method for inspecting one or more goods, the computer-implemented method comprising:
receiving one or more primary specification sets for inspecting the one or more goods, the one or more goods being perishable food items comprising at least one of fruits and vegetables, the one or more primary specification sets including a first primary specification set associated with a first good type;
receiving one or more secondary specification sets for inspecting the one or more goods, the one or more secondary specification sets including a first secondary specification set associated with the first good type;
receiving context-specific criteria associated with inspecting the one or more goods,
based on the one or more primary specification sets, the one or more secondary specification sets, and the context-specific criteria, generating one or more rule sets for inspecting the one or more goods, the one or more rule sets including a first rule set generated using the first primary specification set, the first secondary specification sets, and the context-specific criteria, the first rule set associated with the first good type;
providing at least one sensor configured to scan the one or more goods;
providing a database configured to store electronic identifying information associated with the one or more goods;
providing at least one computing device including a programmable processor;
scanning the one or more goods via the at least one sensor;
generating sensor data associated with a first good based on the scanning of the one or more goods by the at least one sensor;
obtaining, via the processor, the electronic identifying information associated with the one or more goods from the database;
analyzing, via the processor, the sensor data associated with the first good in view of the electronic identifying information associated with the first good obtained from the database;
identifying, via the processor and based on the analyzing step, the first good of the one or more goods;
identifying, via the processor, context-specific data associated with the first good;
determining whether the first good is associated with the first good type;
generating, via the processor, one or more observation metrics associated with the first good;
comparing, via the processor, the one or more observation metrics with one or more parameters included in the first rule set to generate one or more grades associated with the one or more observation metrics;
on condition that the first good is associated with the first good type, performing, via the processor, an inspection of the first good using the first rule set to generate an inspection score for determining whether to accept the first good, the inspection score being generated by the processor based on the one or more grades,
transmitting, via the processor, the sensor data, the inspection score, the identification of the first good, and the first good type to a remote system, wherein the transmitted sensor data, inspection score, identification of the first good, and first good type are utilized to build a knowledge database regarding inspection of the one or more goods.

7. The computer-implemented method of claim 6, wherein the primary specification includes government-based and industry-based standards for the one or more goods, and the secondary specification includes supplier-based standards for the one or more goods;
wherein the context-specific data includes at least one of a geographic location where the first good is inspected, a season during which the first good is inspected, recall restrictions imposed on the first good, and restrictions imposed on one or more suppliers of the first good; and
further comprising, executing, via the processor, the computer-executable instructions to determine the first rule set associated with the first good based on the one or more rule sets and the context-specific data associated with the first good, the first rule set including the government-based and industry-based standards for the first good, the supplier-based standards for the first good, the geographic location where the first good is inspected, the season during which the first good is inspected, the recall restrictions imposed on the first good, and the restrictions imposed on one or more suppliers of the first good.

8. The computer-implemented method of claim 6, further comprising:
analyzing the one or more observation metrics to generate a storage recommendation for storing the first good.

9. The computer-implemented method of claim 6, further comprising:
receiving a request to generate the one or more rule sets, the request including an inspection identifier; and
based on the inspection identifier, generating a primary specification set template for prompting a user to provide the one or more primary specification sets.

10. The computer-implemented method of claim 6, further comprising:
receiving a request to customize the one or more rule sets, the request including an inspection identifier; and
based on the inspection identifier, generating a secondary specification set template for prompting a user to provide the one or more secondary specification sets.

11. The computer-implemented method of claim 6, wherein generating the one or more rule sets further comprises:
comparing the one or more secondary specification sets with the one or more primary specification sets to identify one or more differences between the one or more secondary specification sets and the one or more primary specification sets; and
analyzing the one or more differences to identify one or more parameters for generating the one or more rule sets.

12. The computer-implemented method of claim 6, further comprising:
comparing the one or more secondary specification sets with the one or more primary specification sets to identify one or more differences between the one or more secondary specification sets and the one or more primary specification sets;
analyzing the one or more differences to determine whether the one or more secondary specification sets conflicts with the one or more primary specification sets; and
on condition that the one or more secondary specification sets conflicts with the one or more primary specification sets, generating a notification.

13. The computer-implemented method of claim 6, wherein identifying the first good further comprises:
analyzing the sensor data to generate a selection recommendation for selecting, from the one or more goods, the first good.

14. The computer-implemented method of claim 6, wherein determining whether the first good is associated with the first good type further comprises:
analyzing the sensor data to identify a good type associated with the first good.

15. The computer-implemented method of claim 6, wherein performing the inspection of the first good further comprises:
analyzing the sensor data to generate an inspection recommendation for inspecting the first good.

16. The computer-implemented method of claim 6, further comprising:
identifying inventory data associated with the first good; and
analyzing the inventory data to determine whether to modify the first rule set.

17. The computer-implemented method of claim 6, wherein performing the inspection of the first good further comprises:
identifying one or more first observation metrics associated with the first good;
identifying one or more second observation metrics associated with a second good of the one or more goods; and
comparing the one or more second observation metrics with the one or more first observation metrics to determine whether to modify the first rule set.

18. One or more computer storage media embodied with computer-executable instructions, the one or more computer storage media comprising:
a rule component that, upon execution by at least one processor:
receives one or more rule sets for inspecting one or more goods associated with one or more good types, the one or more goods being perishable food items comprising at least one of fruits and vegetables, the one or more rule sets governing acceptable parameters of the one or more goods;
receives one or more context-specific criteria for inspecting one or more goods associated with the one or more good types, and
uses the one or more rule sets and the one or more context specific criteria to generate one or more customized rule sets for inspecting the one or more goods associated with the one or more good types; and
an inspection component that, upon execution by the at least one processor, is configured to:
analyze sensor data generated by the at least one processor in response to a scan of the one or more goods by at least one sensor, and analyzes the sensor data to identify a first good of the one or more goods,
identify context-specific data associated with the first good of the one or more goods,
determine whether the first good is associated with a first good type of the one or more good types,
generate one or more observation metrics associated with the first good;

compare the one or more observation metrics with one or more parameters included in the first rule set to generate one or more grades associated with the one or more observation metrics; and, on condition that the first good is associated with the first good type, perform an inspection of the first good using a first rule set associated with the first good type to generate an inspection score for determining whether to accept the first good, the inspection score being generated based on the one or more grades.

19. The one or more computer storage media of claim 18, wherein the one or more rule sets include government-based and industry-based standards for the one or more goods and supplier-based standards for the one or more goods;

wherein the context-specific data includes at least one of a geographic location where the first good is inspected, a season during which the first good is inspected, recall restrictions imposed on the first good, and restrictions imposed on one or more suppliers of the first good; and wherein the processor is configured to execute the computer-executable instructions to determine the first rule set associated with the first good based on the one or more rule sets and the context-specific data associated with the first good, the first rule set including the government-based and industry-based standards for the first good, the supplier-based standards for the first good, the geographic location where the first good is inspected, the season during which the first good is inspected, the recall restrictions imposed on the first good, and the restrictions imposed on one or more suppliers of the first good.

* * * * *